United States Patent
Dodic et al.

(10) Patent No.: US 9,938,260 B2
(45) Date of Patent: Apr. 10, 2018

(54) SOLUBLE GUANYLATE CYCLASE ACTIVATORS AND THEIR USE

(71) Applicant: GlaxoSmithKline Intellectual Property Development Limited, Brentwood, Middlesex (GB)

(72) Inventors: Nerina Dodic, Les Ulis (FR); Anne Marie Jeanne Bouillot, Les Ulis (FR)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/509,895

(22) PCT Filed: Sep. 18, 2015

(86) PCT No.: PCT/IB2015/057219
§ 371 (c)(1),
(2) Date: Mar. 9, 2017

(87) PCT Pub. No.: WO2016/042536
PCT Pub. Date: Mar. 24, 2016

(65) Prior Publication Data
US 2017/0305888 A1 Oct. 26, 2017

Related U.S. Application Data

(60) Provisional application No. 62/052,537, filed on Sep. 19, 2014.

(51) Int. Cl.
*A61K 31/445* (2006.01)
*C07D 405/14* (2006.01)
*C07D 401/14* (2006.01)

(52) U.S. Cl.
CPC ......... *C07D 405/14* (2013.01); *C07D 401/14* (2013.01)

(58) Field of Classification Search
CPC .................................................... C07D 405/14
USPC ......................................................... 514/316
See application file for complete search history.

(56) References Cited

FOREIGN PATENT DOCUMENTS

| WO | 2009071504 A1 | 6/2009 | |
|----|---------------|--------|---|
| WO | 2010015653 A1 | 2/2010 | |
| WO | 2010099054 A2 | 9/2010 | |
| WO | WO 2010099054 | * 9/2010 | ........... C07D 401/04 |

* cited by examiner

*Primary Examiner* — Nizal Chandrakumar
(74) *Attorney, Agent, or Firm* — Nora L. Stein; Edward R. Gimmi

(57) ABSTRACT

The invention relates to activators of soluble guanylate cyclase and their use in pharmaceutical compositions, primarily topically administered ophthalmic compositions. The pharmaceutical compositions are useful for reducing intraocular pressure in animals of the mammalian species.

10 Claims, No Drawings

SOLUBLE GUANYLATE CYCLASE ACTIVATORS AND THEIR USE

This application is a 371 national phase entry of International Application No. PCT/IB2015/057219, filed Sept. 18, 2015, which claims the benefit of U.S. Provisional Application No. 62/052537, filed Sept. 19, 2014, which is incorporated herein in its entirety.

FIELD OF THE INVENTION

The invention relates to activators of soluble guanylate cyclase (sGC), pharmaceutically acceptable salts thereof, pharmaceutical compositions, processes for their preparation and their use in medicine, primarily topically administered ophthalmic compositions. The pharmaceutical compositions are useful for reducing intraocular pressure (IOP) in animals of the mammalian species. The present invention also relates to administering such pharmaceutical compositions to animals of the mammalian species, including humans, for reducing IOP, including elevated IOP caused by glaucoma or ocular hypertension.

BACKGROUND OF THE INVENTION

Glaucoma is an optic neuropathy resulting in irreversible loss of visual function over time. Glaucoma is considered the second leading cause of blindness in the world. Predictions are for approximately 80 million people afflicted with glaucoma worldwide by 2020 (*Quigley and Broman, Br J Ophthalmol* 2006). Frequently, but not always, glaucoma is associated with elevated IOP which is recognized as an important risk factor for the disease. Ocular hypertension, a condition associated with elevated IOP that has not yet progressed to causing irreversible glaucomatous damage, is believed to represent the earliest stage of glaucoma. Therapeutic agents devised for the treatment of glaucoma and ocular hypertension have been designed to lower IOP, which remains the sole, proven treatable risk factor of the disease.

The drugs currently used for the treatment of glaucoma and ocular hypertension include prostaglandin analogs (e.g., latanoprost, bimatoprost, travoprost, tafluprost), beta-adrenergic blockers (e.g., timolol, betaxolol, levobunolol), alpha-adrenergic agonists (e.g., brimonidine, paraamino-clonidine), parasympathomimetics (e.g. pilocarpine, carbachol, acethylcholineesterase inhibitors), sympathomimetics (e.g., epinephrine, dipivalyl-epinephrine), carbonic anhydrase inhibitors (e.g., dorzolamide, brinzolamide). Pressure in the eye (IOP) is determined by the balance of aqueous humor production and aqueous humor outflow. It is generally accepted that elevated IOP is the result of compromised aqueous humor outflow. Thus, compounds that increase the outflow of aqueous humor are considered preferable for reducing IOP in glaucoma and ocular hypertensive patients. Prostaglandin analogs, sympathomimetics and parasympathomimetics are believed to decrease IOP by increasing aqueous outflow, whereas beta-blockers, alpha-adrenergic agonists and carbonic anhydrase inhibitors are believed to decrease IOP by reducing aqueous humor production. Prostaglandin analogs cause undesirable effects, such as increased conjunctival hyperaemia and iris hyperpigmentation, for example. Parasympathomimetics induce undesirable accommodative changes leading to blurring of vision. Sympathomimetics can also stimulate aqueous humor production which partially counteracts their effect on aqueous humor outflow and thus limits their resultant effect on IOP regulation. Some antiglaucoma drugs, e.g., timolol, produce systemic effects. These adverse events can lead to poor patient compliance and may necessitate withdrawal of drug therapy.

As a consequence, a need still exists to identify and develop anti-glaucoma drugs that specifically enhance aqueous humor drainage from the eye and, preferably, have a more limited adverse event profile.

Of the two primary aqueous humor outflow pathways in the eye, the conventional/trabecular outflow pathway represents the more attractive target since it is the site of outflow obstruction that leads to ocular hypertension. As reviewed by Ellis (*Cell Physiol Biochem* 2011) nitric oxide donors and guanylate cyclase activators have been shown to decrease IOP in humans, rabbits and monkeys. Nitric oxide is an endogenous activator of the soluble guanylate cyclase enzyme which in turn catalyzes the generation of cyclic GMP as a second messenger molecule. The role of the nitric oxide—soluble guanylate cyclase—cyclic GMP pathway in IOP regulation is well established (*Ellis, Cell Physiol Biochem* 2011). Components of this pathway, such as endothelial and neuronal type nitric oxide synthases responsible for the endogenous generation of nitric oxide, are present in the outflow pathway tissues. Thus, stimulation of sGC represents a novel ocular anti-hypertensive approach, regardless of whether the reduction in IOP through enhancement of aqueous humor drainage is caused by modulation of cell volume of trabecular meshwork or Schlemms Canal cells (*Ellis, Cell Physiol Biochem* 2011) or trabecular meshwork contractility (*Stumpff and Wiederholt, Ophthalmologica* 2000). Modulation of cell volume and/or contractility of structures in the trabecular outflow pathway had been proposed as mechanistic rationales for IOP regulation.

In U.S. Pat. No. 5,652,236, a method for reducing IOP in the mammalian eye by administration of guanylate cyclase inhibitors is claimed. In that context, it was surprising that guanylate cyclase activators were found to also reduce IOP.

SUMMARY OF THE INVENTION

The present invention relates to novel compounds which are 2-pyridine piperidine carboxylic acid activators of sGC. Specifically, the invention is directed to compounds of formula (I), and pharmaceutically acceptable salts thereof:

(I)

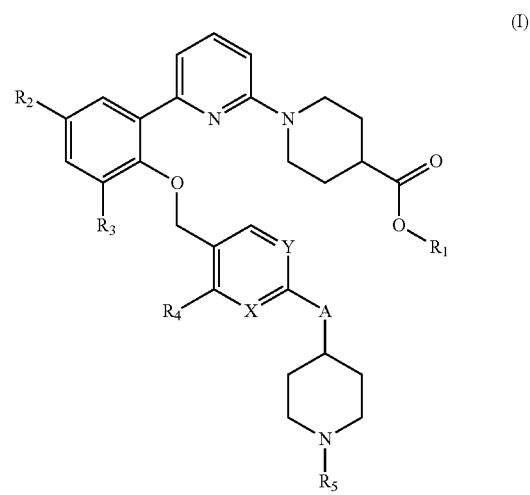

(I)

wherein:

$R_1$ is selected from H and —$C_{1-3}$alkyl;

$R_2$ and $R_3$ are each independently selected from H and halogen;

$R_4$ is selected from H, —$C_{1-3}$alkyl, —O—$C_{1-3}$alkyl, —O—$C_{3-4}$cycloalkyl, —O—$(CH_2)_p$-oxetanyl, and —O—$(CH_2)_p$-tetrahydrofuranyl;

X and Y are each CH; or if X is N, then Y is CH; or if Y is N then X is CH;

A is absent or O;

$R_5$ is selected from —$C_{1-4}$ alkyl, —$C_{3-4}$ cycloalkyl, —$(CH_2)_n$CN, —$(CH_2)_n$CF$_3$, —$(CH_2)_m$-tetrahydrofuranyl, —$(CH_2)_m$-oxetanyl, —$C_{2-5}$ alkyl-OH, —$C_{2-5}$ alkyl-OCH$_3$ and —CO—$R_6$;

$R_6$ is selected from —$C_{1-6}$ alkyl and —$C_{3-6}$ cycloalkyl, optionally substituted by —OH, —OCH$_3$, —CN, COOH or —F, or $R_6$ is —$(CH_2)_m$-tetrahydrofuranyl or —$(CH_2)_m$-oxetanyl, or R6 is a $(CH_2)_m$-4 to 5-membered heterocycle;

n is 1 or 2;

m is 0 or 1; and p is 0 or 1.

The compounds of the invention are activators of sGC. Therefore, the present invention is directed to a method for activating sGC which method comprises contacting a cell with a compound of Formula (I), or a pharmaceutically acceptable salt thereof. The invention is still further directed to a method of activating sGC activity and treatment of disorders associated therewith using a compound of the invention or a pharmaceutical composition comprising a compound of the invention.

In one embodiment, the invention is directed to a method of treating an sGC-mediated disease or disorder which comprises administering a therapeutically effective amount of a compound according to Formula (I), or a pharmaceutically acceptable salt thereof, to a patient (a human or other mammal, particularly, a human) in need thereof. Such sGC-mediated diseases or disorders include diseases or disorders associated with poor aqueous humor drainage or elevated intraocular pressure. Such diseases or disorders include, but are not limited to, glaucoma and ocular hypertension.

In one embodiment, the invention is directed to to a pharmaceutical composition comprising a compound of the invention according to Formula (I), or a pharmaceutically acceptable salt thereof, and a pharmaceutically acceptable excipient. Particularly, this invention is directed to a pharmaceutical composition for the treatment of an sGC-mediated disease or disorder, wherein the composition comprises a compound according to Formula (I), or a pharmaceutically acceptable salt thereof, and a pharmaceutically acceptable excipient.

In one embodiment, the invention is directed to a method of treating an ocular disorder caused by intraocular pressure comprising administering a safe and effective amount of a compound of Formula (I), or a pharmaceutically acceptable salt thereof, to a mammal in need thereof. Still yet further, the invention is directed to a method for reducing intraocular pressure in a mammal comprising administering a safe and effective amount of a compound of Formula (I), or a pharmaceutically acceptable salt thereof, to a mammal in need thereof. Still further, the invention is directed to a method of treating glaucoma comprising administering a safe and effective amount of a compound of Formula (I), or a pharmaceutically acceptable salt thereof, to a mammal in need thereof. Yet further, the invention is directed to a method of treating ocular hypertension comprising administering a safe and effective amount of a compound of Formula (I), or a pharmaceutically acceptable salt thereof, to a mammal in need thereof. As used herein, the term "mammal" includes, but is not limited to, humans.

In one embodiment, the invention is directed to a compound described herein, or a pharmaceutically acceptable salt thereof, for use in therapy. This invention provides a compound of Formula (I), or a pharmaceutically acceptable salt thereof, for use in therapy, specifically for use in the treatment of intraocular pressure, including, but not limited to glaucoma or ocular hypertension. Specifically, this invention provides a compound of Formula (I), or a pharmaceutically acceptable salt thereof, for use in therapy.

In one embodiment, the invention is directed to a compound described herein, or a pharmaceutically acceptable salt thereof, for use in the treatment of an ocular disease or disorder. This invention provides a compound of the invention for use in the treatment of an ocular disease or disorder, specifically, a disease or disorder recited herein. This invention provides a compound of Formula (I), or a pharmaceutically acceptable salt thereof, for use in the treatment of an ocular disorder.

In one embodiment, the invention is directed to the use of a compound of Formula (I), or a pharmaceutically acceptable salt thereof, as an active therapeutic substance. More specifically, this invention provides for the use of the compounds described herein for the treatment of an ocular disease or disorder, specifically, a disease or disorder recited herein. Accordingly, the invention provides for the use of a compound of Formula (I), or a pharmaceutically acceptable salt thereof, as an active therapeutic substance in the treatment of a human in need thereof with an ocular disease or disorder, specifically, a disease or disorder recited herein.

In one embodiment, the invention is directed to a compound described herein, or a pharmaceutically acceptable salt thereof, in the manufacture of a medicament for treatment of an ocular disease or disorder, for example the diseases and disorders recited herein. Specifically, the invention further provides for the use of a compound of Formula (I), or a pharmaceutically acceptable salt thereof, in the manufacture of a medicament for use in the treatment of an ocular disease or disorder, for example the diseases and disorders recited herein.

DETAILED DESCRIPTION OF THE INVENTION

The invention relates to activators of soluble guanylate cyclase (sGC) and their use in pharmaceutical compositions for the reduction of IOP. In particular, the invention relates to a compound of Formula (I):

(I)

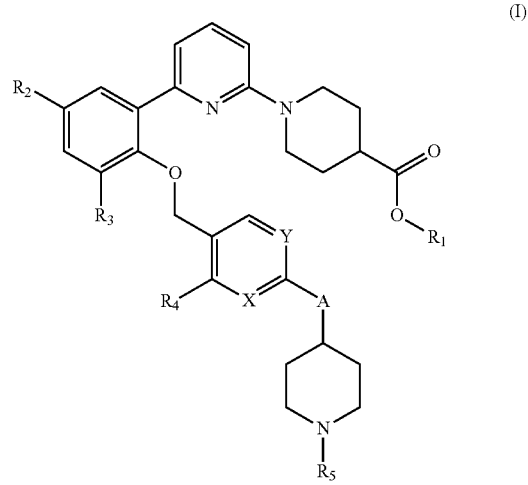

or a pharmaceutically acceptable salt thereof, wherein:

$R_1$ is selected from H and —$C_{1-3}$alkyl;

$R_2$ and $R_3$ are each independently selected from H and halogen;

$R_4$ is selected from H, —$C_{1-3}$alkyl, —O—$C_{1-3}$alkyl, —O—$C_{3-4}$cycloalkyl, —O—$(CH_2)_p$-oxetanyl, and —O—$(CH_2)_p$-tetrahydrofuranyl;

X and Y are each CH; or if X is N, then Y is CH; or if Y is N then X is CH;

A is absent or O;

$R_5$ is selected from —$C_{1-4}$ alkyl, —$C_{3-4}$ cycloalkyl, —$(CH_2)_n$CN, —$(CH_2)_n$CF$_3$, —$(CH_2)_m$-tetrahydrofuranyl, —$(CH_2)_m$-oxetanyl, —$C_{2-5}$ alkyl-OH, —$C_{2-5}$ alkyl-OCH$_3$ and —CO—$R_6$;

$R_6$ is selected from —$C_{1-6}$ alkyl and —$C_{3-6}$ cycloalkyl, optionally substituted by —OH, —OCH$_3$, —CN, COOH or —F, or $R_6$ is —$(CH_2)_m$-tetrahydrofuranyl or —$(CH_2)_m$-oxetanyl, or R6 is a $(CH_2)_m$-4 to 5-membered heterocycle;

n is 1 or 2;

m is 0 or 1; and p is 0 or 1.

Suitably, $R_1$ is H. Suitably, $R_1$ is —$C_{1-3}$alkyl. In one embodiment, $R_1$ is —CH$_3$. In one embodiment, $R_1$ is —CH$_2$—CH$_3$. In one embodiment $R_1$ is —CH$_2$—CH$_2$—CH$_3$. In one embodiment, $R_1$ is isopropyl.

Suitably, $R_2$ and $R_3$ are each independently selected from H and halogen.

In one embodiment of the invention, $R_2$ and $R_3$ are both H.

In one embodiment of the invention, $R_2$ and $R_3$ are both halogen.

In one embodiment of the invention, one of $R_2$ or $R_3$ is hydrogen and the other is halogen.

Suitably, the halogen is selected from chlorine, fluorine, bromine and iodine. In one embodiment of the invention, halogen is selected from chlorine and fluorine. In one embodiment of the invention, halogen is fluorine. In one embodiment of the invention, halogen is chlorine.

Suitably, $R_4$ is selected from H, —$C_{1-3}$alkyl, —O—$C_{1-3}$alkyl, —O—$C_{3-4}$cycloalkyl, —O—$(CH_2)_p$-oxetanyl, and —O—$(CH_2)_p$-tetrahydrofuranyl.

Suitably, $R_4$ is —$C_{1-3}$alkyl. In one embodiment of the invention, $R_4$ is —CH$_3$. In one embodiment, $R_4$ is —CH$_2$—CH$_3$. In one embodiment $R_4$ is —CH$_2$—CH$_2$—CH$_3$. In one embodiment, $R_4$ is isopropyl.

Suitably, $R_4$ is —O—$C_{1-3}$alkyl. In one embodiment of the invention, $R_4$ is —O—CH$_3$. In one embodiment of the invention, $R_4$ is —O—CH$_2$CH$_3$. In one embodiment of the invention, $R_4$ is —O—CH$_2$CH$_2$CH$_3$.

Suitably, $R_4$ is —O—$C_{3-4}$cycloalkyl. In one embodiment of the invention, $R_4$ is —O—$C_3$cycloalkyl. In one embodiment of the invention, $R_4$ is —O—$C_4$cycloalkyl.

Suitably, $R_4$ is —O—$(CH_2)_p$-oxetanyl. In one embodiment, $R_4$ is —O-oxetanyl. In one embodiment, $R_4$ is —O—CH$_2$-oxetanyl.

Suitably, $R_4$ is —O—$(CH_2)_p$-tetrahydrofuranyl. In one embodiment, $R_4$ is —O-tetrahydrofuranyl. In one embodiment of the invention, $R_4$ is —O—CH$_2$-tetrahydrofuranyl.

Suitably, X and Y are each CH.

Suitably, if X is N, then Y is CH.

Suitably, if Y is N then X is CH.

Suitably, A is absent or Oxygen.

In one embodiment, A is absent.

In one embodiment, A is Oxygen.

Suitably, $R_5$ is selected from —$C_{1-4}$ alkyl, —$C_{3-4}$ cycloalkyl, —$(CH_2)_n$CN, —$(CH_2)_n$CF$_3$, —$(CH_2)_m$-tetrahydrofuranyl, —$(CH_2)_m$-oxetanyl, —$C_{2-5}$ alkyl-OH, —$C_{2-5}$ alkyl-OCH$_3$ and —CO—$R_6$;

Suitably, $R_5$ is —$C_{1-4}$alkyl. In one embodiment of the invention, $R_5$ is —CH$_3$. In one embodiment, $R_5$ is —CH$_2$—CH$_3$. In one embodiment $R_5$ is —CH$_2$—CH$_2$—CH$_3$. In one embodiment, $R_5$ is isopropyl.

Suitably, $R_5$ is —$C_{3-4}$cycloalkyl. In one embodiment of the invention, $R_4$ is —$C_3$cycloalkyl. In one embodiment of the invention, $R_4$ is —$C_4$cycloalkyl.

Suitably, $R_5$ is selected from —$(CH_2)_n$CN. In one embodiment of the invention, $R_5$ is —CH$_2$—CN. In one embodiment of the invention, $R_5$ is —CH$_2$—CH$_2$—CN.

Suitably, $R_5$ is —$(CH_2)_n$CF$_3$. In one embodiment of the invention, $R_5$ is —CH$_2$CF$_3$. In one embodiment of the invention, $R_5$ is —CH$_2$—CH$_2$—CF$_3$.

Suitably, $R_5$ is —$(CH_2)_m$-tetrahydrofuranyl. In one embodiment of the invention, $R_5$ is -tetrahydrofuranyl. In one embodiment of the invention, $R_5$ is —CH$_2$-tetrahydrofuranyl.

Suitably, $R_5$ is —$(CH_2)_m$-oxetanyl. In one embodiment of the invention, $R_5$ is -oxetanyl. In one embodiment of the invention, $R_5$ is —CH$_2$-oxetanyl.

Suitably, $R_5$ is —$C_{2-5}$alkyl-OH. In one embodiment of the invention, $R_5$ is —CH$_2$—CH$_2$—OH. In one embodiment of the invention, $R_5$ is —CH$_2$—CH$_2$—CH$_2$—OH. In one embodiment of the invention, $R_5$ is —CH$_2$—(CH$_2$)$_2$—OH. In one embodiment of the invention, $R_5$ is —(CH$_2$)$_4$—OH. In one embodiment of the invention, $R_5$ is —CH$_2$(CH$_2$)$_3$—OH. In one embodiment of the invention, $R_5$ is —(CH$_2$)$_5$—OH. In one embodiment if the invention, $R_5$ is —(CH$_2$)$_2$—(CH$_2$)$_3$—OH.

In one embodiment of the invention, $R_5$ is —CO—$R_6$.

Suitably, $R_6$ is selected from —$C_{1-6}$ alkyl and —$C_{3-6}$ cycloalkyl, optionally substituted by —OH, —OCH$_3$, —CN, COOH or —F, or $R_6$ is —$(CH_2)_m$-tetrahydrofuranyl or —$(CH_2)_m$-oxetanyl, or $R_6$ is a $(CH_2)_m$-5-membered heterocycle.

Suitably, $R_6$ is —$C_{1-6}$ alkyl.

Suitably, $R_6$ —$C_{3-6}$ cycloalkyl.

Suitably, $R_6$ is —$(CH_2)_m$-tetrahydrofuranyl or —$(CH_2)_m$-oxetanyl.

In one embodiment of the invention, $R_6$ is —$(CH_2)_m$-oxetanyl.

In one embodiment of the invention, $R_6$ is —$(CH_2)_m$-tetrahydrofuranyl.

If $R_6$ is —$C_{1-6}$ alkyl or —$C_{3-6}$ cycloalkyl, each of these can be optionally substituted by —OH, —OCH$_3$, —CN, —COOH or —F.

Suitably, $R_6$ is a —$(CH_2)_m$-5-membered heterocycle.

Suitably, n is 1. Suitably, n is 2.

Suitably, m is 0. Suitably, m is 1.

Suitably, p is 0. Suitably, p is 1.

In one aspect, the present invention is a compound, or a pharmaceutically acceptable salt thereof, which is described herein:

1-(6-(2-((4-(1-(cyanomethyl)piperidin-4-yl)-2-methylbenzyl)oxy)-3,5-difluorophenyl)pyridin-2-yl)piperidine-4-carboxylic acid;

1-(6-(3,5-difluoro-2-((2-methyl-4-(1-(2,2,2-trifluoroethyl)piperidin-4-yl)benzyl)oxy)phenyl)pyridin-2yl)piperidine-4-carboxylic acid;

1-(6-(3,5-difluoro-2-((2-methyl-4-(1-(oxetane-3-carbonyl)piperidin-4-yl)benzyl)oxy)phenyl)pyridin-2yl)piperidine-4-carboxylic acid;

1-(6-(3,5-difluoro-2-((4-methyl-6-(1-(2,2,2-trifluoroethyl) piperidin-4-yl)pyridin-3-yl)methoxy)phenyl)pyridin-2-yl)piperidine-4-carboxylic acid;

1-(6-(2-((6-(1-(cyanomethyl)piperidin-4-yl)-4-methylpyridin-3-yl)methoxy)-3,5-difluorophenyl)pyridin-2-yl)piperidine-4-carboxylic acid;

1-(6-(3,5-difluoro-2-((2-methyl-6-(1-(2,2,2-trifluoroethyl) piperidin-4-yl)pyridin-3-yl)methoxy)phenyl)pyridin-2-yl)piperidine-4-carboxylic acid;

1-(6-(3,5-difluoro-2-((2-methyl-6-(1-(oxetan-3-yl)piperidin-4-yl)pyridin-3-yl)methoxy)phenyl)pyridin-2-yl)piperidine-4-carboxylic acid;

1-(6-(3,5-difluoro-2-((2-methyl-6-(1-(tetrahydrofuran-3-yl) piperidin-4-yl)pyridin-3-yl)methoxy)phenyl)pyridin-2-yl)piperidine-4-carboxylic acid;

1-(6-(3,5-difluoro-2-((2-methyl-6-(1-((tetrahydrofuran-3-yl)methyl)piperidin-4-yl)pyridin-3-yl)methoxy)phenyl) pyridin-2-yl)piperidine-4-carboxylic acid;

1-(6-(2-((6-(1-(cyanomethyl)piperidin-4-yl)-2-methylpyridin-3-yl)methoxy)-3,5-difluorophenyl)pyridin-2-yl)piperidine-4-carboxylic acid, Sodium salt;

1-(6-(3,5-difluoro-2-((2-methyl-6-(1-(oxetane-3-carbonyl) piperidin-4-yl)pyridin-3-yl)methoxy)phenyl)pyridin-2-yl)piperidine-4-carboxylic acid, Sodium salt;

1-(6-(3,5-difluoro-2-((6-(1-(2-hydroxyacetyl)piperidin-4-yl)-2-methylpyridin-3-yl)methoxy)phenyl)pyridin-2-yl) piperidine-4-carboxylic acid, Sodium salt;

1-(6-(3-chloro-2-((2-methyl-4-(1-(oxetan-3-yl)piperidin-4-yl)benzyl)oxy)phenyl)pyridin-2-yl)piperidine-4-carboxylic acid, Sodium salt;

1-(6-(3,5-difluoro-2-((2-methyl-4-(1-(oxetan-3-yl)piperidin-4-yl)benzyl)oxy)phenyl)pyridin-2-yl)piperidine-4-carboxylic acid, Sodium salt;

1-(6-(3,5-difluoro-2-((2-methyl-4-(1-(tetrahydrofuran-3-yl) piperidin-4-yl)benzyl)oxy)phenyl)pyridin-2-yl)piperidine-4-carboxylic acid, Sodium salt;

1-(6-(2-((4-(1-cyclopropylpiperidin-4-yl)-2-methylbenzyl) oxy)-3,5-difluorophenyl)pyridin-2-yl)piperidine-4-carboxylic acid, Sodium salt;

1-(6-(3,5-difluoro-2-((4-(1-(2-methoxyethyl)piperidin-4-yl)-2-methylbenzyl)oxy)phenyl)pyridin-2-yl)piperidine-4-carboxylic acid, Sodium salt;

1-(6-(3,5-difluoro-2-((4-(1-(2-hydroxyethyl)piperidin-4-yl)-2-methylbenzyl)oxy)phenyl)pyridin-2-yl)piperidine-4-carboxylic acid, Sodium salt;

1-(6-(3,5-difluoro-2-((2-methyl-4-(1-(3,3,3-trifluoropropyl) piperidin-4-yl)benzyl)oxy)phenyl)pyridin-2-yl)piperidine-4-carboxylic acid, Sodium salt;

1-(6-(3,5-difluoro-2-((4-(1-(2-hydroxyacetyl)piperidin-4-yl)-2-methylbenzyl)oxy)phenyl)pyridin-2-yl)piperidine-4-carboxylic acid, Sodium salt;

1-(6-(3,5-difluoro-2-((4-(1-(2-methoxyacetyl)piperidin-4-yl)-2-methylbenzyl)oxy)phenyl)pyridin-2-yl)piperidine-4-carboxylic acid, Sodium salt;

1-(6-(2-((4-(1-(2-cyanoacetyl)piperidin-4-yl)-2-methylbenzyl)oxy)-3,5-difluorophenyl)pyridin-2-yl)piperidine-4-carboxylic acid, Sodium salt;

1-(6-(2-((4-(1-(2-cyclopropylacetyl)piperidin-4-yl)-2-methylbenzyl)oxy)-3,5-difluorophenyl)pyridin-2-yl)piperidine-4-carboxylic acid, Sodium salt;

1-(6-(3,5-difluoro-2-((2-methyl-4-(1-(tetrahydrofuran-3-carbonyl)piperidin-4-yl)benzyl)oxy)phenyl)pyridin-2-yl) piperidine-4-carboxylic acid, Sodium salt;

(S)-1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid, Sodium salt;

(R)-1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid, Sodium salt;

1-(6-(3,5-difluoro-2-((2-methyl-4-(1-(2-(oxetan-3-yl) acetyl)piperidin-4-yl)benzyl)oxy)phenyl)pyridin-2-yl)piperidine-4-carboxylic acid, Sodium salt;

1-(6-(3,5-difluoro-2-((2-methyl-4-(1-(2-(tetrahydrofuran-3-yl)acetyl)piperidin-4-yl)benzyl)oxy)phenyl)pyridin-2-yl) piperidine-4-carboxylic acid, Sodium salt;

1-(6-(2-((4-(1-(2-carboxyacetyl)piperidin-4-yl)-2-methylbenzyl)oxy)-3,5-difluorophenyl)pyridin-2-yl)piperidine-4-carboxylic acid, di-Sodium salt;

1-(6-(2-((4-(1-(2-(1H-1,2,4-triazol-1-yl)acetyl)piperidin-4-yl)-2-methylbenzyl)oxy)-3,5-difluorophenyl)pyridin-2-yl)piperidine-4-carboxylic acid, Sodium salt;

1-(6-(3,5-difluoro-2-((2-methoxy-4-(1-(2,2,2-trifluoroethyl) piperidin-4-yl)benzyl)oxy)phenyl)pyridin-2-yl)piperidine-4-carboxylic acid, Sodium salt;

1-(6-(3,5-difluoro-2-((2-(oxetan-3-yloxy)-4-(1-(2,2,2-trifluoroethyl)piperidin-4-yl)benzyl)oxy)phenyl)pyridin-2-yl)piperidine-4-carboxylic acid, Sodium salt; or 1-(6-(3, 5-difluoro-2-((2-methyl-4-((1-(2,2,2-trifluoroethyl) piperidin-4-yl)oxy)benzyl)oxy)phenyl)pyridin-2-yl) piperidine-4-carboxylic acid, Sodium salt.

The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions. The compounds of the invention are only those which are contemplated to be "chemically stable" as will be appreciated by those skilled in the art.

As used herein, the terms "a compound" or "the compound" refer to one or more compounds of the present invention, particularly, compounds of Formula (I), as defined herein, in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemihydrates)), and mixtures of various forms. The skilled artisan will appreciate that pharmaceutically acceptable solvates may be formed for crystalline compounds wherein solvent molecules are incorporated into the crystalline lattice during crystallization. Solvates may involve non-aqueous solvents such as ethanol, isopropanol, DMSO, acetic acid, ethanolamine, and ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The present invention includes all such solvates and forms.

The present invention includes compounds as well as their pharmaceutically acceptable salts. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination). The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, allergic response, or other problem or complication, commensurate with a reasonable benefit/risk ratio. The skilled artisan will appreciate that pharmaceutically acceptable salts of compounds according to formula (I) may be prepared. These pharmaceutically acceptable salts may be prepared in situ during the final isolation and purification of the compound, or by separately reacting with the purified compound in its free acid or free base form with a suitable base or acid, respectively.

Compounds of the present invention can form pharmaceutically acceptable salts by reaction with a suitable base. Suitable bases include, for example, hydroxides, carbonates, hydrides, and alkoxides including NaOH, KOH, $Na_2CO_3$, $K_2CO_3$, NaH, potassium-t-butoxide, ammonium salts, and Trometamol which is a tris-salt as trishydroxymethyllaminomethane or 2-amino-2-hydroxymethyl-1,3-propanediol.

In one embodiment, the pharmaceutically acceptable salt is the sodium salt.

In a further aspect, the invention provides a method of treating a disease comprising administering the compound of the present invention or a pharmaceutically acceptable salt thereof to a patient in need thereof, wherein the disease is a result of increased IOP, for example glaucoma or ocular hypertension.

"Alkyl" refers to a saturated, straight or branched hydrocarbon group having the specified number of carbon atoms. The term "$(C_1-C_3)$alkyl" refers to an alkyl moiety containing from 1 to 3 carbon atoms. The term "$(C_1-C_4)$alkyl" refers to an alkyl moiety containing from 1 to 4 carbon atoms. The term "(C1-C6)alkyl" refers to an alkyl moiety containing from 1 to 6 carbon atoms. Exemplary alkyls include, but are not limited to methyl, ethyl, n-propyl, isopropyl, n-butyl, isobutyl, s-butyl, t-butyl, n-pentyl, isopentyl, neopentyl, n-hexyl, isohexyl and neohexyl.

A carbocyclic group is a cyclic group in which all of the ring members are carbon atoms, which may be saturated, partially unsaturated (non-aromatic) or fully unsaturated (aromatic). The term "carbocyclic" includes cycloalkyl and aryl groups.

"Cycloalkyl" refers to a non-aromatic, saturated, cyclic hydrocarbon group containing the specified number of carbon atoms. The term "$(C_3-C_4)$cycloalkyl" refers to a non-aromatic cyclic hydrocarbon ring having from three to four ring carbon atoms. The term "$(C_3-C_6)$cycloalkyl" refers to a non-aromatic cyclic hydrocarbon ring having from three to six ring carbon atoms. Exemplary "$(C_3-C_4)$cycloalkyl" groups include cyclopropyl and cyclobutyl. Exemplary "$(C_3-C_6)$cycloalkyl" groups include cyclopropyl, cyclobutyl, cyclopentyl, and cyclohexyl.

The terms "halogen" and "halo" refer to chloro, fluoro, bromo, or iodo substituents. "Oxo" represents a double-bonded oxygen moiety; for example, if attached directly to a carbon atom forms a carbonyl moiety (—C=O). "Hydroxy" or "hydroxyl" is intended to mean the radical —OH. As used herein, the term "cyano" refers to the group —CN.

As used herein, the terms "heterocycle" or "heterocyclic group" are used interchangeably to refer to a cyclic group having, as ring members, atoms of at least two different elements, for example, selected from carbon and one or more of nitrogen, oxygen or sulfur, which cyclic group may be saturated, partially unsaturated (non-aromatic) or fully unsaturated (aromatic). Suitably, the heterocycle is a 4 to 5-membered heterocyclic group. In one embodiment of the invention, the heterocyclic group is a triazole.

As used herein, the term "optionally substituted" indicates that a group (such as an alkyl, cycloalkyl, alkoxy, heterocycloalkyl, aryl, or heteroaryl group) or ring or moiety (such as a carbocyclic or heterocyclic ring or moiety) may be unsubstituted, or the group, ring or moiety may be substituted with one or more substituent(s) as defined. In the case where groups may be selected from a number of alternative groups, the selected groups may be the same or different.

The term "independently" means that where more than one substituent is selected from a number of possible substituents, those substituents may be the same or different.

A therapeutically "effective amount" is intended to mean that amount of a compound that, when administered to a patient in need of such treatment, is sufficient to effect treatment, as defined herein. Thus, e.g., a therapeutically effective amount of a compound of Formula (I), or a pharmaceutically acceptable salt thereof, is a quantity of an inventive agent that, when administered to a human in need thereof, is sufficient to modulate and/or inhibit the activity of sGC such that a disease condition which is mediated by that activity is reduced, alleviated or prevented. The amount of a given compound that will correspond to such an amount will vary depending upon factors such as the particular compound (e.g., the potency ($pIC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmacokinetic properties), disease or disorder and its severity and the specific composition and method being used, but can nevertheless be determined by one of skill in the art.

"Treating" or "treatment" is intended to mean at least the mitigation of a disease or disorder in a patient. The methods of treatment for mitigation of a disease or disorder include the use of the compounds in this invention in any conventionally acceptable manner, for example for prevention, retardation, prophylaxis, therapy or cure of an sGC-mediated disease or disorder, as described hereinabove.

Compounds, for example agents activating sGC as disclosed herein, can be used as a medicament or used to formulate a pharmaceutical composition with one or more of the utilities disclosed herein. They can be administered in vitro to cells in culture, in vivo to cells in the body, or ex vivo to cells outside of an individual that can later be returned to the body of the same individual or another. Such cells can be disaggregated or provided as solid tissue.

Compounds, for example agents activating sGC as disclosed herein can be used to produce a medicament or other pharmaceutical compositions. Use of agents activating sGC which further comprise a pharmaceutically acceptable carrier and compositions which further comprise components useful for delivering the composition to an individual are known in the art. Addition of such carriers and other components to the agents as disclosed herein is well within the level of skill in this art. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

In addition to the active compound, such compositions can contain pharmaceutically-acceptable carriers and other ingredients known to facilitate administration and/or enhance uptake (e.g., saline, dimethyl sulfoxide, lipid, polymer, affinity-based cell specific-targeting systems). The composition can be incorporated in a gel, sponge, or other permeable matrix (e.g., formed as pellets or a disk) and placed in proximity to the endothelium for sustained, local release. The composition can be administered in a single dose or in multiple doses which are administered at different time intervals.

The compounds of this invention can be administered as topical eye drops. The compounds of this invention can be administered via sub-conjunctival, intracameral or intravitreal routes which would necessitate administration intervals that are longer than daily.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

The pharmaceutical compositions of the invention are prepared using techniques and methods known to those skilled in the art. Some of the methods commonly used in the art are described in *Remington's Pharmaceutical Sciences* (Mack Publishing Company). Accordingly, another embodiment of this invention is a method of preparing a pharmaceutical composition comprising the step of admixing a compound of Formula (I) with one or more pharmaceutically acceptable excipients.

Treatment of the diseases or disorders described herein can be achieved using a compound of this invention as a monotherapy, or in dual or multiple combination therapy. The compounds of Formula (I) and pharmaceutically acceptable salts thereof may be employed alone or in combination with other therapeutic agents. Combination therapies according to the present invention thus comprise the administration of at least one compound of Formula (I) or a pharmaceutically acceptable salt thereof, and at least one other therapeutically active agent. Preferably, combination therapies according to the present invention comprise the administration of a compound of Formula (I) or a pharmaceutically acceptable salt thereof, and at least one other therapeutically active agent. The compound of Formulas (I) and pharmaceutically acceptable salts thereof, and the other therapeutically active agent(s) may be administered together in a single pharmaceutical composition or separately and, when administered separately this may occur simultaneously or sequentially in any order. The amounts of the compound of Formulas (I) and a pharmaceutically acceptable salt thereof, and the other therapeutically active agent(s) and the relative timings of administration will be selected in order to achieve the desired combined therapeutic effect.

In the context of this invention, combination therapies would include other IOP-lowering drugs, for example prostaglandin analogs (e.g., latanoprost, bimatoprost, travoprost, tafluprost); beta-adrenergic blockers (e.g., timolol, betaxolol, levobunolol); alpha-adrenergic agonists (e.g., brimonidine, paraamino-clonidine); parasympathomimetics (e.g. pilocarpine, carbachol, acetylcholineesterase inhibitors); sympathomimetics (e.g., epinephrine, dipivalyl-epinephrine); and carbonic anhydrase inhibitors (e.g., dorzolamide, brinzolamide). In one embodiment, a compound of this invention is administered in combination with a prostaglandin analog (e.g., latanoprost, bimatoprost, travoprost, or tafluprost). In another embodiment, a compound of this invention is administered in combination with a beta-adrenergic blocker (e.g., timolol, betaxolol, levobunolol). In yet another embodiment, a compound of this invention is administered in combination with an alpha-adrenergic agonist (e.g., brimonidine, paraamino-clonidine). In still yet another embodiment, a compound of this invention is administered in combination with a carbonic anhydrase inhibitor (e.g., dorzolamide, brinzolamide).

Pharmaceutical formulations adapted for topical administration may be formulated as ointments, creams, emulsions, suspensions, lotions, powders, solutions, pastes, gels, sprays, aerosols or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent. Formulations to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Formulations for drug delivery using ocular devices may combine one or more active agents and adjuvants appropriate for the indicated route of administration. For example, the active agents may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers, and a carrier or diluent that has a time delay property. Representative examples of biodegradable compositions can include albumin, gelatin, starch, cellulose, dextrans, polysaccharides, poly (D,L-lactide), poly (D,L-lactide-co-glycolide), poly (glycolide), poly (hydroxybutyrate), poly (alkylcarbonate) and poly (orthoesters) and mixtures thereof. Representative examples of non-biodegradable polymers can include EVA copolymers, silicone rubber and poly (methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) Adv. Drug Deliv. Rev. 3;57:1595-639, herein incorporated by reference for purposes of its teachings of examples of polymers for use in ocular drug delivery.

In describing the invention, chemical elements are identified in accordance with the Periodic Table of the Elements. Abbreviations and symbols utilized herein are in accordance with the common usage of such abbreviations and symbols by those skilled in the chemical and biological arts. Specifically, the following abbreviations may be used in the examples and throughout the specification:

| g (grams) | mg (milligrams) | Rt (retention time) |
|---|---|---|
| L (liters) | mL or ml (milliliters) | EtOH (ethanol) |
| μL (microliters) | psi (pounds per square inch) | EtOAc (ethyl acetate) |
| M (molar) | mM (millimolar) | |
| mol (moles) | mmol (millimoles) | |
| RT (room temperature) | MeOH (methanol) | |
| i-PrOH (isopropanol) | TEA (triethylamine) | |
| TFA (trifluoroacetic acid) | TFAA (trifluoroacetic anhydride) | |
| THF (tetrahydrofuran) | DMSO (dimethylsulfoxide) | |
| HATU = O-(7-Azabenzotriazol-1-yl)-N,N,N',N'-tetramethyluronium hexafluorophosphate | | |

The reactions described herein are applicable for producing compounds of the invention having a variety of different substituent groups (e.g., $R^1$, $R^2$, etc.), as defined herein. The skilled artisan will appreciate that if a particular substituent is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999).

One of skill in the art would understand that in Scheme 1 the precursor 8 to the compound of formula (I) is also a compound that falls within the scope of the invention as defined in the claims.

Schemes

The following schemes illustrate how compounds of the present invention can be prepared. The specific solvents and reaction conditions referred to are also illustrative and are not intended to be limiting. Compounds not described are either commercially available or are readily prepared by one skilled in the art using available starting materials.

Schemes 1 to 6 represent general schemes for the preparation of compounds according to formula (I) wherein A is absent and scheme 7 represents a general scheme for the preparation of compounds of formula (I) wherein A is oxygen.

Scheme 1

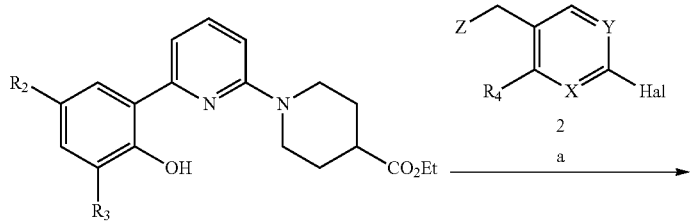

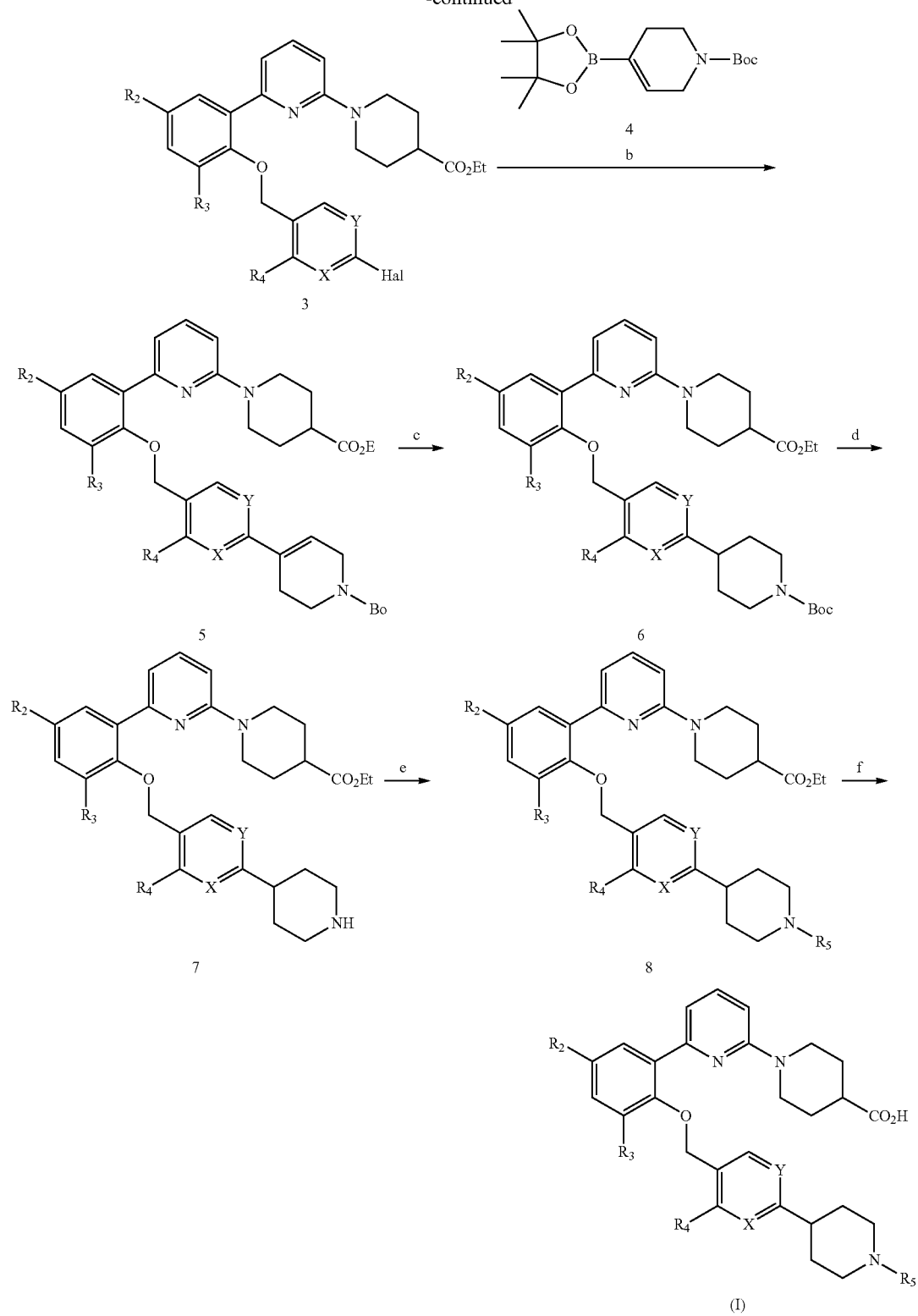

Conditions: (a) for X = Y = CH, Z = Br, Hal = Br: $Cs_2CO_3$, acetone, reflux; X or Y = N, Z = OH, Hal = Cl: DEAD, $PPh_3$, THF, 0° C. to Rt; b) $PdCl_2(PPh_3)_2$, $Na_2CO_3$, DME/H2O, 100° C.; c) $H_2$, $PtO_2$, EtOAc; d) TFA, $CH_2Cl_2$, 0° C.; e)$R_5$—LG*,$Cs_2CO_3$, acetone, 60° C.; or$R_5$—CHO, $NaCNBH_4$, AcOH, MeOH, RT to 60° C., for $R_5$ = oxetanyl or tetrahydrofuranyl: oxetan-3-one or dihydrofuran-3(2H)-one, $NaCNBH_4$, AcOH, MeOH, RT to 60° C., for $R_5$ = CO—$R_6$:$R_6$—COOH, HATU, TEA, $CH_2Cl_2$, RT; f) NaOH or LiOH, $H_2O$, ROH, RT
(*LG = halogene, OTf, OMs)

Scheme 1 represents a general scheme for the preparation of compounds according to formula (I), wherein A is absent.

The preparation of compound 1 depicted as starting material is described in WO 2009/071504A1. Compounds 2 and 4 depicted as starting material are commercially available or made from commercially available starting materials using methods known to those skilled in the art. Reaction conditions are as described above in the scheme; however, the skilled artisan will appreciate that certain modifications in the reaction conditions and/or reagents used are possible.

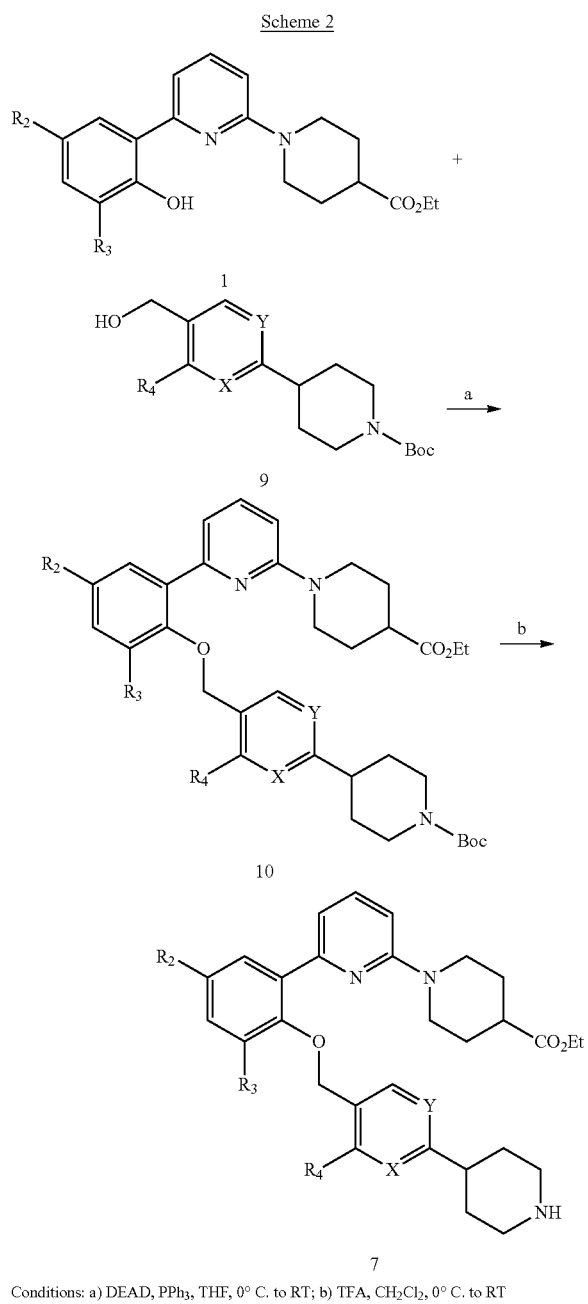

Conditions: a) DEAD, PPh₃, THF, 0° C. to RT; b) TFA, CH₂Cl₂, 0° C. to RT

Scheme 2 represents an alternate method for the preparation of intermediates 7 depicted in Scheme 1, used for the synthesis of compounds of the formula (I).

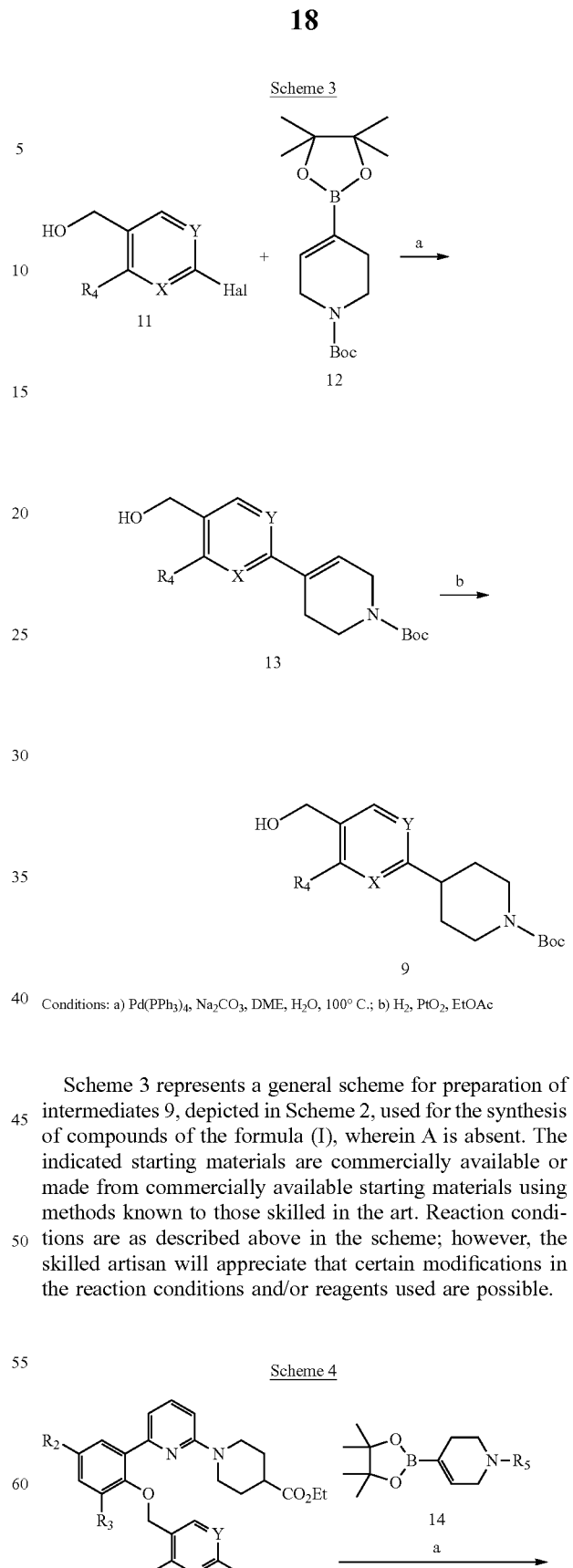

Conditions: a) Pd(PPh₃)₄, Na₂CO₃, DME, H₂O, 100° C.; b) H₂, PtO₂, EtOAc

Scheme 3 represents a general scheme for preparation of intermediates 9, depicted in Scheme 2, used for the synthesis of compounds of the formula (I), wherein A is absent. The indicated starting materials are commercially available or made from commercially available starting materials using methods known to those skilled in the art. Reaction conditions are as described above in the scheme; however, the skilled artisan will appreciate that certain modifications in the reaction conditions and/or reagents used are possible.

-continued

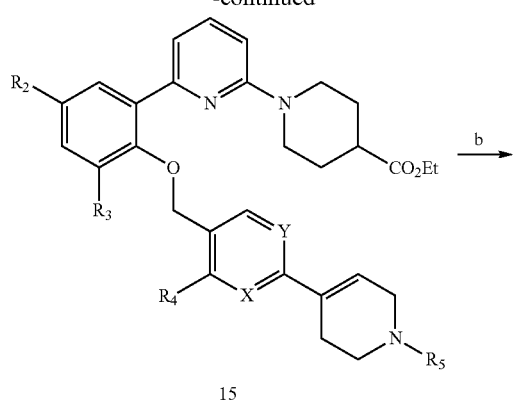

15

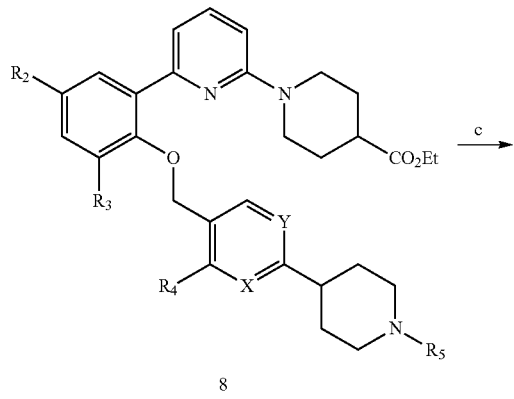

8

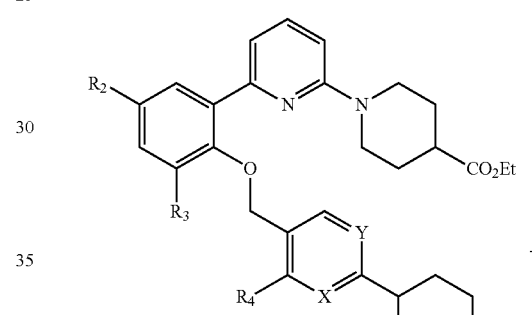

(I)

Conditions: a) Pd(PPh₃)₄, Na₂CO₃, DME/H₂O, 100° C.; b) H₂, PtO₂, EtOAc; c) NaOH or LiOH, H₂O, ROH, RT.

Scheme 4 represents a preferred general scheme for preparation of compounds according to formula (I) wherein R₄ is selected from O—C1-3 alkyl or O—C3-4 cycloalkyl, O—(CH₂)$_p$-oxetanyl, O—(CH₂)$_p$-tetrahydrofuranyl, with p=0 or 1, and A is absent, starting from Intermediate 3 depicted in Scheme 1. Compound 14 depicted as starting material is commercially available or made from commercially available starting materials using methods known to those skilled in the art.

Scheme 5

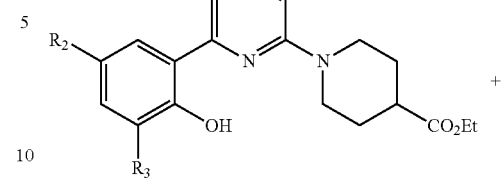

1

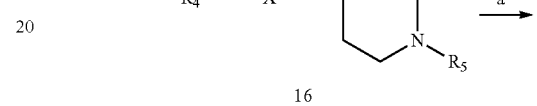

16

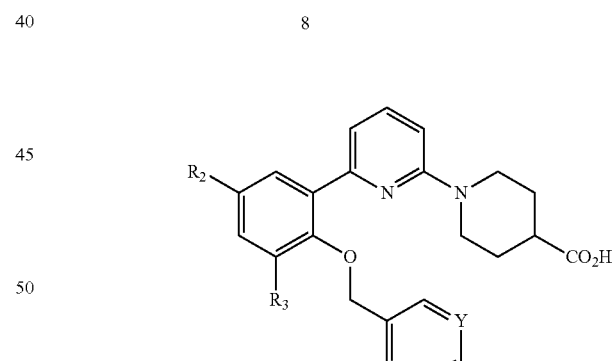

8

(I)

Conditions: a) DEAD, PPh₃, THF, 0° C. to RT; b) NaOH or LiOH, H₂O, ROH, RT.

Scheme 5 represents an alternate preferred method for preparing compounds according to formula (I) wherein R₄ is selected from —O—C1-3 alkyl or —O—C3-4 cycloalkyl, —O—(CH₂)$_p$-oxetanyl, —O—(CH₂)$_p$-tetrahydrofuranyl, wherein p is 0 or 1, and A is absent, starting from Intermediate 1 depicted in Scheme 1.

Scheme 6

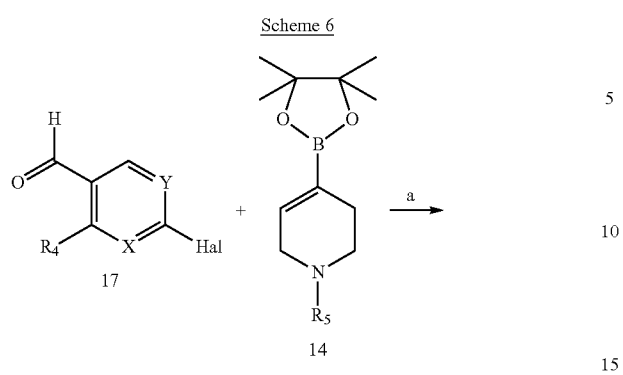

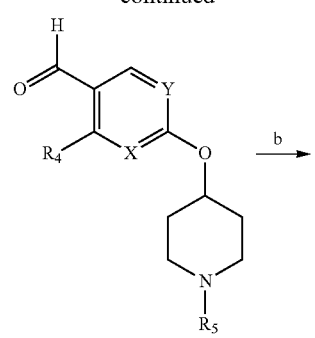

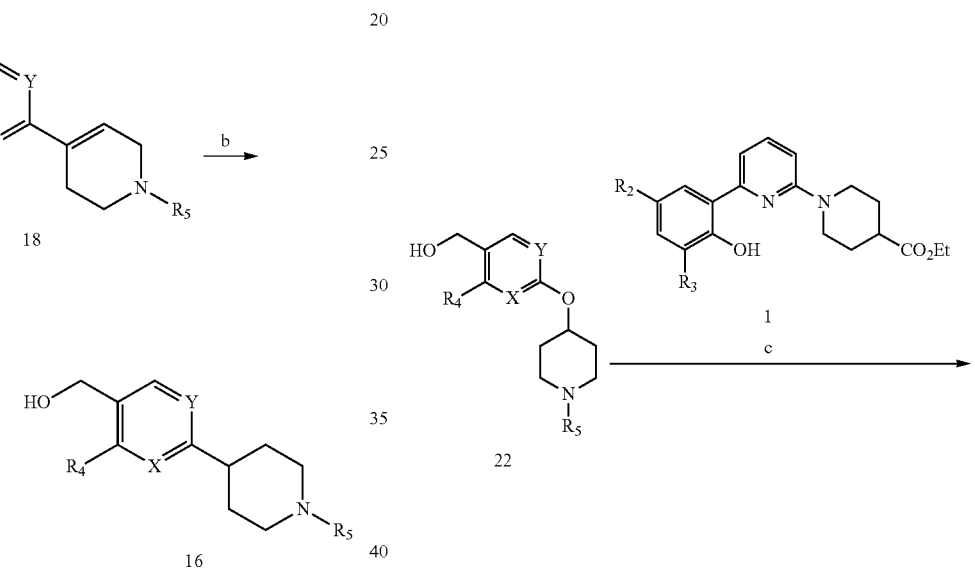

Conditions: a) Pd(PPh₃)₄, Na₂CO₃, DME/H₂O, 100° C.; b) H₂, PtO₂, EtOAc.

Scheme 6 represents a general method for preparation of Intermediate 16, depicted in Scheme 5, used for the synthesis of compounds of formula (I), wherein A is absent. The indicated starting materials are commercially available or made from commercially available starting materials using methods known to those skilled in the art. Reaction conditions are as described above in the Scheme; however, the skilled artisan will appreciate that certain modifications in the reaction conditions and/or reagents used are possible.

Scheme 7

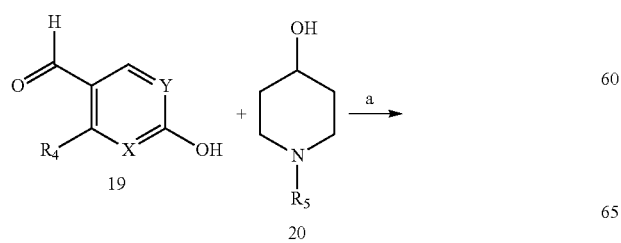

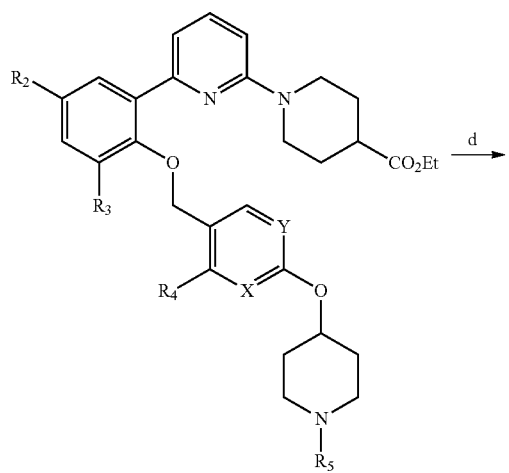

-continued

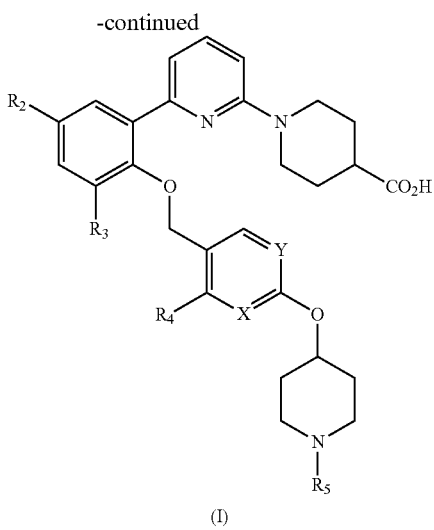

Conditons: a) ) DEAD, PPh₃, THF, 0° C. to RT;
b) NaBH₄, EtOH, 0° C. to rt; c) DEAD, PPh₃, THF, 0° C. to RT;
d) NaOH or LiOH, H₂O, ROH, RT.

Scheme 7 represents a general scheme for preparation of compounds according to formula (I) wherein A is oxygen. The indicated starting materials 19 and 20 are commercially available or made from commercially available starting materials using methods known to those skilled in the art. Reaction conditions are as described above in the Scheme; however, the skilled artisan will appreciate that certain modifications in the reaction conditions and/or reagents used are possible.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Unless otherwise noted, all starting materials were obtained from commercial suppliers and used without further purification. Unless otherwise indicated, all temperatures are expressed in °C (degrees Centigrade). Unless otherwise indicated, all reactions are conducted under an inert atmosphere at room temperature ("RT").

The compounds were purified by silica chromatography. Preparative 25 HPLC refers to methods where the material was purified by high pressure liquid chromatography. Preparative HPLC instruments used were as follows:

Prep-HPLC Instrument: Waters 2545, 2707 Auto sampler with WFC III Fraction collection
Method A: Column: X Terra C18 (250*19 mm) 10 µ Mobile Phase, A=0.1% ammonium bicarbonate (63%) and B=acetonitrile (37%); Flow rate, 18 ml/min; Sample loading 5 solvent acetonitrile+MeOH; Fraction volume 200 mL
Method B: Column: XBridge C18 (150*30 mm, 5 µ); Mobile Phase, A=0.1% formic acid in water, B=acetonitrile Gradient Time (min)/% B: 0/10, 2/10, 15/60, 18/90; Column Temp ° C.: Ambient; Flow rate, 30 ml/min, Sample loading solvent ACN+THF; Fraction volume, 150 mL
Method C: Column: Sunfire C18 (150*30 mm, 5 µ); Mobile Phase, A=0.1% formic acid in water, B=acetonitrile Gradient Time (min)/% B: 0/10, 1/10, 15/60; Column Temp ° C.: Ambient; Flow rate, 30 ml/min, Sample loading solvent ACN+methanol; Fraction volume, 150 mL
Method D: Column: XBridge C18 (150×30 mm) 5 µ; Mobile Phase A=10 mm ammonium bicarbonate; B=acetonitrile (40:60); Temp, ambient; Flow rate, 30 ml/min; Sample loading solvent, acetonitrile; Fraction volume, 150 mL
LCMS Methods:
(a) Acq. Method Conditions: RND-FA-4.5-MIN
Column: Acquity BEH C18 (50 mm×2.1 mm, 1.7 um)
Mobile Phase: A: 0.1% Formic Acid in water;
B: 0.1% Formic Acid in ACN
Time (min)/% B: 0/3, 0.4/3, 3.2/98, 3.8/98, 4.2/3, 4.5/3
Column Temp: 35° C., Flow Rate: 0.6 mL/min
(b) Acq. Method Conditions: RND-FA-7 -MIN
Column: Acquity BEH C18 (50 mm×2.1 mm, 1.7 um)
Mobile Phase: A: 0.1% Formic Acid in water;
B: 0.1% Formic Acid in ACN
Time (min)/% B: 0/3, 1.8/3, 3.8/30, 4.5/50, 5/95, 6/95,7/3
Column Temp: 35° C., Flow Rate: 0.6 ml/min
(c) Acq. Method Conditions: RND-AA-6-MIN
Column: XBridge BEH C18 (50 mm×4.6 mm, 2.5 um)
Mobile Phase: A: 5 Mm Ammonium Acetate in water; B: ACN
Time (min)/% B: 0/5, 0.5/5, 1/15, 3.3/98, 5.2/98, 5.5/5, 6/5
Column Temp: 35° C., Flow Rate: 1.3 ml/min
(d) Acq. Method Conditions: RND-AA-6-MIN
Column: Phenomenex Gemini-NX C18 (50 mm×4.6 mm, 3.0 µm)
Mobile Phase: A: 5 Mm Ammonium Acetate in water; B: ACN
Time (min)/% B: 0/5, 0.5/5, 1/15, 3.3/98, 5.2/98, 5.5/5, 6/5
Column Temp: 35° C., Flow Rate: 1.3 ml/min
(e) Acq. Method Conditions: RND-ABC-6-MIN
Column: Xbridge C18 (50 mm×4.6 mm, 2.5 µm)
Mobile Phase: A: 5 mM Ammonium Bicarbonate in water (pH-10);B: ACN
Time (min)/% ACN: 0/5,0.5/5,1/15,3.3/98,5.2/98,5.5/5, 6.05/5
Column temp: 35° C., Flow Rate1.3 ml/min
(f) Acq. Method Conditions: RND-ABC-6.5-MIN
Column: XBridge BEH C18 (50 mm×4.6 mm, 2.5 µm)
Mobile Phase: A: 5 mM Ammonium Bicarbonate in water(pH-10), B: 100% ACN
Gradient: Time (min)/% B: 0/5, 0.5/5, 1/15, 3.3/98, 6.0/98, 6.1/5, 6.5/5
Column Temp: 35° C., Flow Rate: 1.3 ml/min
(g) Acq. Method Conditions: RND-AA-10-MIN
Column: X-SELECT CSH C18 (150 mm×3 mm, 2.5 µm)
Mobile Phase: A: 5 mM Ammonium acetate in water; B: ACN
Gradient: Time (min)/% B: 0/3, 1/3, 4/98, 9/98, 9.5/3, 10/3
Column Temp: 35° C., Flow Rate: 0.6 ml/min
(h) Acq. Method Conditions: RND-ABC-5-MIN
Column: ACQUITY BEH-C18 (50 mm×2.1 mm)1.7)m
Flow Rate:-0.6 ml/min, Column temp:35° C.
Mobile Phase: A:5 mM Ammonium bicarbonate in water (pH-10); B:Acetonitrile
Gradient: Time (min)/% A: 0.01/97, 0.4/97, 3.2/2, 4.8/2, 4.9/97, 5/97

(i) Acq. Method Conditions: RND-ABC-10-MIN-V
Column: Xbridge C18 (50 mm×4.6 mm, 2.5 μm),
Mobile Phase: A: 5 mM Ammonium Bicarbonate in water (pH-10); B: ACN
Time (min)/% ACN: 0/5,0.5/5,1/15,6/98,9/98,9.5/5,10/5
Column temp: 35° C., Flow Rate1.3 ml/min
(j) Acq. Method Conditions: RND-ABC-7.5-MIN
Column: Phenomenex Gemini-NX C18 (50 mm×4.6 mm, 3.0 μm)
Mobile Phase: A: 5 mM Ammonium Bicarbonate in water(pH-10), B: 100% ACN
Gradient: Time (min)/% B: 0/5, 0.5/5, 1.5/15, 4.5/98, 6.5/98, 7/5, 7.5/5
Column Temp: 35° C., Flow Rate: 1.3 ml/min Chiral HPLC Methods:
(a) Column: YMC AMYLOSE-C(4.6*250 mm)5 um
Co-solvent: 0.5% DEA in METHANOL
Total flow: 4 g/mn
% of Co-Solvent: 40%
Temperature: 30° c
ABPR: 100 bar
UV: 215 nm
(b) Column: Chiralpak ADH(4.6*250)mm5 u
Co-solvent: 0.5% DEA in METHANOL
Total flow: 4 g/mn
% of Co-Solvent: 40%
Temperature: 29.9° c
ABPR: 100 bar
UV: 215 nm
(c) Column: Chiralpak ADH(4.6*250)mm5 u
Co-solvent: 0.5% DEA in METHANOL
Total flow: 3 g/mn
% of Co-Solvent: 40%
Temperature: 29.9° c
ABPR: 100 bar
UV: 215 nm For the compounds of the Examples, in the reporting of Proton Magnetic Resonance spectral data, chemical shifts are reported in ppm (δ) using tetramethylsilane as the internal standard. Splitting patterns are designed as s, singlet; d, doublet; t, triplet; q, quartet; m, multiplet.

All NMR experiments were recorded in 400 MHz Varian instrument. Solvents used to record NMR experiments are DMSO-$d_6$ (Cambridge Isotope Laboratories, CIL) & $CDCl_3$ (CIL) TMS was used as internal standard. All results were interpreted using VNMRJ 3.2 version.

Intermediate 1: ethyl 1-(6-(2-((4-bromo-2-methylbenzyl)oxy)-3,5-difluorophenyl)pyridin-2-yl)piperidine-4-carboxylate

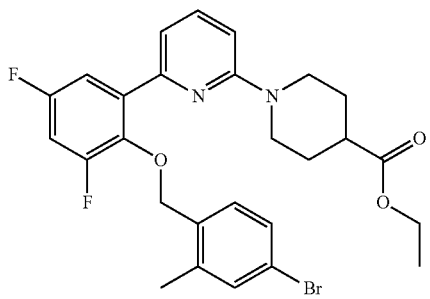 [SMILES: CCOC(=O)C1CCN(c2cccc(-c3cc(F)cc(F)c3OCc3ccc(Br)cc3C)n2)CC1]

To a solution of ethyl 1-(6-(3,5-difluoro-2-hydroxyphenyl)pyridin-2-yl)piperidine-4-carboxylate (5 g, 13.80 mmol) in acetone (100 mL) were added cesium carbonate (8.99 g, 27.6 mmol) and 4-bromo-1-(bromomethyl)-2-methylbenzene (5.46 g, 20.70 mmol). The reaction mixture was stirred at 70° C. for 16 hrs, then cooled and diluted with water (100 mL). After extraction with EtOAc (3×100 mL), the organic phase was washed with brine solution (100 mL), dried over anhydrous $Na_2SO_4$ and concentrated under reduced pressure to afford the title compound (6 g, 68.0% yield).

LCMS (a): Rt: 3.48 min, M/z=545.24 $(M+H)^+$

Intermediate 2: tert-butyl 4-(4-((2-(6-(4-(ethoxycarbonyl)piperidin-1-yl)pyridin-2-yl)-4,6-difluorophenoxy)methyl)-3-methylphenyl)-5,6-dihydropyridine-1(2H)-carboxylate

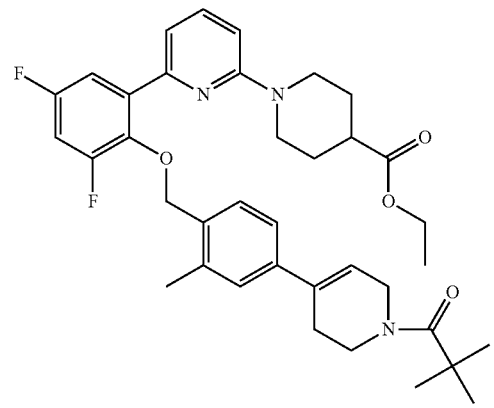 [SMILES: CCOC(=O)C1CCN(c2cccc(-c3cc(F)cc(F)c3OCc3ccc(C4=CCN(C(=O)C(C)(C)C)CC4)cc3C)n2)CC1]

To a solution of ethyl 1-(6-(2-((4-bromo-2-methylbenzyl)oxy)-3,5-difluorophenyl)pyridin-2-yl)piperidine-4-carboxylate (1 g, 1.833 mmol), tert-butyl 4-(4,4,5,5-tetramethyl-1,3,2-dioxaborolan-2-yl)-5,6-dihydropyridine-1(2H)-carboxylate (0.850 g, 2.75 mmol) and $Na_2CO_3$ (0.389 g, 3.67 mmol) in 1,2-Dimethoxyethane (10 mL) and water (3 mL), stirred under nitrogen at room temperature, was added tetrakis(triphenylphosphine)palladium(0) (0.212 g, 0.183 mmol). The reaction mixture was stirred at 100° C. for 16 hrs, then cooled and diluted with water (10 mL). After extraction with EtOAc (3×20 mL), the organic phase was washed with a brine solution (25 mL), dried over anhydrous $Na_2SO_4$ and concentrated under reduced pressure. The residue was purified by column chromatography (15% EtOAc in Hexane as eluent) to afford the title compound (800 mg, 51.6% yield).

LCMS (a): Rt: 3.84 min, M/z=648 $(M+H)^+$

Intermediate 3: tert-butyl 4-(4-(2-(6-(4-(ethoxycarbonyl)piperidin-1-yl)pyridin-2-yl)-4,6-difluorophenoxy)methyl)-3-methylphenyl)piperidine-1-carboxylate

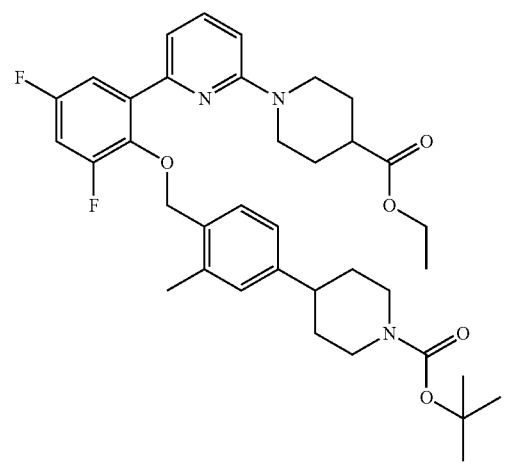 [SMILES: CCOC(=O)C1CCN(c2cccc(-c3cc(F)cc(F)c3OCc3ccc(C4CCN(C(=O)OC(C)(C)C)CC4)cc3C)n2)CC1]

To a solution of tert-butyl 4-(4-((2-(6-(4-(ethoxycarbonyl) piperidin-1-yl)pyridin-2-yl)-4,6-difluorophenoxy)methyl)-3-methylphenyl)-5,6-dihydropyridine-1(2H)-carboxylate (5 g, 7.72 mmol) in EtOAc (150 mL) was added PtO$_2$ (0.815 g, 3.86 mmol). The mixture was hydrogenated at room temperature for 16 hours and then filtered through a celite pad. The filtrate was concentrated under reduced pressure. The residue was purified by column chromatography (8-15% EtOAc: Hexane as an eluent), to afford the title compound (3 g, yield=56.9%).

LCMS (a): Rt: 3.63 min, M/z=650.59 (M+H)$^+$

Intermediate 4: ethyl 1-(6-(3,5-difluoro-2-((2-methyl-4-(piperidin-4-yl)benzyl)oxy)phenyl)pyridin-2-yl)piperidine-4-carboxylate

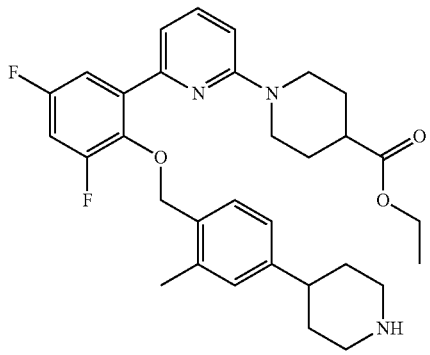 [SMILES: CCOC(=O)C1CCN(c2cccc(-c3cc(F)cc(F)c3OCc3ccc(C4CCNCC4)cc3C)n2)CC1]

To a solution of tert-butyl 4-(4-((2-(6-(4-(ethoxycarbonyl) piperidin-1-yl)pyridin-2-yl)-4,6-difluorophenoxy)methyl)-3-methylphenyl)piperidine-1-carboxylate (2 g, 3.08 mmol) in CH$_2$Cl$_2$ (15 mL) was added dropwise TFA (4.98 mL, 64.6 mmol) at 0° C. and the reaction mixture was allowed to stirred at 0° C. for 4 hr and then concentrated under reduced pressure. The residue was dissolved in cold water and basified with a solution of Na$_2$CO$_3$ up to pH 10. After extraction with EtOAc (3×25 mL), the organic phase was dried over anhydrous Na$_2$SO$_4$, filtered and concentrated under reduced pressure to afford the title compound as a brown gum (1.6g, 95% yield).

1H NMR (DMSO, d6, ppm): 7.55 (t, 1H), 7.35 (m, 2H), 7.15 (d, 1H), 7.1 (d, 1H), 7 (m, 2H), 6.85 (d, 1H), 4.85 (s, 2H), 4.25 (m, 2H), 4.05 (q, 2H), 3.35 (m, 2H), 2.95 (m, 4H), 2.8 (m, 1H), 2.6 (m, 1H), 2.2 (s, 3H), 1.9 (m, 4H), 1.75 (m, 2H), 1.55 (m, 2H), 1.15 (t, 3H)

Example 1 ethyl 1-(6-(2-((4-(1-(cyanomethyl)piperidin-4-yl)-2-methylbenzyl)oxy)-3,5-difluorophenyl)pyridin-2-yl)piperidine-4-carboxylate

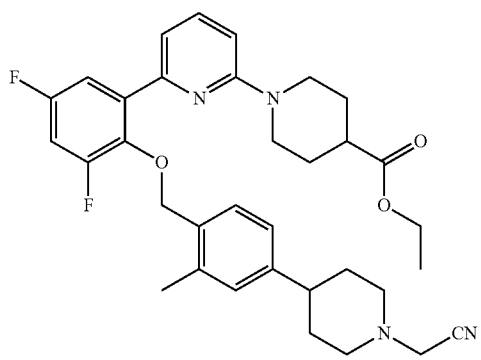 [SMILES: CCOC(=O)C1CCN(c2cccc(-c3cc(F)cc(F)c3OCc3ccc(C4CCN(CC#N)CC4)cc3C)n2)CC1]

To a solution of ethyl 1-(6-(3,5-difluoro-2-((2-methyl-4-(piperidin-4-yl)benzyl)oxy)phenyl)pyridin-2-yl)piperidine-4-carboxylate (500 mg, 0.910 mmol), in acetone (25 mL) were added 2-bromoacetonitrile (0.076 mL, 1.092 mmol) and Cs$_2$CO$_3$ (741 mg, 2.274 mmol). The reaction mixture was stirred at 60° C. for 6 hr, then concentrated under reduced pressure and the residue was dissolved in EtOAc (25 mL). The organic phase was washed with water (3×15 mL), dried over anhydrous Na$_2$SO$_4$, filtered and concentrated under reduced pressure. The residue was purified by column chromatography (12-15% EtOAc: Hexane as an eluent) to afford the title compound as a brown gum (328 mg, 61.3% yield).

$^1$H NMR (CDCl$_3$, ppm): 7.45 (m, 2H), 7.3 (m, 1H), 7.2 (m, 1H), 7 (m, 2H), 6.85 (m, 1H), 6.65 (d, 1H), 4.8 (s, 2H), 4.3 (m, 2H), 4.15 (q, 2H), 3.55 (s, 2H), 3 (m, 2H), 2.9 (m, 2H), 2.3 (m, 4H), 2.3 (s, 3H), 2 (m, 2H), 1.9 to 1.7 (m, 6H), 1.25 (t, 3H)

Example 2

1-(6-(2-((4-(1-(cyanomethyl)piperidin-4-yl)-2-methylbenzyl)oxy)-3,5-difluorophenyl)pyridin-2-yl)piperidine-4-carboxylic acid

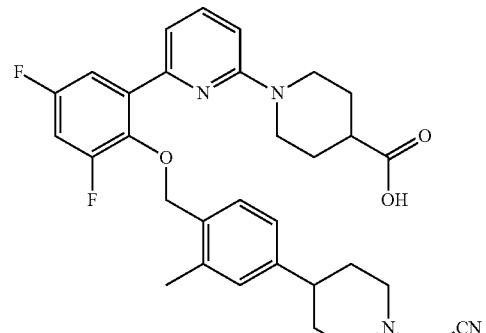

To a solution of ethyl 1-(6-(2-((4-(1-(cyanomethyl)piperidin-4-yl)-2-methylbenzyl)oxy)-3,5-difluorophenyl)pyridin-2-yl)piperidine-4-carboxylate (328 mg, 0.557 mmol) in ethanol (2 mL) and water (0.2 mL) was added NaOH (33.4 mg, 0.836 mmol) at 0° C. The reaction mixture was stirred at room temperature for 16 hours and then diluted with water (10 mL) and acidified with a citric acid solution (pH adjusted to ~6). After extraction with EtOAc (3×20 mL), the organic phase was washed with brine solution (25 mL), dried over anhydrous Na$_2$SO$_4$ and concentrated under reduced pressure. The residue was purified by HPLC (gradient Formic acid/CH$_3$CN). Fractions were collected and lyophilized to afford the title compound as white solid (130mg, 40.3% yield).

$^1$H NMR (DMSO d6 ppm): 7.54 (dd, 1H), 7.36 (m, 2H), 7.09 (d, 2H), 7.01 (m, 2H), 6.85 (d, 1H), 4.82 (s, 2H), 4.24 (m, 1H), 4.21 (m, 1H), 3.73 (s, 2H), 2.96 to 2.86 (m, 4H), 2.45 (m, 2H), 2.27 (m, 2H), 2.2 (s, 3H), 1.87 (m, 2H), 1.79 (m, 2H), 1.66 (m, 2H), 1.55 (m, 2H)

LCMS (a): Rt=2.74 min, M/z=561.39 (M+H)$^+$

Example 3 ethyl 1-(6-(3,5-difluoro-2-((2-methyl-4-(1-(2,2,2-trifluoroethyl)piperidin-4-yl)benzyl)oxy)phenyl)pyridin-2-yl)piperidine-4-carboxylate

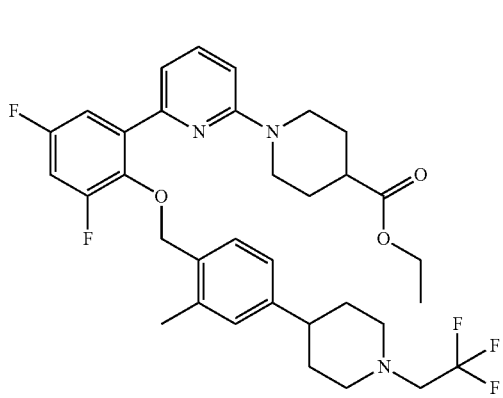 [SMILES: CCOC(=O)C1CCN(c2cccc(-c3cc(F)cc(F)c3OCc3ccc(C4CCN(CC(F)(F)F)CC4)cc3C)n2)CC1]

Example 4 ethyl 1-(6-(3,5-difluoro-2-((2-methyl-4-(1-(oxetane-3-carbonyl)piperidin-4-yl)benzyl)oxy)phenyl)pyridin-2-yl)piperidine-4-carboxylate

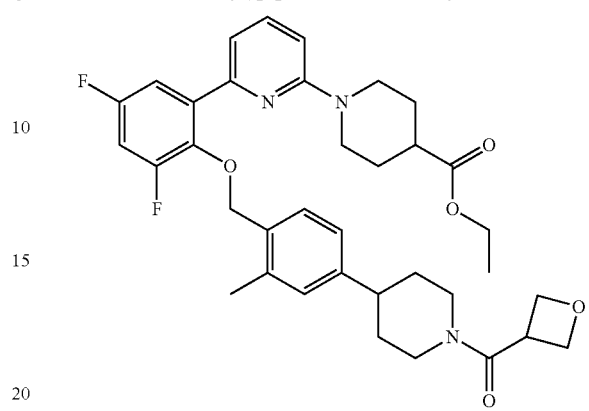

To a solution of ethyl 1-(6-(3,5-difluoro-2-((2-methyl-4-(piperidin-4-yl)benzyl)oxy)phenyl)pyridin-2-yl)piperidine-4-carboxylate (500 mg, 0.910 mmol) and oxetane-3-carboxylic acid (0.065 ml, 1.092 mmol) in N,N-Dimethylformamide (2 ml) were added HATU (519 mg, 1.365 mmol) followed by TEA (0.190 ml, 1.365 mmol) at 0° C. and the reaction mixture was allowed to stirred at room temperature for 16 hours. After dilution with water (10 mL) and extraction with EtOAc (3×20 mL), the organic phase was washed with brine solution (25 mL), dried over anhydrous $Na_2SO_4$ and concentrated under reduced pressure. The residue was purified by column chromatography (EtOAc: Hexane, 1:9) and then by HPLC (gradient 0.1% Formic acid (Aq): ACN:MeOH (1:1)). Fractions were collected and concentrated under reduced pressure to remove ACN, the aqueous layer was extracted with EtOAc (2×50 ml). The organic layer was separated, dried over anhydrous $Na_2SO_4$, filtered and concentrated under reduced pressure. The residue was triturated with pentane (3×5 mL), filtered and dried under high vacuo to afford the title compound (80 mg, 13.28% yield).

LCMS: Rt: 2.92 min, M/z=634.37 $(M+H)^+$

The following examples were prepared using a similar procedure to the one described for Example 2.

To a solution of ethyl 1-(6-(3,5-difluoro-2-((2-methyl-4-(piperidin-4-yl)benzyl)oxy)phenyl)pyridin-2-yl)piperidine-4-carboxylate (600 mg, 1.092 mmol)) in acetone (15 ml) were added 2,2,2-trifluoroethyl trifluoromethanesulfonate (0.177 ml, 1.310 mmol) and $Cs_2CO_3$ (889 mg, 2.73 mmol). The reaction mixture was stirred at 60° C. for 6 hr, then cooled and diluted with water (150 mL). After extraction with EtOAc (5×25 mL), the combined organic phase was washed with a saturated NaCl solution, dried over anhydrous $Na_2SO_4$, filtered and concentrated under reduced pressure. The residue was purified by column chromatography (12-15% EtOAc: Hexane as an eluent) to afford the title compound (340 mg, 45.4% yield) as a brown gum.

LCMS (a): Rt: 4.47 min, M/z=632 $(M+H)^+$

| Ex. | Name | LC/MS | 1H NMR (ppm) |
|---|---|---|---|
| 5 | 1-(6-(3,5-difluoro-2-((2-methyl-4-(1-(2,2,2-trifluoroethyl)piperidin-4-yl)benzyl)oxy)phenyl)pyridin-2-yl)piperidine-4-carboxylic acid | (a) Rt = 2.86 min, M/z = 604.31 $(M + H)^+$ | DMSO d6: 7.54 (dd, 1H), 7.37 (m, 2H), 7.09 (dd, 2H), 7.05 (m, 2H), 6.86 (d, 1H), 4.81 (s, 2H), 4.23 (m, 2H), 3.17 (q, 2H), 2.96 (m, 4H), 2.43 (m, 4H), 2.19 (s, 3H), 1.88 (m, 2H), 1.7 to 1.5 (m, 6H) |

| Ex. | Name | LC/MS | 1H NMR (ppm) |
|---|---|---|---|
| 6 | 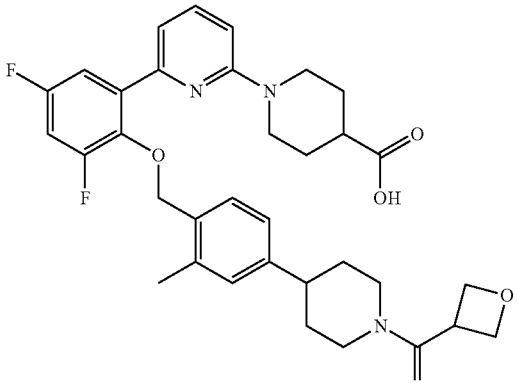<br>1-(6-(3,5-difluoro-2-((2-methyl-4-(1-(oxetane-3-carbonyl)piperidin-4-yl)benzyl)oxy)phenyl)pyridin-2-yl)piperidine-4-carboxylic acid | (a) Rt = 2.39 min, M/z = 606.33 (M + H) | DMSO d6: 7.54 (dd, 1H), 7.36 (m, 2H), 7.08 (d, 2H), 7 (m, 2H), 6.85 (d, 1H), 4.82 (s, 2H), 4.7 (m, 4H), 4.53 (m, 1H), 4.23 (m, 2H), 4.13 (m, 1H), 3.43 (m, 1H), 3 to 2.9 (m, 3H), 2.7 (m, 2H), 2.46 (m, 1H), 2.19 (s, 3H), 1.9 (m, 2H), 1.73 (m, 2H), 1.58 to 1.42 (m, 4H) |

It would be understood by the skilled artisan that the sodium salt of the compound of Example 5 may be made in accordance with the Examples herein and in accordance with standard practices in the art.

Intermediate 5: tert-butyl 5-(hydroxymethyl)-4-methyl-5',6'-dihydro-[2,4'-bipyridine]-1'(2'H)-carboxylate

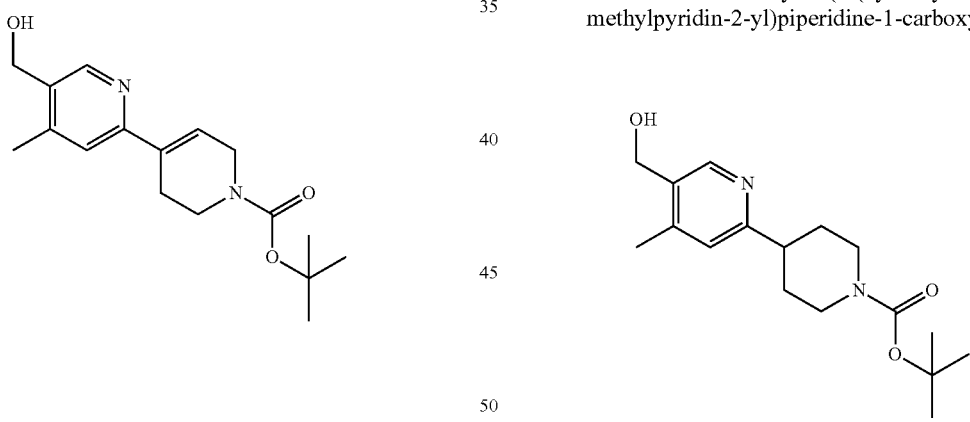

To a solution of (6-chloro-4-methylpyridin-3-yl)methanol (5 g, 31.7 mmol) in 1,2-dimethoxyethane (10 mL) and water (3 mL) stirred under nitrogen at room temperature, were added tert-butyl 4-(4,4,5,5-tetramethyl-1,3,2-dioxaborolan-2-yl)-5,6-dihydropyridine-1(2H)-carboxylate (14.72 g, 47.6 mmol) and $Na_2CO_3$ (6.73 g, 63.5 mmol). The reaction mixture was purged with argon gas for 30 minute and then tetrakis(triphenylphosphine)palladium(0) (3.67 g, 3.17 mmol) was added. The reaction mixture was stirred at 100° C. for 16 hours, then cooled and diluted with water (50 mL) and extracted with EtOAc (3×200 mL). The combined organic phase was washed with brine solution (50 mL), dried over anhydrous $Na_2SO_4$ and concentrated under reduced pressure. The residue was purified by column chromatography (silica gel 100-200 mesh, eluted with 30% EtOAc in Hexane). Collected fractions were concentrated under reduced pressure to afford the title compound (6 g, 49.7% % yield) as off white semi solid.

LC/MS (c): Rt=3.22 min, M/z=305.36 (M+H)⁺

Intermediate 6: tert-butyl 4-(5-(hydroxymethyl)-4-methylpyridin-2-yl)piperidine-1-carboxylate To a solution of tert-butyl 5-(hydroxymethyl)-4-methyl-5',6'-dihydro-[2,4'-bipyridine]-1'(2'H)-carboxylate (6 g, 19.71 mmol) in EtOAc (100 mL) stirred under nitrogen at room temperature, was added platinum(IV) oxide (4.48 g, 19.71 mmol). The reaction mixture was then stirred under hydrogen pressure (30 psi) at room temperature for 16 hours. The catalyst was filtered off on a celite pad and washed with EtOAc. The filtrate was concentrated under reduced pressure to afford the title compound (5 g, 61.3% yield) as an off-white solid.

LC/MS (a): Rt=1.44 min, M/z=307.30 (M+H)⁺

Intermediate 7: tert-butyl 4-(5-((2-(6-(4-(ethoxycarbonyl)piperidin-1-yl)pyridin-2-yl)-4,6-difluorophenoxy)methyl)-4-methylpyridin-2-yl)piperidine-1-carboxylate

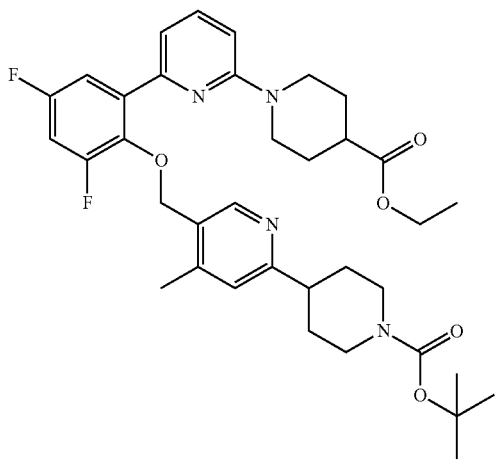 [SMILES: CCOC(=O)C1CCN(c2cccc(-c3cc(F)cc(F)c3OCc3cnc(C4CCN(C(=O)OC(C)(C)C)CC4)cc3C)n2)CC1]

To a solution of ethyl 1-(6-(3,5-difluoro-2-hydroxyphenyl)pyridin-2-yl)piperidine-4-carboxylate (5 g, 13.80 mmol), tert-butyl 4-(5-(hydroxymethyl)-4-methylpyridin-2-yl)piperidine-1-carboxylate (4.23 g, 13.80 mmol) and triphenylphosphine (3.62 g, 13.80 mmol) in THF (25 mL) stirred under nitrogen at 0° C., was added dropwise a solution of DEAD (2.185 mL, 13.80 mmol) in THF (10 mL). The reaction mixture was stirred at room temperature for 16 hours and then was diluted with water (20 mL) and extracted with EtOAc (3×30 mL). The combined organic phase was washed with brine solution (25 mL), dried over anhydrous Na$_2$SO$_4$ and concentrated under reduced pressure. The residue was purified by column chromatography (silica gel 100-200 mesh, eluted with 20% EtOAc in Hexane). Collected fractions were concentrated under reduced pressure to afford the title compound (5 g, 52.6% yield) as an off-white solid.

LC/MS (a): Rt=2.87 min, M/z=651.45 (M+H)$^+$

Intermediate 8: ethyl 1-(6-(3,5-difluoro-2-((4-methyl-6-(piperidin-4-yl)pyridin-3-yl)methoxy)phenyl)pyridin-2-yl)piperidine-4-carboxylate

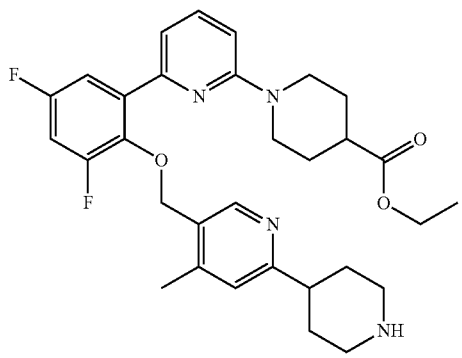 [SMILES: CCOC(=O)C1CCN(c2cccc(-c3cc(F)cc(F)c3OCc3cnc(C4CCNCC4)cc3C)n2)CC1]

To a solution of tert-butyl 4-(5-((2-(6-(4-(ethoxycarbonyl)piperidin-1-yl)pyridin-2-yl)-4,6-difluorophenoxy)methyl)-4-methylpyridin-2yl)piperidine-1-carboxylate (2 g, 3.07 mmol), in CH$_2$Cl$_2$ (20 mL) stirred under nitrogen at 0° C. was added TFA (0.237 mL, 3.07 mmol). The reaction mixture was stirred at room temperature for 16 hours and then diluted with water (10 mL) and a solution of Na$_2$CO$_3$. After extraction with EtOAc (3×20 mL), the combined organic phase was washed with brine solution (25 mL), dried over anhydrous Na$_2$SO$_4$ and concentrated under reduced pressure to afford the title compound (1.3 g, 60.7% yield) as a gummy liquid.

LC/MS (a): Rt=1.99 min, M/z=551.46 (M+H)$^+$

Example 7 ethyl 1-(6-(3,5-difluoro-2-((4-methyl-6-(1-(2,2,2-trifluoroethyl)piperidin-4-yl)pyridin-3-yl)methoxy)phenyl)pyridin-2-yl)piperidine-4-carboxylate

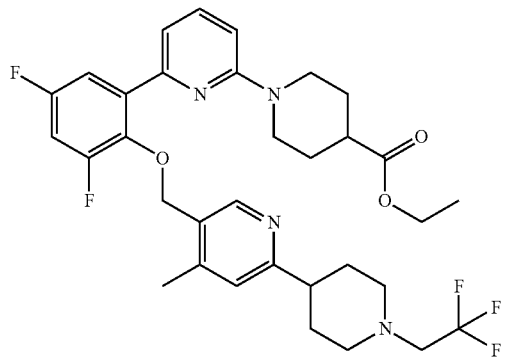 [SMILES: CCOC(=O)C1CCN(c2cccc(-c3cc(F)cc(F)c3OCc3cnc(C4CCN(CC(F)(F)F)CC4)cc3C)n2)CC1]

To a solution of ethyl 1-(6-(3,5-difluoro-2-((4-methyl-6-(piperidin-4-yl)pyridin-3-yl)methoxy)phenyl)pyridin-2-yl)piperidine-4-carboxylate (500 mg, 0.908 mmol) in acetone (10 mL) stirred under nitrogen, were added Cs$_2$CO$_3$ (740 mg, 2.270 mmol) and 2,2,2-trifluoroethyl trifluoromethanesulfonate (253 mg, 1.090 mmol). The reaction mixture was stirred at 70° C. for 16 hours and then was diluted with water (10 mL) and extracted with EtOAc (3×20 mL). The organic phase was washed with brine solution (25 mL), dried over anhydrous Na$_2$SO$_4$ and concentrated under reduced pressure. The residue was purified by column chromatography (silica gel 100-200 mesh, eluted with 10% EtOAc in Hexane). Collected fractions were concentrated under reduced pressure to afford the title compound (180 mg, 31.3% yield).

LC/MS (c): Rt=4.49 min, M/z=633.43 (M+H)$^+$

Example 8

1-(6-(3,5-difluoro-2-((4-methyl-6-(1-(2,2,2-trifluoroethyl)piperidin-4-yl)pyridin-3-yl)methoxy)phenyl)pyridin-2-yl)piperidine-4-carboxylic acid

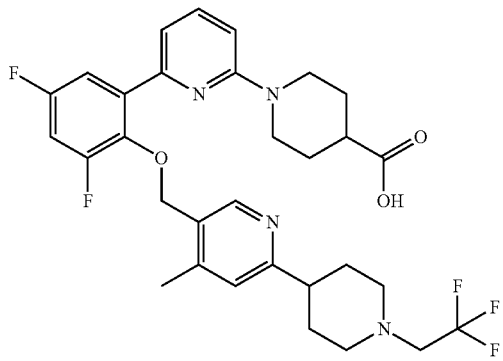 [SMILES: Cc1cc(C2CCN(CC(F)(F)F)CC2)ncc1COc1c(F)cc(F)cc1-c1cccc(N2CCC(C(=O)O)CC2)n1]

To a solution of ethyl 1-(6-(3,5-difluoro-2-((4-methyl-6-(1-(2,2,2-trifluoroethyl)piperidin-4-yl)pyridin-3-yl)methoxy)phenyl)pyridin-2-yl)piperidine-4-carboxylate (180 mg, 0.285 mmol) in ethanol (2 mL) stirred under nitrogen at 0° C. was added a solution of NaOH (22.76 mg, 0.569 mmol) in water (1 mL) dropwise during 5 min. The reaction mixture was stirred at room temperature for 16 hours and then was concentrated under reduced pressure. The residue was dissolved in water (10 mL) and the pH adjusted to 5 using an acetic acid solution. The resulting precipitate was filtered, washed with water, then n-pentane and dried under vacuum to afford 1-(6-(3,5-difluoro-2-((4-methyl-6-(1-(2,2,2-trifluoroethyl)piperidin-4-yl)pyridin-3-yl)methoxy)phenyl)pyridin-2-yl)piperidine-4-carboxylic acid (75 mg, 42.3% yield) as an off-white solid.

$^1$H NMR (CDCl$_3$, ppm): 8.2 (s, 1H), 7.5 (m, 1H), 7.3 (m, 1H), 7.15 (d, 1H), 6.95 (s, 1H), 6.85 (m, 1H), 6.65 (d, 1H), 4.85 (s, 2H), 4.2 (m, 2H), 3.1 (m, 4H), 3.05 (q, 2H), 2.65 (m, 2H), 2.5 (m, 2H), 2.3 (s, 3H), 2 (m, 2H), 1.9 (m, 6H)

LC/MS (h): Rt=2.51 min, M/z=605.05 (M+H)$^+$

Example 9

1-(6-(3,5-difluoro-2-((4-methyl-6-(1-(2,2,2-trifluoroethyl)piperidin-4-yl)pyridin-3-yl)methoxy)phenyl)pyridin-2-yl)piperidine-4-carboxylic acid, sodium salt

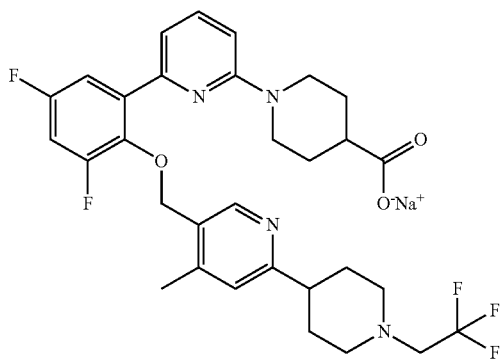

To a solution of 1-(6-(3,5-difluoro-2-((4-methyl-6-(1-(2,2,2-trifluoroethyl)piperidin-4-yl)pyridin-3-yl)methoxy)phenyl)pyridin-2-yl)piperidine-4-carboxylic acid (75 mg, 0.124 mmol) in water (7 mL) was added NaOH (4.96 mg, 0.124 mmol) in Water (5 mL). The reaction mixture was stirred at room temperature for 20 minutes and then was transferred to a lyophilization flask and lyophilized for 20 hours to afford 1-(6-(3,5-difluoro-2-((4-methyl-6-(1-(2,2,2-trifluoroethyl)piperidin-4-yl)pyridin-3-yl)methoxy)phenyl)pyridin-2-yl)piperidine-4-carboxylic acid, sodium salt (75 mg, 95% yield) as an off-white solid.

LC/MS (c): Rt=3.56 min, M/z=605.40 (M+H)$^+$

1H NMR (DMSO d6 ppm): 8.15 (s, 1H), 7.5 (m, 1H), 7.35 (m, 2H), 7.07 (s, 1H), 7 (d, 1H), 6.8 (d, 1H), 4.9 (s, 2H), 4.15 (m, 2H), 3.15 (q, 2H), 3 (m, 2H), 2.9 (m, 2H), 2.55 (m, 1H), 2.45 (m, 2H), 2.2 (s, 3H), 2 (m, 1H), 1.75 (m, 6H), 1.5 (m, 2H)

Example 10 ethyl 1-(6-(2-((6-(1-(cyanomethyl)piperidin-4-yl)-4-methylpyridin-3-yl)methoxy)-3,5-difluorophenyl)pyridin-2-yl)piperidine-4-carboxylate

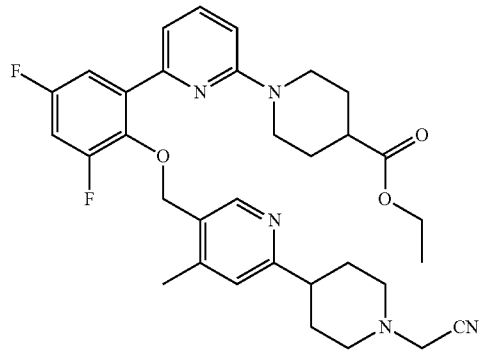

To a solution of ethyl 1-(6-(3,5-difluoro-2-((4-methyl-6-(piperidin-4-yl)pyridin-3-yl)methoxy)phenyl)pyridin-2-yl)piperidine-4-carboxylate (450 mg, 0.817 mmol) in acetone(5 mL) stirred under nitrogen at room temperature, were added Cs$_2$CO$_3$ (666 mg, 2.043 mmol) and 2-chloroacetonitrile (74.0 mg, 0.981 mmol). The reaction mixture was stirred at 70° C. for 16 hours and then was diluted with water (10 mL) and extracted with EtOAc (3×20 mL). The combined organic phase was washed with brine solution (25 mL), dried over anhydrous Na$_2$SO$_4$ and concentrated under reduced pressure. The residue was purified by column chromatography (silica gel 100-200 mesh, eluted with 10% EtOAc in Hexane). Collected fractions were concentrated under reduced pressure to afford the title compound (200 mg, 38.0% yield) as gummy solid.

LC/MS (a): Rt=2.32 min, M/z=590.46 (M+H)$^+$

Example 11

1-(6-(2-((6-(1-(cyanomethyl)piperidin-4-yl)-4-methylpyridin-3-yl)methoxy)-3,5-difluorophenyl)pyridin-2-yl)piperidine-4-carboxylic acid

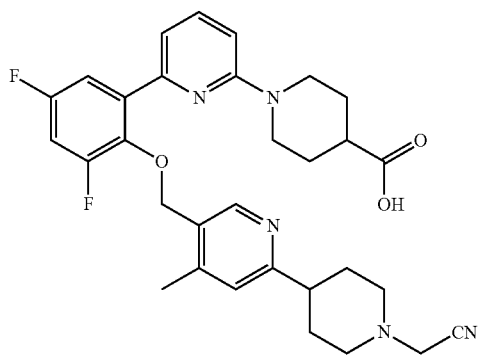

To a solution of ethyl 1-(6-(2-((6-(1-(cyanomethyl)piperidin-4-yl)-4-methylpyridin-3-yl)methoxy)-3,5-difluorophenyl)pyridin-2-yl)piperidine-4-carboxylate (200 mg, 0.339 mmol) in ethanol (5 mL) stirred under nitrogen at 0° C., was added a solution of NaOH (16.28 mg, 0.407 mmol) in water (2 mL) dropwise during 15 min. The reaction mixture was stirred at 20° C. for 16 hours, then diluted with water (10 mL) and acidified with acetic acid (pH adjusted to ~5). The resulting precipitate was filtered and washed with n-pentane. The solid was purified by Prep-TLC (silica gel GF 254, eluted with 8% MeOH in $CH_2Cl_2$). After trituration with pentane, the product was filtered and dried to afford the title compound (53 mg, 27.7% yield) as an off-white solid.

LC/MS (c): Rt=3.18 min, M/z=562.24 (M+H)$^+$

1H NMR (DMSO d6 ppm): 8.15 (s, 1H), 7.55 (t, 1H), 7.35 (m, 2H), 7.05 (s+d, 2H), 6.85 (d, 1H), 4.85 (s, 2H), 4.2 (m, 2H), 3.75 (s, 2H), 2.9 (m, 4H), 2.6 (m, 1H), 2.4 (m, 1H), 2.25 (m, 2H), 2.2 (s, 3H), 1.9 to 1.8 (m, 4H), 1.7 (m, 2H), 1.55 (m, 2H)

Example 12

1-(6-(2-((6-(1-(cyanomethyl)piperidin-4-yl)-4-methylpyridin-3-yl)methoxy)-3,5-difluorophenyl)pyridin-2-yl)piperidine-4-carboxylic acid, sodium salt

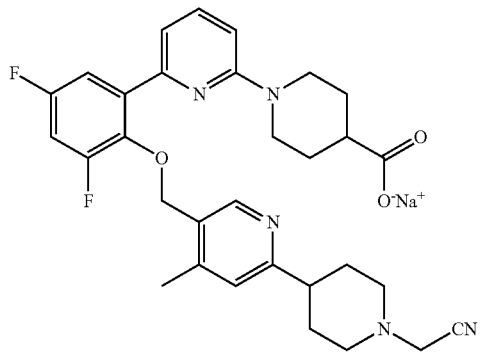

To a solution of 1-(6-(2-((6-(1-(cyanomethyl)piperidin-4-yl)-4-methylpyridin-3-yl)methoxy)-3,5-difluorophenyl)pyridin-2-yl)piperidine-4-carboxylic acid (53 mg, 0.094 mmol) in water (3 mL) was added sodium bicarbonate (7.93 mg, 0.094 mmol) in Water (2 mL). The reaction mixture was stirred at room temperature for 20 minutes and then was transferred to a lyophilization flask and lyophilized for 20 hours to afford the title compound (34 mg, 59.2% yield) as an off-white sticky solid.

LC/MS (a): Rt=1.97 min, M/z=562.3 (M+H)$^+$

1H NMR (DMSO d6 ppm): 8.15 (s, 1H), 7.5 (m, 1H), 7.35 (m, 2H), 7.08 (s, 1H), 7 (d, 1H), 6.8 (d, 1H), 4.88 (s, 2H), 4.14 (m, 1H), 4.11 (m, 1H), 3.73 (s, 2H), 2.88 (m, 4H), 2.29 (m, 2H), 2.07 (s, 3H), 2 (m, 2H), 1.84 to 1.7 (m, 6H), 1.5 (m, 2H)

Intermediate 9: tert-butyl 5-(hydroxymethyl)-6-methyl-5',6'-dihydro-[2,4'-bipyridine]-1'(2'H)-carboxylate

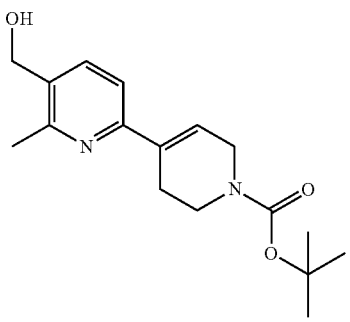 [SMILES: Cc1nc(C2=CCN(C(=O)OC(C)(C)C)CC2)ccc1CO]

To a solution of (6-chloro-2-methylpyridin-3-yl)methanol (5 g, 31.7 mmol) in 1,2-Dimethoxyethane (10 mL) and Water (3 mL) stirred under nitrogen at room temperature, were added tert-butyl 4-(4,4,5,5-tetramethyl-1,3,2-dioxaborolan-2-yl)-5,6-dihydropyridine-1(2H)-carboxylate (14.72 g, 47.6 mmol) and $Na_2CO_3$ (6.73 g, 63.5 mmol). The reaction mixture was purged with argon gas for 30 minutes and then tetrakis(triphenylphosphine)-palladium(0) (3.67 g, 3.17 mmol) was added. The reaction mixture stirred at 100° C. for 16 hours, then cooled, diluted with water (50 mL) and extracted with EtOAc (3×50 mL). The combined organic phase was washed with brine solution (50 mL), dried over anhydrous $Na_2SO_4$ and concentrated under reduced pressure. The residue was purified by column chromatography (silica gel 100-200 mesh, eluted with 10% EtOAc in Hexane). Collected fractions were concentrated under reduced pressure to afford the title compound (7 g, 18.53 mmol, 58.4% yield) as an off-white solid.

LC/MS (a): Rt=1.44 min, M/z=305.32 (M+H)$^+$

Intermediate 10: tert-butyl 4-(5-(hydroxymethyl)-6-methylpyridin-2-yl)piperidine-1-carboxylate

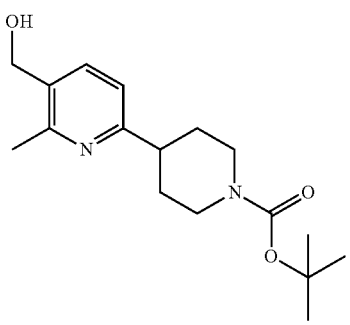 [SMILES: Cc1nc(C2CCN(C(=O)OC(C)(C)C)CC2)ccc1CO]

To a solution of tert-butyl 5-(hydroxymethyl)-6-methyl-5',6'-dihydro-[2,4'-bipyridine]-1'(2'H)-carboxylate (7 g, 23.00 mmol) in EtOAc (100 mL) was added platinum(IV) oxide (2.61 g, 11.50 mmol) under nitrogen. The reaction mixture was stirred under hydrogen pressure (30 psi) at room temperature. The catalyst was filtered off on a celite pad and washed with EtOAc (3×30mL). The filtrate was concentrated under reduced pressure to afford the title compound (5.5 g, 68.3% yield) as off-white solid.

LC/MS (a): Rt=3.18 min, M/z=307.31 (M+H)$^+$

Intermediate 11: tert-butyl 4-(5-((2-(6-(4-(ethoxy-carbonyl)piperidin-1-yl)pyridin-2-yl)-4,6-difluoro-phenoxy)methyl)-6-methylpyridin-2-yl)piperidine-1-carboxylate

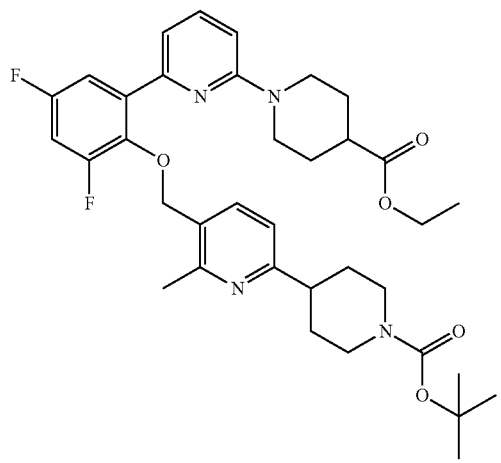 [SMILES: CCOC(=O)C1CCN(c2cccc(-c3cc(F)cc(F)c3OCc3ccc(C4CCN(C(=O)OC(C)(C)C)CC4)nc3C)n2)CC1]

To a solution of ethyl 1-(6-(3,5-difluoro-2-hydroxyphe-nyl)pyridin-2-yl)piperidine-4-carboxylate (3 g, 8.28 mmol) and in THF (15 mL) stirred under nitrogen at 0° C., were added tert-butyl 4-(5-(hydroxymethyl)-6-methylpyridin-2-yl)piperidine-1-carboxylate (3.80 g, 12.42 mmol) and triph-enylphosphine (4.34 g, 16.56 mmol). The reaction mixture was stirred at 0° C. for 10 minutes and then a solution of DEAD (2.62 mL, 16.56 mmol) in THF (10 mL) was added dropwise during 15 min. The reaction mixture was stirred at room temperature for 16 hours and then was diluted with water (30 mL) and extracted with EtOAc (3×50 mL). The combined organic phase was washed with brine solution (50 mL), dried over anhydrous Na$_2$SO$_4$ and concentrated under reduced pressure. The residue was purified by column chromatography (silica gel 100-200 mesh, eluted with 10% EtOAc in Hexane). Collected fractions were concentrated under reduced pressure to afford the title compound (4 g, 66.6% yield) as off-white solid.

LC/MS (c): Rt=4.62 min, M/z=651.44 (M+H)$^+$

Intermediate 12: ethyl 1-(6-(3,5-difluoro-2-((2-methyl-6-(piperidin-4-yl)pyridin-3-yl)methoxy)phe-nyl)pyridin-2-yl)piperidine-4-carboxylate

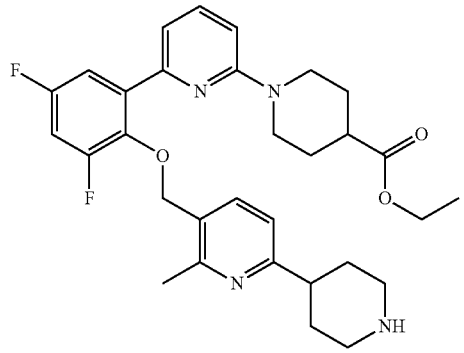 [SMILES: CCOC(=O)C1CCN(c2cccc(-c3cc(F)cc(F)c3OCc3ccc(C4CCNCC4)nc3C)n2)CC1]

A solution of tert-butyl 4-(5-((2-(6-(4-(ethoxycarbonyl)piperidin-1-yl)pyridin-2-yl)-4,6-difluorophenoxy)methyl)-6-methylpyridin-2-yl)piperidine-1-carboxylate (4 g, 6.15 mmol) and TFA (0.474 mL, 6.15 mmol) in CH$_2$Cl$_2$ (20 mL) was stirred under nitrogen at 0-15° C. for 20 hours and then was diluted with water (10 mL) and a sodium bicarbonate solution. After extraction with EtOAc (3×20 mL), the combined organic phase was washed with brine solution (25 mL), dried over anhydrous Na$_2$SO$_4$ and concentrated under reduced pressure to afford the title compound (2.8 g, 66.9% yield).

LC/MS (a): Rt=2.13 min, M/z=551.39 (M+H)$^+$

Example 13 ethyl 1-(6-(3,5-difluoro-2-((2-methyl-6-(1-(2,2,2-trifluoroethyl)piperidin-4-yl)pyridin-3-yl)methoxy)phenyl)pyridin-2-yl)piperidine-4-carboxylate

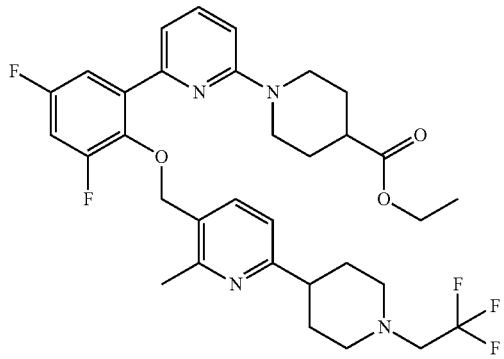 [SMILES: CCOC(=O)C1CCN(c2cccc(-c3cc(F)cc(F)c3OCc3ccc(C4CCN(CC(F)(F)F)CC4)nc3C)n2)CC1]

To a solution of ethyl 1-(6-(3,5-difluoro-2-((2-methyl-6-(piperidin-4-yl)pyridin-3-yl)methoxy)phenyl)pyridin-2-yl)piperidine-4-carboxylate (500 mg, 0.908 mmol) in acetone (5 mL) stirred under nitrogen, were added and 2,2,2-trifluoroethyl trifluoromethanesulfonate (253 mg, 1.090 mmol) and Cs$_2$CO$_3$ (740 mg, 2.270 mmol). The reaction mixture was stirred at 60° C. for16 hours and then was diluted with water (10 mL) and extracted with EtOAc (3×20 mL). The combined organic phase was washed with brine solution (25 mL), dried over anhydrous Na$_2$SO$_4$ and concentrated under reduced pressure. The residue was purified by column chromatography (silica gel 100-200 mesh, eluted with 10% EtOAc in Hexane). Collected fractions were concentrated under reduced pressure to afford the title compound (320 mg, 53.7% yield).

LC/MS (a): Rt=2.99 min, M/z=633.3 (M+H)+

Example 14

1-(6-(3,5-difluoro-2-((2-methyl-6-(1-(2,2,2-trifluoroethyl)piperidin-4-yl)pyridin-3-yl)methoxy)phenyl)pyridin-2-yl)piperidine-4-carboxylic acid

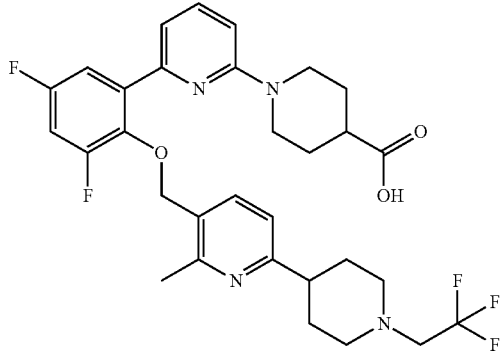 [SMILES: Cc1nc(C2CCN(CC(F)(F)F)CC2)ccc1COc1c(F)cc(F)cc1-c1cccc(N2CCC(C(=O)O)CC2)n1]

To a solution of ethyl 1-(6-(3,5-difluoro-2-((2-methyl-6-(1-(2,2,2-trifluoroethyl)piperidin-4-yl)pyridin-3-yl)methoxy)phenyl)pyridin-2-yl)piperidine-4-carboxylate (300 mg, 0.474 mmol) in ethanol (3 mL) was added NaOH(37.9 mg, 0.948 mmol) in water (1 mL). The reaction mixture was stirred at room temperature for 16 hours and then was diluted with water (10 mL) and acidified with a citric acid solution (pH adjusted to 4). The resulting precipitate was filtered, washed with n-pentane and dried to afford the title compound (250 mg, 84% yield) as an off-white solid.

LCMS (h): Rt=2.48 min, M/z=605.1 (M+H)+

1H-NMR: (CDCl₃, ppm): 7.5 (t, 1H), 7.4 (d, 1H), 7.3 (m, 1H), 7.15 (d, 1H), 6.9 (m, 2H), 6.65 (d, 1H), 4.9 (s, 2H), 4.15 (m, 2H), 3.1 (m, 4H), 3.03 (q, 2H), 2.65 (m, 2H), 2.5 (m, 2H), 2.45 (s, 3H), 2 (m, 2H), 1.9 (m, 2H), 1.8 (m, 4H)

Example 15

1-(6-(3,5-difluoro-2-((2-methyl-6-(1-(2,2,2-trifluoroethyl)piperidin-4-yl)pyridin-3-yl)methoxy)phenyl)pyridin-2-yl)piperidine-4-carboxylic acid, sodium salt

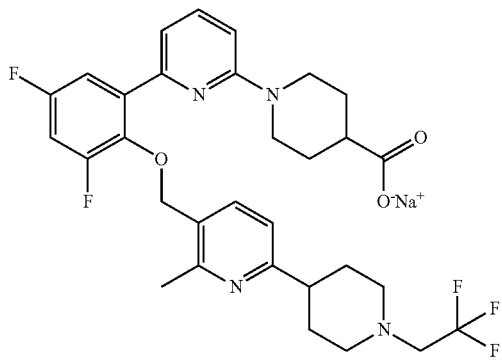

To a solution of 1-(6-(3,5-difluoro-2-((2-methyl-6-(1-(2,2,2-trifluoroethyl)piperidin-4-yl)pyridin-3-yl)methoxy)phenyl)pyridin-2-yl)piperidine-4-carboxylic acid (150 mg, 0.248 mmol) in water (7 mL) was added sodium hydroxide (9.92 mg, 0.248 mmol) in water (5 mL). The reaction mixture was stirred at room temperature for 20 minutes and then was transferred to a lyophilization flask and lyophilized for 20 h to afford 1-(6-(3,5-difluoro-2-((2-methyl-6-(1-(2,2,2-trifluoroethyl)piperidin-4-yl)pyridin-3-yl)methoxy)phenyl)pyridin-2-yl)piperidine-4-carboxylic acid, Sodium salt (129 mg, 83% yield) as an off-white solid.

¹H-NMR: (DMSO d6 ppm): 7.5 (dd, 1H), 7.44 (d, 1H), 7.36 (m, 2H), 7.02 (t, 2H), 6.8 (d, 1H), 4.87 (s, 2H), 4.16 (m, 1H), 4.13 (m, 1H), 3.18 (q, 2H), 3 (m, 2H), 2.88 (m, 2H), 2.58 (m, 1H), 2.44 (m, 2H), 2.37 (s, 3H), 2.04 (m, 1H), 1.8 to 1.68 (m, 6H), 1.55 to 1.45 (m, 2H)

LCMS (a): Rt=2.19 min, M/z=605.35 (M+H)+

Example 16 ethyl 1-(6-(3,5-difluoro-2-((2-methyl-6-(1-(oxetan-3-yl)piperidin-4-yl)pyridin-3-yl)methoxy)phenyl)pyridin-2-yl)piperidine-4-carboxylate

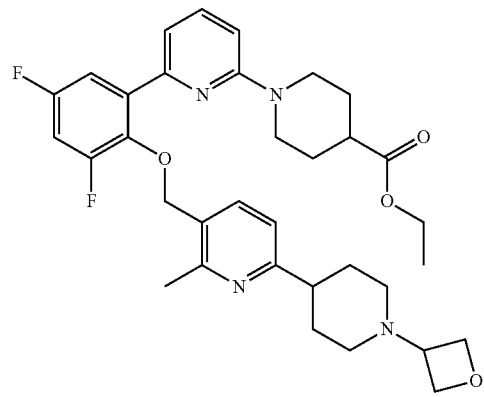 [SMILES: CCOC(=O)C1CCN(c2cccc(-c3cc(F)cc(F)c3OCc3ccc(C4CCN(C5COC5)CC4)nc3C)n2)CC1]

To a suspension of molecular sieves in Methanol (2 mL) were added ethyl 1-(6-(3,5-difluoro-2-((2-methyl-6-(piperidin-4-yl)pyridin-3-yl)methoxy)phenyl)pyridin-2-yl)piperidine-4-carboxylate (350 mg, 0.636 mmol) and oxetan-3-one (55.0 mg, 0.763 mmol) in Methanol (2 mL) and then was added one drop of acetic acid. The reaction mixture was stirred at room temperature under nitrogen for 2 hours. Then NaCNBH₄ (19.97 mg, 0.318 mmol) was added and the reaction mixture was stirred at 50° C. for 16 hours and then was diluted with water (10 mL) and extracted with EtOAc (3×20 mL). The combined organic phase was washed with brine solution (25 mL), dried over anhydrous Na₂SO₄ and concentrated under reduced pressure. The residue was purified by column chromatography (silica gel 100-200 mesh, eluted with 5% MeOH in CH₂Cl₂). Collected fractions were concentrated under reduced pressure to afford the title compound (300 mg, 74.5% yield) as an off-white solid.

LCMS (h): Rt=3.2 min, M/z=607.55 (M+H)+

Example 17

1-(6-(3,5-difluoro-2-((2-methyl-6-(1-(oxetan-3-yl)piperidin-4-yl)pyridin-3-yl)methoxy)phenyl)pyridin-2-yl)piperidine-4-carboxylic acid

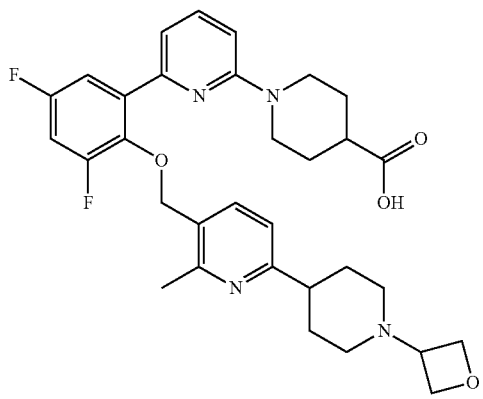 [SMILES: Cc1nc(C2CCN(C3COC3)CC2)ccc1COc1c(F)cc(F)cc1-c1cccc(N2CCC(C(=O)O)CC2)n1]

To a solution of ethyl 1-(6-(3,5-difluoro-2-((2-methyl-6-(1-(oxetan-3-yl)piperidin-4-yl)pyridin-3-yl)methoxy)phenyl)pyridin-2-yl)piperidine-4-carboxylate (310 mg, 0.511 mmol) in ethanol (5 mL) stirred under nitrogen, was added a solution of NaOH (40.9 mg, 1.022 mmol) in water (1 mL) dropwise during 5 min. The reaction mixture was stirred at room temperature for 16 hours, and then was diluted with water (10 mL) and the pH adjusted with a citric acid solution. After extraction with $CH_2Cl_2$/MeOH (9/1) (3×20 mL), the combined organic phase was dried over anhydrous $Na_2SO_4$ and concentrated under reduced pressure. The residue was purified by Prep-HPLC. Prep-HPLC Purification conditions:

Prep HPLC Column:

Column: Xbridge (19×250 mm) 5 μ

Mobile Phase: 10 mm AMMONIUM BICARBONATE (Aq)(PH-9 NH4OH)

Mobile Phase B: Acetonitrile

Flow rate: 25 ml/min

Diluent: Mobile phase

Method: 0/10,1/10,10/45,11/45,11.5/100,15/100

Column Temp ° C.: Ambient

Solubility: THF+MeOH

Fraction volume: 250 ml

The collected fractions were lyophilized. The residue was dissolved in water (5 ml) and acidified with acetic acid. After extraction with EtOAc, the organic phase was dried over anhydrous $Na_2SO_4$ and concentrated under reduced pressure to afford the title compound (65 mg, 21.90% yield) as an off-white solid.

LCMS (c): Rt=3.09 min, M/z=579.45 $(M+H)^+$

1H NMR (CDCl3, ppm): 7.55 (m, 1H), 7.15 (m, 1H), 7.05 (m, 1H), 7 (m, 1H), 6.85 (m, 1H), 6.65 (m, 2H), 5.05 (s, 2H), 4.85 (m, 2H), 4.7 (m, 2H), 3.7 (m, 2H), 3.55 (m, 1H), 3.4 (m, 2H), 3 (m, 2H), 2.7 (m, 2H), 2.35 (s, 3H), 2 to 1.9 (m, 8H), 1.8 (m, 2H)

Example 18

1-(6-(3,5-difluoro-2-((2-methyl-6-(1-(oxetan-3-yl)piperidin-4-yl)pyridin-3-yl)methoxy)phenyl)pyridin-2-yl)piperidine-4-carboxylic acid, sodium salt

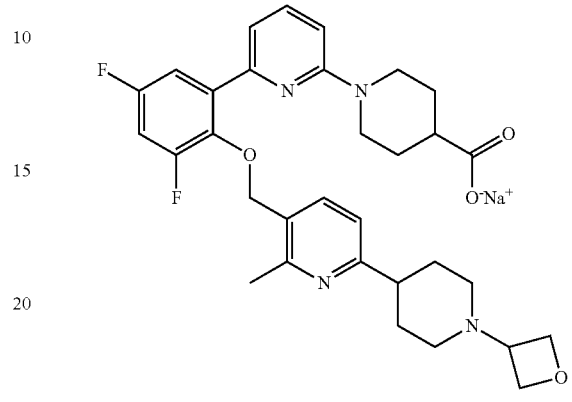

To a solution of 1-(6-(3,5-difluoro-2-((2-methyl-6-(1-(oxetan-3-yl)piperidin-4-yl)pyridin-3-yl)methoxy)phenyl)pyridin-2-yl)piperidine-4-carboxylic acid (65 mg, 0.112 mmol) in water (7 mL) was added NaOH (4.49 mg, 0.112 mmol) in water (5 mL). The reaction mixture was stirred at room temperature for 20 minutes and then was transferred to a lyophilization flask and lyophilized for 20 hours to afford the title compound (67 mg, 97% yield) as an off-white solid.

LCMS (c): Rt=3.06 min, M/z=579.43 $(M+H)^+$

1H NMR (DMSO d6 ppm): 7.5 (dd, 1H), 7.43 (d, 1H), 7.36 (m, 2H), 7.03 (2d, 2H), 6.8 (d, 1H), 4.87 (s, 2H), 4.53 (t, 2H), 4.44 (t, 2H), 4.16 (m, 1H), 4.13 (m, 1H), 3.39 (m, 1H), 2.88 (m, 2H), 2.77 (m, 2H), 2.58 (m, 1H), 2.37 (s, 3H), 2.08 (m, 1H), 1.88 to 1.68 (m, 8H), 1.55 to 1.46 (m, 2H)

Example 19 ethyl 1-(6-(3,5-difluoro-2-((2-methyl-6-(1-(tetrahydrofuran-3-yl)piperidin-4-yl)pyridin-3-yl)methoxy)phenyl)pyridin-2-yl)piperidine-4-carboxylate

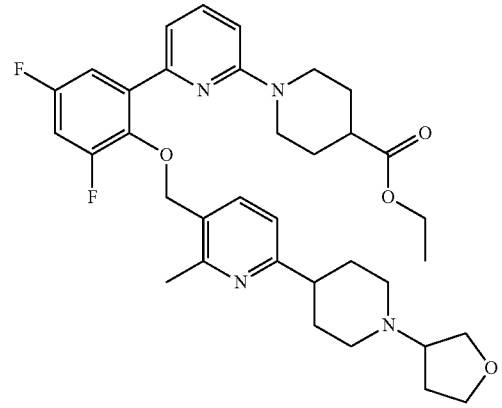 [SMILES: CCOC(=O)C1CCN(c2cccc(-c3cc(F)cc(F)c3OCc3ccc(C4CCN(C5CCOC5)CC4)nc3C)n2)CC1]

To a suspension of molecular sieves in methanol (2 ml) stirred under nitrogen at 0° C., were added ethyl 1-(6-(3,5-difluoro-2-((2-methyl-6-(piperidin-4-yl)pyridin-3-yl)methoxy)phenyl)pyridin-2-yl)piperidine-4-carboxylate (350 mg, 0.636 mmol) and dihydrofuran-3(2H)-one (65.7 mg, 0.763 mmol) in methanol (2 mL) and then 2 drops of acetic acid. The reaction mixture was stirred at room temperature for 2 hours and then, NaCNBH$_4$ (39.9 mg, 0.636 mmol) was added. The reaction mixture was stirred at 50° C. for 16 hours and then was diluted with water (10 mL) and extracted with EtOAc (3×20 mL). The combined organic phase was washed with brine solution (25 mL), dried over anhydrous Na$_2$SO$_4$ and concentrated under reduced pressure. The residue was purified by column chromatography (silica gel 100-200 mesh, eluted with 10% EtOAc in Hexane). The collected fractions were concentrated under reduced pressure to afford the title compound (300 mg, 73.3% yield).

LCMS (c): Rt=4.09 min, M/z=621.46 (M+H)$^+$

Example 20

1-(6-(3,5-difluoro-2-((2-methyl-6-(1-(tetrahydrofuran-3-yl)piperidin-4-yl)pyridin-3-yl)methoxy)phenyl)pyridin-2-yl)piperidine-4-carboxylic acid

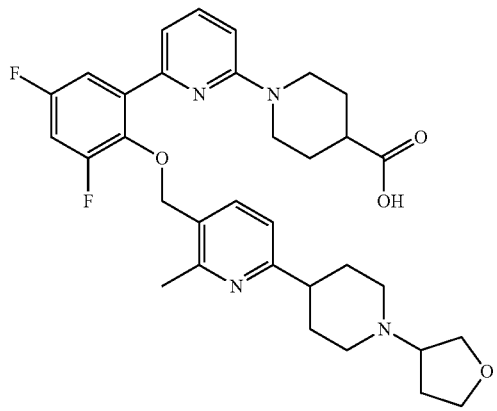 [SMILES: Cc1nc(C2CCN(C3CCOC3)CC2)ccc1COc1c(F)cc(F)cc1-c1cccc(N2CCC(C(=O)O)CC2)n1]

To a solution of ethyl 1-(6-(3,5-difluoro-2-((2-methyl-6-(1-(tetrahydrofuran-3-yl)piperidin-4-yl)pyridin-3-yl)methoxy)phenyl)pyridin-2-yl)piperidine-4-carboxylate (310 mg, 0.499 mmol) in ethanol (5 mL) stirred under nitrogen, was added a solution of NaOH (30.0 mg, 0.749 mmol) in water (2 mL) dropwise during 5 minutes. The reaction mixture was stirred at room temperature for 16 hours and then was diluted with water (10 mL) and the pH was adjusted to 5 with a citric acid solution. After extraction with 10% MeOH/CH$_2$Cl$_2$ (9/1) (3×20 mL), the combined organic phase was dried over anhydrous Na$_2$SO$_4$ and concentrated under reduced pressure. The residue was purified by Prep—HPLC. Prep-HPLC purification conditions:
Prep HPLC Column:
  kromasil (21.1×250 mm) 10 µ
  Mobile Phase A: 10 mm AMMONIUM BICARBONATE (Aq)(PH9) Mobile
  Phase B: Acetonitrile
  Flow rate: 20 ml/min
  Diluent: MEOH+THF+CENTRIFUGE
  Method: 0/10,1/10,10/45,13/45,13.5/100,18/100
  Column Temp ° C.: Ambient Collected fractions were concentrated under reduced pressure. The residue was dissolved in water (5 ml) and acidified with acetic acid. After extraction with EtOAc, the organic phase was dried over anhydrous Na$_2$SO$_4$ and concentrated under reduced pressure to afford the title compound (78 mg, 0.131 mmol, 26.2% yield) as an off-white solid.

LCMS (c): Rt=3.03 min, M/z=593.43 (M+H)$^+$

Example 21

1-(6-(3,5-difluoro-2-((2-methyl-6-(1-(tetrahydrofuran-3-yl)piperidin-4-yl)pyridin-3-yl)methoxy)phenyl)pyridin-2-yl)piperidine-4-carboxylic acid, sodium salt

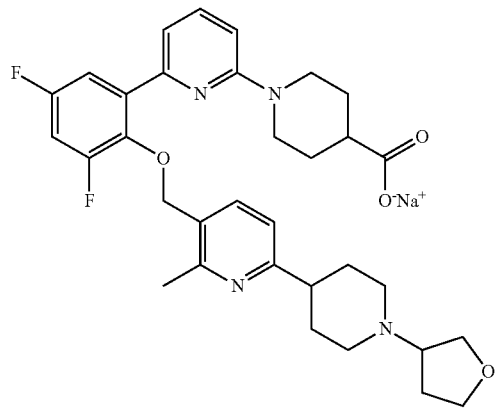

To a solution of 1-(6-(3,5-difluoro-2-((2-methyl-6-(1-(tetrahydrofuran-3-yl)piperidin-4-yl)pyridin-3-yl)methoxy)phenyl)pyridin-2-yl)piperidine-4-carboxylic acid (78 mg, 0.132 mmol) in Water (7 mL) was added NaOH (5.26 mg, 0.132 mmol) in Water (5 mL). The reaction mixture was stirred at room temperature for 20 minutes and then was transferred to a lyophilization flask and lyophilized for 20 hours to afford the title compound (75 mg, 91% yield) as an off-white solid.

LCMS (c): Rt=3.04 min, M/z=593.43 (M+H)$^+$

1H NMR: (DMSO d6 ppm): 7.5 (dd, 1H), 7.42 (d, 1H), 7.4 to 7.32 (m, 2H), 7.02 (m, 2H), 6.8 (d, 1H), 4.87 (s, 2H), 4.16 (m, 1H), 4.13 (m, 1H), 3.78 (m, 2H), 3.65 (q, 1H), 3.47 (dd, 1H), 2.98 (m, 1H), 2.9 (m, 3H), 2.78 (m, 1H), 2.56 (m, 1H), 2.36 (s, 3H), 2.1 to 1.96 (m, 4H), 1.8 to 1.64 (m, 7H), 1.51 (m, 2H)

Example 22 ethyl 1-(6-(3,5-difluoro-2-((2-methyl-6-(1-((tetrahydrofuran-3-yl)methyl)piperidin-4-yl)pyridin-3-yl)methoxy)phenyl)pyridin-2-yl)piperidine-4-carboxylate

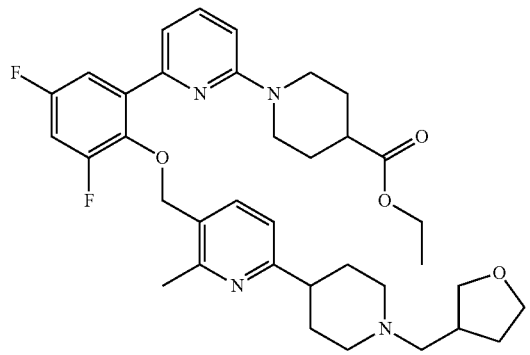 [SMILES: CCOC(=O)C1CCN(c2cccc(-c3cc(F)cc(F)c3OCc3ccc(C4CCN(CC5CCOC5)CC4)nc3C)n2)CC1]

To a suspension of molecular sieves in methanol (5 mL) at 0° C. was added ethyl 1-(6-(3,5-difluoro-2-((2-methyl-6-(piperidin-4-yl)pyridin-3-yl)methoxy)phenyl)pyridin-2-yl)piperidine-4-carboxylate (300 mg, 0.545 mmol) and tetrahydrofuran-3-carbaldehyde (65.5 mg, 0.654 mmol) in Methanol (5 mL). The reaction mixture was stirred under nitrogen at 0° C. for 2 hours. Then NaCNBH$_4$ (34.2 mg, 0.545 mmol) was added and the reaction mixture was stirred at 50° C. for 16 hours, then was diluted with water (10 mL) and extracted with EtOAc. The organic phase was dried over anhydrous Na$_2$SO$_4$ and concentrated under reduced pressure. The residue was purified by column chromatography (silica gel 100-200 mesh, eluted with 10% EtOAc in Hexane). Collected fractions were concentrated under reduced pressure to afford the title compound (300 mg, 86% yield).

LCMS (a): Rt=2.11 min, M/z=635.47 (M+H)$^+$

Example 23

1-(6-(3,5-difluoro-2-((2-methyl-6-(1-((tetrahydrofuran-3-yl)methyl)piperidin-4-yl)pyridin-3-yl)methoxy)phenyl)pyridin-2-yl)piperidine-4-carboxylic acid

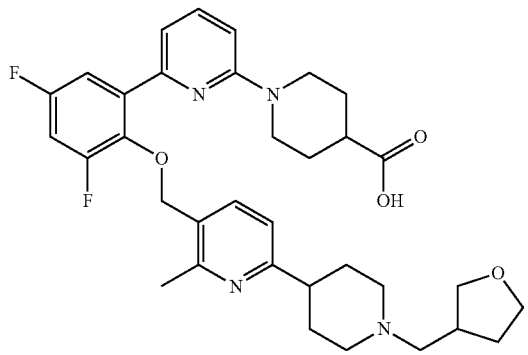 [SMILES: Cc1nc(C2CCN(CC3CCOC3)CC2)ccc1COc1c(F)cc(F)cc1-c1cccc(N2CCC(C(=O)O)CC2)n1]

To a solution of ethyl 1-(6-(3,5-difluoro-2-((2-methyl-6-(1-((tetrahydrofuran-3-yl)methyl)piperidin-4-yl)pyridin-3-yl)methoxy)phenyl)pyridin-2-yl)piperidine-4-carboxylate (300 mg, 0.473 mmol) in Ethanol (3 mL) was added NaOH (37.8 mg, 0.945 mmol) in water (1 mL). The reaction mixture was stirred at room temperature for 16 hours, and then was diluted with water (10 mL) and the pH was adjusted to 4 with a citric acid solution. After extraction with MeOH/CH$_2$Cl$_2$ (9/1), the organic phase was dried over anhydrous Na$_2$SO$_4$, and concentrated under reduced pressure. The residue was purified by Prep-HPLC. Prep-HPLC purification conditions:
Prep HPLC Column:
 kromasil (250*21.2*10 u)
 Mobile Phase: MP-A: 10 mM Ammonium Bicarbonate (Aq) MP-B: Acetonitrile
 Flow rate: 20 ml/min
 Solubility: H2O+THF
 Method: 0/20,10/50,15/50,15.1/20,20/20
 Column Temp ° C.: Ambient
 Fraction volume: 150 ml The collected fractions were lyophilized and the residue was dissolved in water (5 ml) and acidified with acetic acid. After extraction with EtOAc, the organic phase was dried over anhydrous Na$_2$SO$_4$ and concentrated under reduced pressure to afford the title compound (60 mg, 19.66% yield).

LCMS (c): Rt=3.03 min, M/z=607.42 (M+H)$^+$

Example 24

1-(6-(3,5-difluoro-2-((2-methyl-6-(1-((tetrahydrofuran-3-yl)methyl)piperidin-4-yl)pyridin-3-yl)methoxy)phenyl)pyridin-2-yl)piperidine-4-carboxylic acid, sodium salt

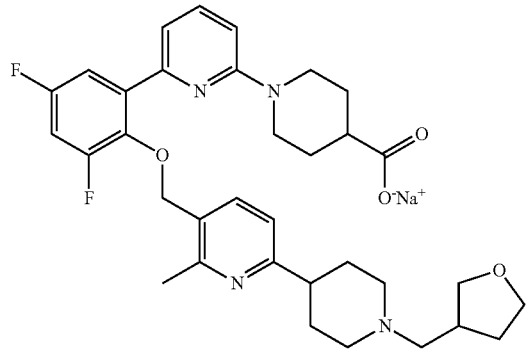

To a solution of 1-(6-(3,5-difluoro-2-((2-methyl-6-(1-((tetrahydrofuran-3-yl)methyl)piperidin-4-yl)pyridin-3-yl)methoxy)phenyl)pyridin-2-yl)piperidine-4-carboxylic acid (58 mg, 0.096 mmol) in Water (7 mL) was added NaOH (3.82 mg, 0.096 mmol) in Water (5 mL). The reaction mixture was stirred at room temperature for 20 minutes and then was transferred to a lyophilization flask and lyophilized for 20 hours to afford the title compound (55 mg, 91% yield) as an off-white solid.

LCMS (c): Rt=3.04 min, M/z=607.48 (M+H)$^+$

1H NMR (DMSO d6 ppm): 7.5 (dd, 1H), 7.42 (d, 1H), 7.38 (m, 2H), 7.02 (d, 2H), 6.8 (d, 1H), 4.87 (s, 2H), 4.16 (m, 1H), 4.13 (m, 1H), 3.71 (m, 2H), 3.6 (q, 1H), 3.38 (m, 1H), 3 to 2.85 (m, 4H), 2.55 (m, 1H), 2.43 (m, 1H), 2.36 (s, 3H), 2.26 (m, 2H), 2.1 to 1.9 (m, 4H), 1.8 to 1.65 (m, 6H), 1.56 to 1.46 (m, 3H)

Example 25 ethyl 1-(6-(2-(((6-(1-(cyanomethyl)piperidin-4-yl)-2-methylpyridin-3-yl)methoxy)-3,5-difluorophenyl)pyridin-2-yl)piperidine-4-carboxylate

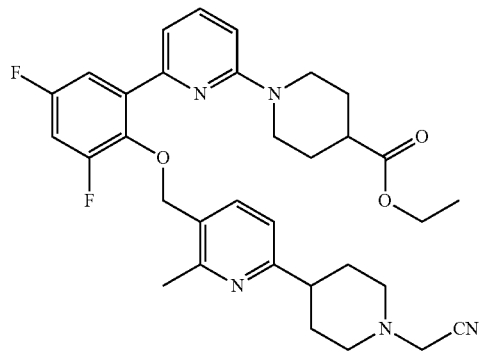 [SMILES: CCOC(=O)C1CCN(c2cccc(-c3cc(F)cc(F)c3OCc3ccc(C4CCN(CC#N)CC4)nc3C)n2)CC1]

To a solution of ethyl 1-(6-(3,5-difluoro-2-((2-methyl-6-(piperidin-4-yl)pyridin-3-yl)methoxy)phenyl)pyridin-2-yl)piperidine-4-carboxylate (500 mg, 0.908 mmol) in acetone (5 mL) stirred under nitrogen, were added $Cs_2CO_3$ (740 mg, 2.270 mmol) and 2-chloroacetonitrile (82 mg, 1.090 mmol). The reaction mixture was stirred at 70° C. for 16 hours, then diluted with water (10 mL) and extracted with EtOAc (3×20 mL). The organic phase was washed with brine solution (25 mL), dried over anhydrous $Na_2SO_4$ and concentrated under reduced pressure. The residue was purified by column chromatography (silica gel, eluted with 10% EtOAc in Hexane). Collected fractions were concentrated under reduced pressure to afford the title compound (250 mg, 40.2% yield).

LC/MS (a): Rt=2.31 min, M/z=590.42 (M+H)$^+$

Example 26

1-(6-(2-((6-(1-(cyanomethyl)piperidin-4-yl)-2-methylpyridin-3-yl)methoxy)-3,5-difluorophenyl)pyridin-2-yl)piperidine-4-carboxylic acid

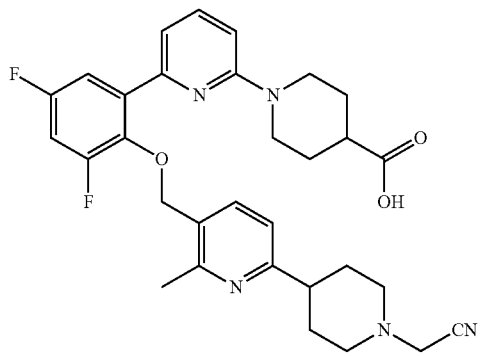 [SMILES: Cc1nc(C2CCN(CC#N)CC2)ccc1COc1c(F)cc(F)cc1-c1cccc(N2CCC(C(=O)O)CC2)n1]

To a solution of ethyl 1-(6-(2-((6-(1-(cyanomethyl)piperidin-4-yl)-2-methylpyridin-3-yl)methoxy)-3,5-difluorophenyl)pyridin-2-yl)piperidine-4-carboxylate (250 mg, 0.424 mmol) in EtOH (5 mL) stirred under nitrogen at 0° C. was added a solution of NaOH (20.35 mg, 0.509 mmol) in Water (2 mL) dropwise during 15 min. The reaction mixture was stirred at 0° C. for 16 hours, then concentrated under reduced pressure and diluted with water (10 mL). The aqueous phase was acidified with acetic acid (pH adjusted to ~5) and the resulting precipitate was filtered and washed with pentane. The solid was purified by HPLC.
Prep-HPLC Purification Conditions:
  Column: Xbridge (19×150 mm)
  Mobile Phase: Mobile Phase A: 10 mm AMMONIUM BICARBONATE
  Mobile Phase B: Acetonitrile
  Flow rate: 30 ml/min
  Diluent: Mobile phase
  Method: 0/10,1/10,10/45,11/45,11.5/100,15/100
  Column Temp ° C.: Ambient
  Solubility: ACN+THF+MeOH
The collected fractions were concentrated under reduced pressure to remove $CH_3CN$ and then the aqueous phase was acidified with acetic acid (pH adjusted to ~5). After extraction with EtOAc, the organic phase was dried over anhydrous $Na_2SO_4$ and concentrated under reduced pressure. The product was further purified by Prep-TLC (silica gel GF 254, eluted with 8% MEOH in $CH_2Cl_2$). The title compound was obtained (40 mg, 16.48% yield) as an off white solid.

LC/MS (b): Rt=4.48 min, M/z=562.35 (M+H)$^+$

Example 27

1-(6-(2-((6-(1-(cyanomethyl)piperidin-4-yl)-2-methylpyridin-3-yl)methoxy)-3,5-difluorophenyl)pyridin-2-yl)piperidine-4-carboxylic acid, Sodium salt

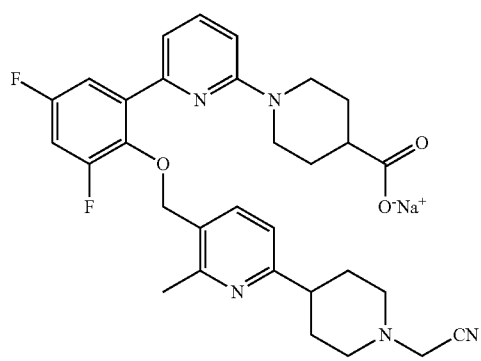

To a solution of 1-(6-(2-((6-(1-(cyanomethyl)piperidin-4-yl)-2-methylpyridin-3-yl)methoxy)-3,5-difluorophenyl)pyridin-2-yl)piperidine-4-carboxylic acid (40 mg, 0.071 mmol) in water (3 mL) was added sodium bicarbonate (5.98 mg, 0.071 mmol) in water (2 mL). The reaction mixture was stirred at room temperature for 20 minutes and then was transferred to a lyophilization flask and lyophilized for 20 hours to afford the title compound (31 mg, 68.3% yield) as an off white solid.

LC/MS (e): Rt=3.11 min, M/z=562 (M+H)$^+$

1H NMR (DMSO-d6, ppm): 7.51 (dd, 1H), 7.44 (d, 1H), 7.36 (m, 2H), 7.03 (t, 2H), 6.8 (d, 1H), 4.87 (s, 2H), 4.16 (m, 1H), 4.13 (m, 1H), 3.73 (s, 2H), 2.89 (m, 4H), 2.56 (m, 1H), 2.37 (s, 3H), 2.27 (m, 2H), 2.1 (m, 1H), 1.86 to 1.7 (m, 6H), 1.51 (m, 2H)

Example 28 ethyl 1-(6-(3,5-difluoro-2-((2-methyl-6-(1-(oxetane-3-carbonyl)piperidin-4-yl)pyridin-3-yl)methoxy)phenyl)pyridin-2-yl)piperidine-4-carboxylate

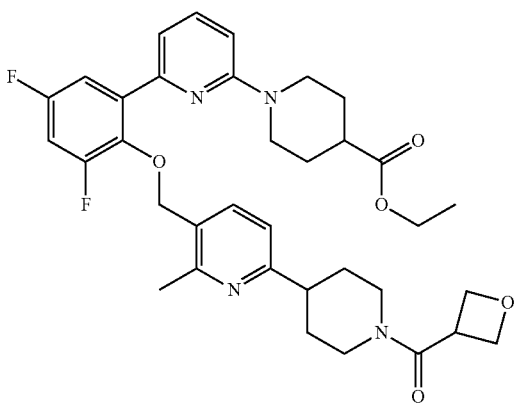 [SMILES: CCOC(=O)C1CCN(c2cccc(-c3cc(F)cc(F)c3OCc3ccc(C4CCN(C(=O)C5COC5)CC4)nc3C)n2)CC1]

To a solution of oxetane-3-carboxylic acid (111 mg, 1.090 mmol) in DMF (4 mL) was added HATU (621 mg, 1.634 mmol) and the reaction mixture was stirred at room temperature for 5 minutes. After cooling, ethyl 1-(6-(3,5-difluoro-2-((2-methyl-6-(piperidin-4-yl)pyridin-3-yl)methoxy)phenyl)pyridin-2-yl)piperidine-4-carboxylate (600 mg, 1.090 mmol) and then DIPEA (0.571 mL, 3.27 mmol) were slowly added and the resulting reaction mixture was stirred at 25° C. for 12 hours and then was diluted with cold water (60 mL) and extracted with EtOAc (3×50mL). The combined organic phase was washed with brine solution (80 mL), dried over anhydrous Na₂SO₄ and concentrated under reduced pressure. The residue was purified by column chromatography (silica gel, eluted with EtOAc). Collected fractions were concentrated under reduced pressure to afford the title compound (250 mg, 25.8% yield) as colorless sticky liquid.

LCMS (f): Rt=5.81 min, M/z=634.9 (M+H)⁺

Example 29

1-(6-(3,5-difluoro-2-((2-methyl-6-(1-(oxetane-3-carbonyl)piperidin-4-yl)pyridin-3-yl)methoxy)phenyl)pyridin-2-yl)piperidine-4-carboxylic acid To a solution of ethyl 1-(6-(3,5-difluoro-2-((2-methyl-6-(1-(oxetane-3-carbonyl)piperidin-4-yl)pyridin-3-yl)methoxy)phenyl)pyridin-2-yl)piperidine-4-carboxylate (250 mg, 0.394 mmol) in EtOH (3 mL) and Water (0.3 mL) was added NaOH (0.788 mL, 0.788 mmol) dropwise. The resulting mixture was stirred at 25° C. for 12 hours and then was acidified with a 10% citric acid solution (pH adjusted to 5) to get a colloid which was filtered and washed with water. The residue was purified by prep HPLC.

Prep HPLC Conditions:

MP-A: 5 Mm ammonium bicarbonate (Aq) MP-B: Acetonitrile

Column: Xterra RPC18 (19×250) mm 10 μ

Method: 0/10,1/10,10/50,12/50,12.5/100

Flow: 19 ml/min

Solubility: THF+CAN

The collected fractions were subjected to lyophilization to afford the title compound (80 mg, 32.9% yield) as white solid.

LCMS (a): Rt=1.80 min, M/z=607.26 (M+H)⁺

Example 30

1-(6-(3,5-difluoro-2-((2-methyl-6-(1-(oxetane-3-carbonyl)piperidin-4-yl)pyridin-3-yl)methoxy)phenyl)pyridin-2-yl)piperidine-4-carboxylic acid, Sodium salt,

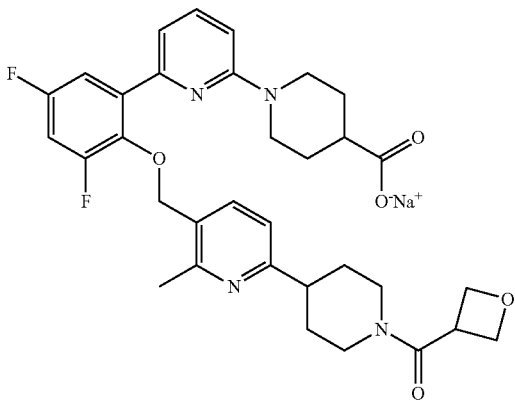

To a solution of 1-(6-(3,5-difluoro-2-((2-methyl-6-(1-(oxetane-3-carbonyl)piperidin-4-yl)pyridin-3-yl)methoxy)phenyl)pyridin-2-yl)piperidine-4-carboxylic acid (117 mg, 0.193 mmol) in Water (5 mL) was added sodium bicarbonate (16.20 mg, 0.193 mmol) in water (2 mL). The reaction mixture was stirred at 25° C. for 20 minutes and then was transferred to a lyophilization flask and lyophilized for 12 hours to afford the title compound (122 mg, 99% yield) as an off white solid.

LCMS (a): Rt=2.05 min, M/z=607.3 (M+H)⁺

1H NMR (DMSO-d6, ppm): 7.49 (dd, 1H), 7.44 (d, 1H), 7.4 to 7.33 (m, 2H), 7.04 (d, 1H), 7 (d, 1H), 6.79 (d, 1H), 4.87 (s, 2H), 4.7 (m, 3H), 4.63 (m, 1H), 4.5 (m, 1H), 4.13 (m, 3H), 3.45 (m, 1H), 3.03 (m, 1H), 2.86 (m, 3H), 2.67 (m, 1H), 2.36 (s, 3H), 1.95 (m, 1H), 1.83 to 1.73 (m, 4H), 1.57 to 1.47 (m, 4H)

Example 31 ethyl 1-(6-(3,5-difluoro-2-((6-(1-(2-hydroxyacetyl)piperidin-4-yl)-2-methylpyridin-3-1)methoxy)phenyl)pyridin-2-yl)piperidine-4-carboxylate

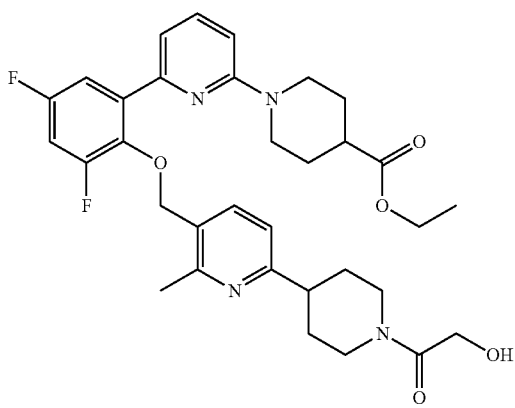 [SMILES: CCOC(=O)C1CCN(c2cccc(-c3cc(F)cc(F)c3OCc3ccc(C4CCN(C(=O)CO)CC4)nc3C)n2)CC1]

To a stirred solution of ethyl 1-(6-(3,5-difluoro-2-((2-methyl-6-(piperidin-4-yl)pyridin-3-yl)methoxy)phenyl)pyridin-2-yl)piperidine-4-carboxylate (600 mg, 1.090 mmol) in DMF (10 mL) were added 2-hydroxyacetic acid (83 mg, 1.090 mmol) and HATU (621 mg, 1.634 mmol). The reaction mixture was stirred at 0° C. for 30 minutes and then DIPEA (0.571 mL, 3.27 mmol) was added dropwise. The reaction mixture was stirred at 25° C. for 12 hours, then was diluted with cold water (60 mL) and extracted with EtOAc (3×50 mL). The combined organic phase was washed with brine solution (80 mL) dried over anhydrous sodium sulphate and concentrated under reduced pressure. The residue was purified by column chromatography (silica gel, eluted with EtOAc). The collected fractions were concentrated under reduced pressure to afford the title compound (260 mg, 32.1% yield) as colorless sticky liquid.

LCMS (a): Rt=2.18 min, M/z=609.20 (M+H)+

Example 32

1-(6-(3,5-difluoro-2-((6-(1-(2-hydroxyacetyl)piperidin-4-yl)-2-methylpyridin-3-yl)methoxy)phenyl)pyridin-2-yl)piperidine-4-carboxylic acid

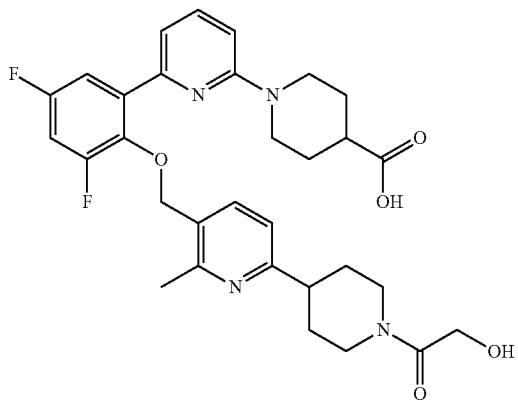

To a solution of ethyl 1-(6-(3,5-difluoro-2-((6-(1-(2-hydroxyacetyl)piperidin-4-yl)-2-methylpyridin-3-yl)methoxy)phenyl)pyridin-2-yl)piperidine-4-carboxylate (260 mg, 0.427 mmol) in EtOH (4 mL) and water (2 mL) was added NaOH (0.513 mL, 0.513 mmol). The reaction mixture was stirred at room temperature and monitored by TLC. After completion of the reaction, EtOH was evaporated under reduced pressure. The aqueous phase was acidified with a solution of citric acid 10% (pH adjusted to ~5). The resulting colloid precipitate was filtered, washed with water and dried. The product was purified by Prep. HPLC.

Prep. HPLC Conditions:

MP-A: 5 Mm ammonium bicarbonate(Aq) MP-B: Acetonitrile

Column: Xterra RPC18(19×250)mm 10 µ

Method: 0/10,1/10,10/50,12/50,12.5/100

Flow: 19 ml/min

Solubility: THF+ACN

The collected fractions were lyophilized to afford the title compound (72 mg, 28.7% yield) as white solid.

LCMS (a): Rt=1.75 min, M/z=581.23 (M+H)+

Example 33

1-(6-(3,5-difluoro-2-((6-(1-(2-hydroxyacetyl)piperidin-4-yl)-2-methylpyridin-3-yl)methoxy)phenyl)pyridin-2-yl)piperidine-4-carboxylic acid, Sodium salt

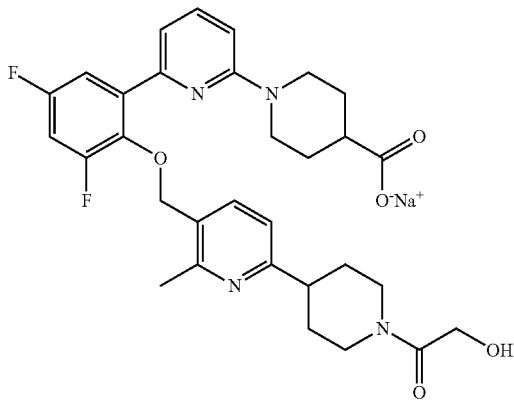

To a solution of 1-(6-(3,5-difluoro-2-((6-(1-(2-hydroxyacetyl)piperidin-4-yl)-2-methylpyridin-3-yl)methoxy)phenyl)pyridin-2-yl)piperidine-4-carboxylic acid (70 mg, 0.121 mmol) in water (5 mL) was added sodium bicarbonate (10.13 mg, 0.121 mmol) in water (2 mL). The reaction mixture was stirred at 25° C. for 20 minutes and then was transferred to a lyophilization flask and lyophilized for 12 hours to afford the title compound (100% yield) as an off white solid.

LC/MS (a): Rt=1.99 min, M/z=581.27 (M+H)+

1H NMR (DMSO-d6, ppm): 7.48 (dd, 1H), 7.37 (d, 1H), 7.34 (m, 2H), 6.99 (dd, 2H), 6.77 (d, 1H), 4.89 (s, 2H+m, 1H), 4.45 (m, 1H), 4.1 (m, 4H), 3.82 (m, 1H), 3.04 (m, 1H), 2.85 (m, 3H), 2.68 (m, 1H), 2.33 (s, 3H), 1.95 (m, 1H), 1.82 to 1.72 (m, 4H), 1.62 to 1.44 (m, 4H)

Intermediate 13: ethyl 1-(6-(2-((4-bromo-2-methylbenzyl)oxy)-3-chlorophenyl)pyridin-2-yl)piperidine-4-carboxylate

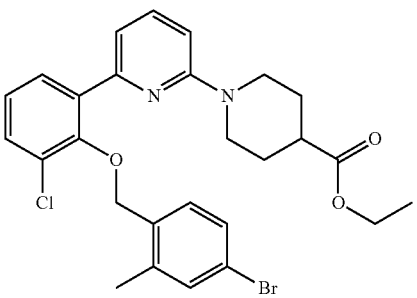 [SMILES: CCOC(=O)C1CCN(c2cccc(-c3cccc(Cl)c3OCc3ccc(Br)cc3C)n2)CC1]

To a solution of ethyl 1-(6-(3-chloro-2-hydroxyphenyl)pyridin-2-yl)piperidine-4-carboxylate (2.5 g, 6.93 mmol) and 4-bromo-1-(bromomethyl)-2-methylbenzene (2.195 g, 8.31 mmol) in Acetone (50 ml) stirred under nitrogen atmosphere, was added Cs2CO3 (4.51 g, 13.86 mmol). The reaction mixture was heated at 60° C. for 20 hours, then cooled and concentrated under reduced pressure. Water (50 mL) was added to the residue. After extraction with EtOAc (3×50 mL), the combined organic phase was washed with a saturated solution of NaCl (50 mL), dried over anhydrous Na$_2$SO$_4$ and concentrated under reduced pressure. The residue was purified by combiflash column chromatography (eluted with 6-8% EtOAc: Hexane). Collected fractions were concentrated under reduced pressure to afford the title compound (3.1 g, 81% yield) as a colorless gum.

LC/MS (b): Rt=2.8 min, M/z=545.25 (M+H)$^+$

Intermediate 14: tert-butyl 4-(4-((2-chloro-6-(6-(4-(ethoxycarbonyl)piperidin-1-yl)pyridin-2-yl)phenoxy)methyl)-3-methylphenyl)-5,6-dihydropyridine-1(2H)-carboxylate

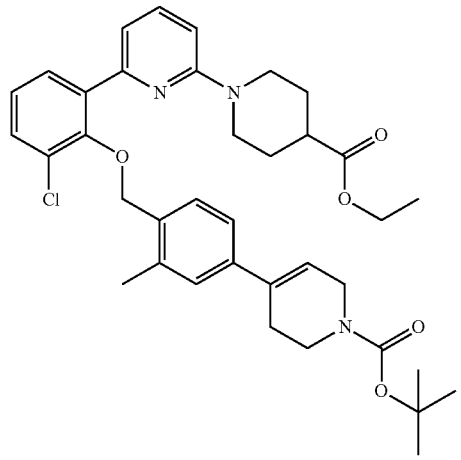 [SMILES: CCOC(=O)C1CCN(c2cccc(-c3cccc(Cl)c3OCc3ccc(C4=CCN(C(=O)OC(C)(C)C)CC4)cc3C)n2)CC1]

To a solution of ethyl 1-(6-(2-((4-bromo-2-methylbenzyl)oxy)-3-chlorophenyl)pyridin-2-yl)piperidine-4-carboxylate (2.6 g, 4.78 mmol) and tert-butyl 4-(4,4,5,5-tetramethyl-1,3,2-dioxaborolan-2-yl)-5,6-dihydropyridine-1(2H)-carboxylate (2.217 g, 7.17 mmol) in 1,2-Dimethoxyethane (75 mL) and Water (5 mL) under Argon atmosphere, was added Na$_2$CO$_3$ (1.013 g, 9.56 mmol). Argon was purged through the reaction mixture for 20 minutes and then tetrakis(triphenylphosphine)palladium(0) (0.552 g, 0.478 mmol) wad added. After purging for additional 5 minutes, the reaction mixture was heated at 100° C. for 16 hours, then cooled and filtered through a celite pad. The precipitate was washed with EtOAc (3×25 mL). The combined filtrate was concentrated under reduced pressure. The crude product was purified by column chromatography (non polar impurity was removed with 2-6% EtOAc in Hexane and the product was eluted with 8-10% EtOAc in Hexane). Collected fractions were concentrated under reduced pressure to afford the title compound (2.1 g, 65.8% yield) as pale yellow gum.

LC/MS (c): Rt=4.89 min, M/z=646.3 (M+H)$^+$

Intermediate 15: tert-butyl 4-(4-((2-chloro-6-(6-(4-(ethoxycarbonyl)piperidin-1-yl)pyridin-2-yl)phenoxy)methyl)-3-methylphenyl)piperidine-1-carboxylate

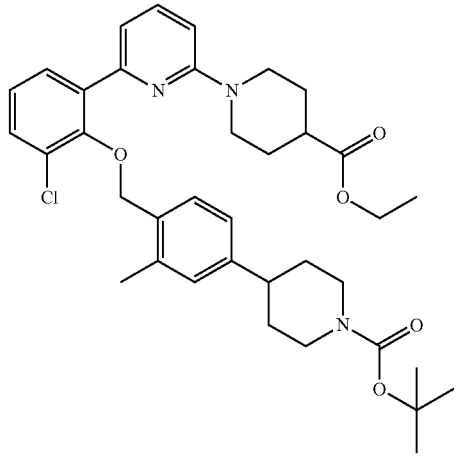 [SMILES: CCOC(=O)C1CCN(c2cccc(-c3cccc(Cl)c3OCc3ccc(C4CCN(C(=O)OC(C)(C)C)CC4)cc3C)n2)CC1]

To a solution of tert-butyl 4-(4-((2-chloro-6-(6-(4-(ethoxycarbonyl)piperidin-1-yl)pyridin-2-yl)phenoxy)methyl)-3-methylphenyl)-5,6-dihydropyridine-1(2H)-carboxylate (2.1 g, 3.25 mmol) in EtOAc (10 mL) stirred at 25° C. under nitrogen atmosphere was added carefully platinum (IV) oxide (0.369 g, 1.625 mmol). The reaction mixture was then stirred under Hydrogen pressure at 25° C. for 16 hours. The catalyst was filtered off on a celite pad and washed with EtOAc (3×25 mL). The filtrate was concentrated under reduced pressure to afford the title compound (1.7 g, 63.1% yield) as pale yellow gum.

LC/MS (c): Rt=4.95 min, M/z=648.38 (M+H)$^+$

Intermediate 16: ethyl 1-(6-(3-chloro-2-((2-methyl-4-(piperidin-4-yl)benzyl)oxy)phenyl)-pyridin-2-yl)piperidine-4-carboxylate

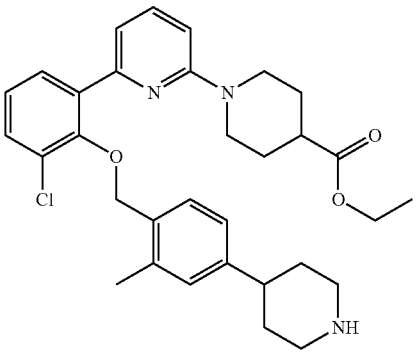 [SMILES: CCOC(=O)C1CCN(c2cccc(-c3cccc(Cl)c3OCc3ccc(C4CCNCC4)cc3C)n2)CC1]

To a solution of tert-butyl 4-(4-((2-chloro-6-(6-(4-(ethoxycarbonyl)piperidin-1-yl)pyridin-2-yl)phenoxy)methyl)-3-methylphenyl)piperidine-1-carboxylate (1.7 g, 2.62 mmol) in CH$_2$CL$_2$ (20 mL) stirred at 0° C. under nitrogen atmosphere was added dropwise TFA (1.01 mL, 13.11 mmol) in CH$_2$Cl$_2$ (5 mL). The reaction mixture was stirred at 0° C. for 4 hours and then was concentrated under reduced pressure. The residue was diluted with cold water (15 mL) and the aquous phase was basified with a saturated NaHCO$_3$ solution (to pH ~10) at 0° C. After extraction with CH$_2$Cl$_2$ (3×50 mL), the combined organic phase was washed with saturated NaCl (aq) solution (50 mL), dried over anhydrous Na$_2$SO$_4$ and concentrated under reduced pressure. The residue was purified by column chromatography (Al$_2$O$_3$), nonpolar impurity was removed with 50-70% EtOAc in Hexane and product was isolated with 10% MEOH in CH$_2$Cl$_2$. Collected fractions were concentrated under reduced pressure to afford the title compound (780 mg, 52.8% yield) as light brown gum.

LC/MS (a): Rt=2.07 min, M/z=548.34 (M+H)$^+$

Example 34 ethyl 1-(6-(3-chloro-2-((2-methyl-4-(1-(oxetan-3-yl) piperidin-4-yl)benzyl)oxy)phenyl)pyridin-2-yl)piperidine-4-carboxylate

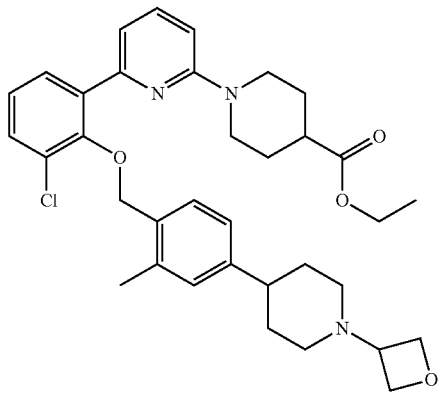 [SMILES: CCOC(=O)C1CCN(c2cccc(-c3cccc(Cl)c3OCc3ccc(C4CCN(C5COC5)CC4)cc3C)n2)CC1]

To a suspension of molecular sieve (4 Å, 250 mg) in MEOH (15 mL) stirred at 0° C. under nitrogen atmosphere, were added ethyl 1-(6-(3-chloro-2-((2-methyl-4-(piperidin-4-yl)benzyl)oxy)phenyl)pyridin-2-yl)piperidine-4-carboxylate (680 mg, 1.241 mmol) followed by oxetan-3-one (134 mg, 1.861 mmol). The reaction mixture was stirred for 2 hours maintaining the bath temperature at 0° C. Then sodium cyanoborohydride (195 mg, 3.10 mmol) was added at 0° C. and the reaction mixture was stirred at 0° C. for 30 minutes and then was heated at 50° C. for 16 hours and cooled. The reaction mixture was filtered through a celite pad, washed with Methanol (2×15 mL) and the filtrate was concentrated under reduced pressure. The residue was purified by flash column chromatography (eluted with EtOAc/hexane: 3/7 to EtOAc 100%). Collected fractions were concentrated under reduced pressure to afford the title compound (460 mg, 52.3% yield) as a colorless gum.

LC/MS (a): Rt=2.04 min, M/z=604.34 (M+H)$^+$

Example 35

1-(6-(3-chloro-2-((2-methyl-4-(1-(oxetan-3-yl) piperidin-4-yl)benzyl)oxy)phenyl)pyridin-2-yl)piperidine-4-carboxylic acid

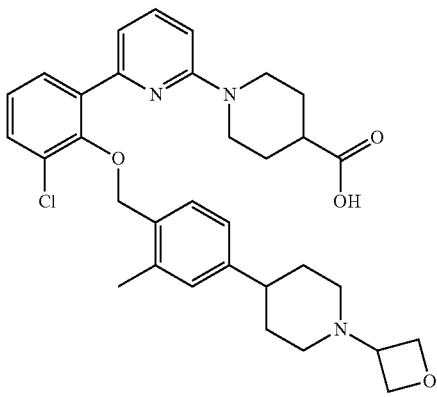 [SMILES: Cc1cc(C2CCN(C3COC3)CC2)ccc1COc1c(Cl)cccc1-c1cccc(N2CCC(C(=O)O)CC2)n1]

To a solution of ethyl 1-(6-(3-chloro-2-((2-methyl-4-(1-(oxetan-3-yl)piperidin-4-yl)benzyl)oxy)phenyl)pyridin-2-yl)piperidine-4-carboxylate (460 mg, 0.761 mmol) in EtOH (20 mL) stirred at 0° C. was added dropwise sodium hydroxide (2.284 mL of a solution 1M, 2.284 mmol). The reaction mixture was stirred at 25° C. for 16 hours and then concentrated under reduced pressure. After dilution with cold water (10 mL), the aqueous phase was acidified with a solution of citric acid 10% (pH adjusted to ~5) at 0° C. The resulting precipitate was filtered on a Buchner funnel and washed with water (2×mL) followed by n-pentane (3×15 mL) and dried. The product was purified by prep-HPLC.

Prep. HPLC Conditions:

Column: X Bridge C 18(150×4.6 mm, 3.5 µ)

Mobile Phase: A: 0.01 M Ammonium Bicarbonate B: ACN

Gradient: Time/% B: 0/10,1/10,10/50,15/50,18/98,20/98, 20.1/10,25/10

Column Temp: Ambient,

Flow Rate: 1.0 ml/min

Diluent: ACN

Collected volume: 800 mL

The collected fractions were collected and lyophilized to afford a white solid to which was added water (15 mL). The mixture was stirred for 15 minutes and the precipitate was filtered and dried under high vacuum to afford the title compound (138 mg, 30.2% yield) as an off white solid.

LC/MS (j): Rt=3.76 min, M/z=574.1 (M-H)$^+$

Example 36

1-(6-(3-chloro-2-((2-methyl-4-(1-(oxetan-3-yl) piperidin-4-yl)benzyl)oxy)phenyl)pyridin-2-yl)piperidine-4-carboxylic acid, Sodium salt

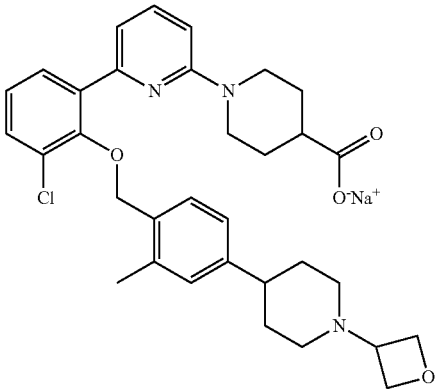

To a solution of 1-(6-(3-chloro-2-((2-methyl-4-(1-(oxetan-3-yl)piperidin-4-yl)benzyl)oxy)phenyl)pyridin-2-yl)piperidine-4-carboxylic acid (138 mg, 0.24 mmol) in Water (5 mL) was added dropwise sodium hydroxide (0.24 mL of a solution 1M, 0.24 mmol) and the reaction mixture was stirred at 25° C. for 20 minutes and then was transferred to a lyophilization flask and lyophilized for 16 hours to afford the title compound (150 mg, quantitative yield) as a white solid.

LC/MS (a): Rt=1.7 min, M/z=576.46 (M+H)$^+$

1H NMR (DMSO d6 ppm): 7.6 (dd, 1H), 7.51 (m, 2H), 7.25 (t, 1H), 7.13 (d, 1H), 7 (m, 2H), 6.94 (d, 1H), 6.78 (d, 1H), 4.7 (s, 2H), 4.53 (t, 2H), 4.44 (t, 2H), 4.14 (m, 2H), 3.4 (m, 1H), 2.87 (m, 2H), 2.78 (m, 2H), 2.44 (m, 1H), 2.15 (s, 3H), 1.96 (m, 1H), 1.87 to 1.61 (m, 8H), 1.51 (m, 2H)

Example 37 ethyl 1-(6-(3,5-difluoro-2-((2-methyl-4-(1-(oxetan-3-yl)piperidin-4-yl)benzyl)oxy)phenyl)pyridin-2-yl)piperidine-4-carboxylate

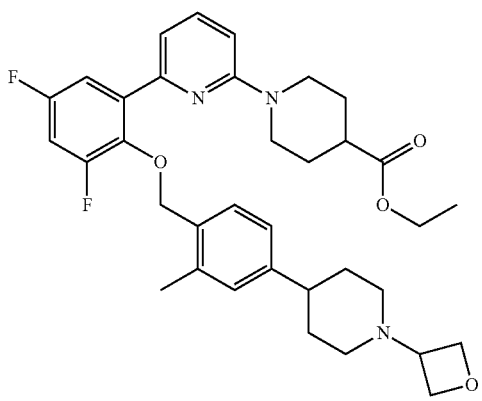 [SMILES: CCOC(=O)C1CCN(c2cccc(-c3cc(F)cc(F)c3OCc3ccc(C4CCN(C5COC5)CC4)cc3C)n2)CC1]

To a stirred solution of 4 Å molecular sieves (1 g) in MEOH (10 mL) were added ethyl 1-(6-(3,5-difluoro-2-(2-methyl-4-(piperidin-4-yl) benzyloxy) phenyl) pyridin-2-yl) piperidine-4-carboxylate (450 mg, 0.818 mmol) and Oxetan-3-one (0.057 mL, 0.98 mmol). The reaction mixture was stirred at 25° C. for 3 hours and then NaCNBH$_3$ (0.066 g, 1.06 mmol) was added portion wise. The reaction mixture was stirred at 50° C. for 12 hours and then was concentrated under reduced pressure. The crude residue was partitioned between EtOAc (20 mL) and water (10 mL). The organic phase was separated and the aqueous phase was further extracted with EtOAc (2×30 mL). The combined organic layer was washed with brine solution (10 mL), dried over anhydrous Na$_2$SO$_4$, and then concentrated under reduced pressure. The product was purified by column chromatography (eluted with CH$_2$Cl$_2$/MeOH 99/1 to 98/2 to removed non-polar impurities, and then eluted with CH$_2$Cl$_2$/MeOH 92/8). Collected fractions were concentrated under reduced pressure to afford the title compound (200 mg, 40% yield).

LC/MS (d): Rt=4.55 min, M/z=606.25(M+H)$^+$

Example 38

1-(6-(3,5-difluoro-2-((2-methyl-4-(1-(oxetan-3-yl) piperidin-4-yl)benzyl)oxy)phenyl)pyridin-2-yl)piperidine-4-carboxylic acid

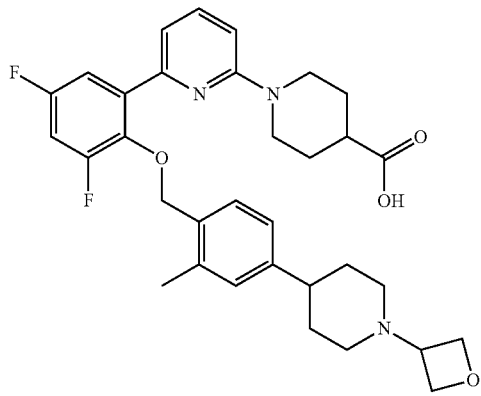 [SMILES: Cc1cc(C2CCN(C3COC3)CC2)ccc1COc1c(F)cc(F)cc1-c1cccc(N2CCC(C(=O)O)CC2)n1]

To a stirred solution of ethyl 1-(6-(3,5-difluoro-2-(2-methyl-4-(1-(oxetan-3-yl)piperidin-4-yl)benzyloxy)phenyl) pyridin-2-yl)piperidine-4-carboxylate (200 mg, 0.33 mmol) in EtOH (5 mL) at 0° C., was added a solution of NaOH (26 mg in 2 mL water, 0.65 mmol). The reaction mixture was stirred at 25° C. for 12 hours and then was concentrated under reduced pressure to remove EtOH. After dilution with water (10 mL), the pH was adjusted to 5 with a 5% citric acid solution. The resulting precipitated was filtered, washed with water (10 mL), then with n-pentane (10 mL), and was dried under vacuo to afford the title compound (190 mg, 100% yield) as off white solid.

LC/MS (a): Rt=1.96 min, M/z=578.62 (M+H)$^+$

Example 39

1-(6-(3,5-difluoro-2-((2-methyl-4-(1-(oxetan-3-yl)piperidin-4-yl)benzyl)oxy)phenyl)pyridin-2-yl)piperidine-4-carboxylic acid, Sodium salt

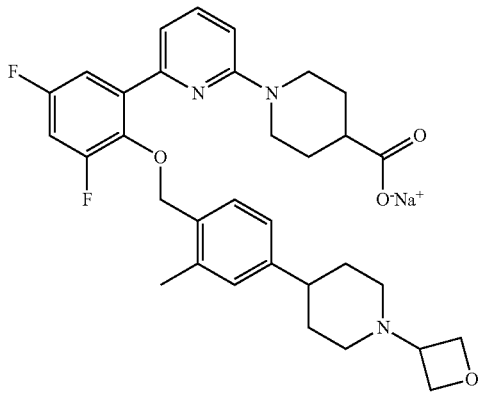

To a solution of 1-(6-(3,5-difluoro-2-((2-methyl-4-(1-(oxetan-3-yl)piperidin-4-yl)benzyl)oxy)phenyl)pyridin-2-yl)piperidine-4-carboxylic acid (165 mg, 0.286 mmol) in Water (7 mL) was added NaOH (11.42 mg, 0.286 mmol) in Water (5 mL). The reaction mixture was stirred at 25° C. for 20 minutes and then was transferred to a lyophilization flask and lyophilized for 12 hours to afford the title compound (158 mg, 91% yield) as an off white solid.

LC/MS (a): Rt=1.86 min, M/z=578.48 (M+H)$^+$

1H NMR (DMSO d6 ppm): 7.5 (dd, 1H), 7.36 (m, 2H), 7.1 (d, 1H), 7.03 (m, 3H), 6.8 (d, 1H), 4.82 (s, 2H), 4.53 (t, 2H), 4.44 (t, 2H), 4.14 (m, 2H), 3.4 (m, 1H), 2.88 (m, 2H), 2.79 (m, 2H), 2.44 (m, 1H), 2.2 (s, 3H), 1.95 (m, 1H), 1.84 (m, 2H), 1.78 to 1.48 (m, 8H)

Example 40 ethyl 1-(6-(3,5-difluoro-2-((2-methyl-4-(1-(tetrahydrofuran-3-yl)piperidin-4-yl)benzyl)oxy)phenyl)pyridin-2-yl)piperidine-4-carboxylate

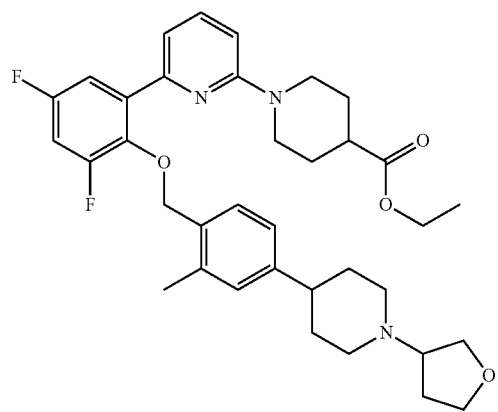 [SMILES: CCOC(=O)C1CCN(c2cccc(-c3cc(F)cc(F)c3OCc3ccc(C4CCN(C5CCOC5)CC4)cc3C)n2)CC1]

To a stirred solution of 4 Å molecular sieves (1 g) in MEOH (25 mL) were added ethyl 1-(6-(3,5-difluoro-2-(2-methyl-4-(piperidin-4-yl) benzyloxy) phenyl) pyridin-2-yl) piperidine-4-carboxylate (300 mg, 0.0546 mmol) and dihydrofuran-3(2H)-one (0.05 mL, 0.65 mmol). The reaction mixture was stirred at 25° C. for 3 hours. Then NaCNBH$_3$ (0.0446 g, 0.70 mmol) was added portion wise and the reaction mixture was stirred at 50° C. for 12 hours and then was concentrated under reduced pressure. The crude residue was partitioned between EtOAc (20 mL) and water (10 mL). The organic phase was separated and the aqueous phase was further extracted with EtOAc (2×30 mL). The combined organic layer was washed with brine solution (10 mL), dried over anhydrous Na$_2$SO$_4$, and then concentrated under reduced pressure. The product was purified by column chromatography (eluted with CH$_2$Cl$_2$/MeOH 99/1 to 98/2, then CH$_2$Cl$_2$/MeOH 92/8). The collected fractions were concentrated under reduced pressure to afford the title compound (220 mg, 88% yield) as gummy liquid.

LC/MS (a): Rt=2.3 min, M/z=620.4 (M+H)$^+$

Example 41

1-(6-(3,5-difluoro-2-((2-methyl-4-(1-(tetrahydrofuran-3-yl)piperidin-4-yl)benzyl)oxy)phenyl)pyridin-2-yl)piperidine-4-carboxylic acid

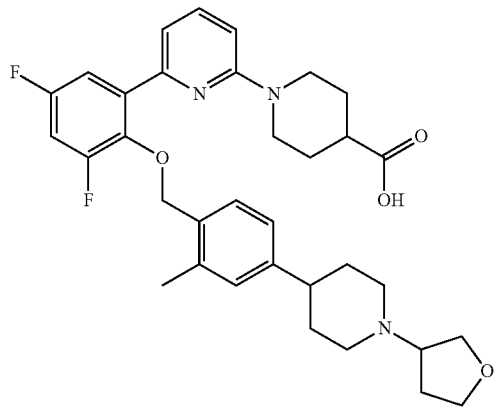

To a solution of ethyl 1-(6-(3,5-difluoro-2-((2-methyl-4-(1-(tetrahydrofuran-3-yl)piperidin-4-yl)benzyl)oxy)phenyl)pyridin-2-yl)piperidine-4-carboxylate (220 mg, 0.355 mmol) in EtOH (5 mL) stirred at 0° C., was added a solution of NaOH (28.4 mg, 0.710 mmol) in Water (2 mL). After addition the reaction mixture was stirred at 25° C. for 12 hours and then was concentrated under reduced pressure to remove EtOH. The crude was diluted with water (30 mL) the pH was adjusted to 5 with a 5% citric acid solution. The resulting precipitate was filtered, washed with water (10 mL), then with n-pentane (10 mL) and dried under vacuum to afford the title compound as off white solid (160 mg, 72.9% yield).

LC/MS (a): Rt=1.9 min, M/z=592.38 (M+H)$^+$

Example 42

1-(6-(3,5-difluoro-2-((2-methyl-4-(1-(tetrahydrofuran-3-yl)piperidin-4-yl)benzyl)oxy)phenyl)pyridin-2-yl)piperidine-4-carboxylic acid, Sodium salt

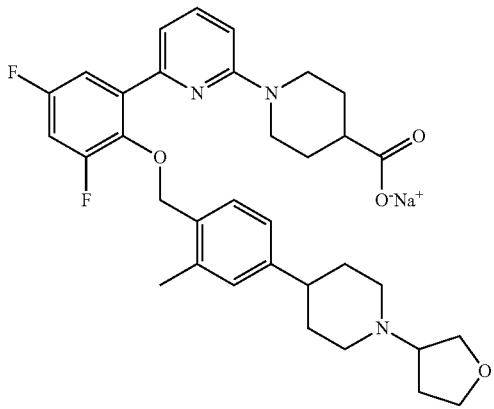

To a solution of 1-(6-(3,5-difluoro-2-((2-methyl-4-(1-(tetrahydrofuran-3-yl)piperidin-4-yl)benzyl)oxy)phenyl)pyridin-2-yl)piperidine-4-carboxylic acid (160 mg, 0.270 mmol) in Water (7 mL) was added NaOH (10.82 mg, 0.270 mmol) in Water (5 mL). The reaction mixture was stirred at 25° C. for 20 minutes and then was transferred to a lyophilization flask and lyophilized for 12 hours to afford the title compound (144 mg, 84% yield) as an off white solid.

LC/MS (a): Rt=1.9 min, M/z=592.48 (M+H)$^+$

1H NMR (DMSO d6 ppm): 7.51 (dd, 1H), 7.36 (m, 2H), 7.1 to 6.98 (m, 4H), 6.82 (d, 1H), 4.81 (s, 2H), 4.16 (m, 2H), 3.78 (m, 2H), 3.65 (m, 1H), 3.47 (m, 1H), 3 to 2.85 (m, 4H), 2.78 (m, 1H), 2.43 (m, 1H), 2.2 (s, 3H), 2.11 to 1.95 (m, 4H), 1.8 to 1.49 (m, 9H)

Example 43 ethyl 1-(6-(2-((4-(1-cyclopropylpiperidin-4-yl)-2-methylbenzyl)oxy)-3,5-difluorophenyl)pyridin-2-yl)piperidine-4-carboxylate

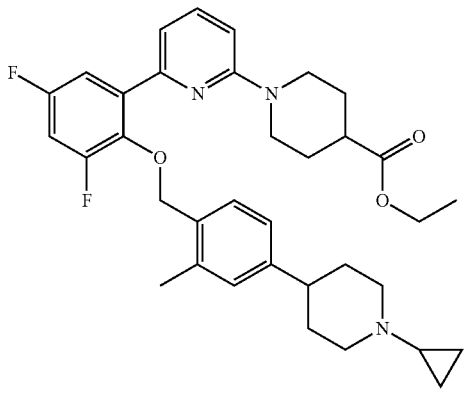 [SMILES: CCOC(=O)C1CCN(c2cccc(-c3cc(F)cc(F)c3OCc3ccc(C4CCN(C5CC5)CC4)cc3C)n2)CC1]

To a stirred solution of 4 Å molecular sieves (20 mg) in MEOH (5 mL) were added ethyl 1-(6-(3,5-difluoro-2-((2-methyl-4-(piperidin-4-yl)benzyl)oxy)phenyl)pyridin-2-yl)piperidine-4-carboxylate (200 mg, 0.364 mmol) and (1-ethoxycyclopropoxy)trimethylsilane (76 mg, 0.437 mmol). The reaction mixture was stirred at 25° C. for 3 hours. Then NaCNBH$_3$ (29.7 mg, 0.473 mmol) was added portion wise and the reaction mixture was stirred at 40° C. for 12 hours and then was concentrated under reduced pressure to remove MEOH. The crude residue was partitioned between EtOAc (20 mL) and water (5 mL). The organic phase was separated and the aqueous phase further extracted with EtOAc (2×20 mL). The combined organic phase was washed with brine solution (10 mL), then dried over Na$_2$SO$_4$, and concentrated under reduced pressure. The product was purified by column chromatography (eluted with 5-10% EtOAc in Petroleum ether gradient to removed non-polar impurities, then with EtOAc/Petroleum ether, 1/1). Collected fractions were concentrated under reduced pressure to afford the title compound (180 mg, 69.1% yield) as gummy solid.

LC/MS (b): Rt=4.92 min, M/z=590.24 (M+H)$^+$

Example 44

1-(6-(2-((4-(1-cyclopropylpiperidin-4-yl)-2-methylbenzyl)oxy)-3,5-difluorophenyl)pyridin-2-yl)piperidine-4-carboxylic acid

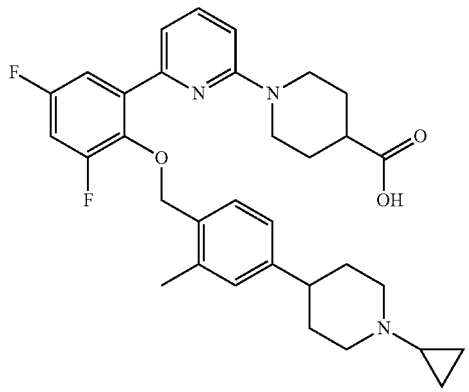 [SMILES: Cc1cc(C2CCN(C3CC3)CC2)ccc1COc1c(F)cc(F)cc1-c1cccc(N2CCC(C(=O)O)CC2)n1]

To a stirred solution of ethyl 1-(6-(2-((4-(1-cyclopropylpiperidin-4-yl)-2-methylbenzyl)oxy)-3,5-difluorophenyl)pyridin-2-yl)piperidine-4-carboxylate (180 mg, 0.305 mmol) in EtOH (3 mL) was added NaOH (24.42 mg, 0.610 mmol) Water (1 mL). The reaction mixture was stirred at 0° C. for 30 minutes, then at 25° C. for 12 hours and then was concentrated under reduced pressure to remove Ethanol. The crude residue was diluted with water (10 mL) and the pH was adjusted to 5 with a 5% citric acid solution. The resulting precipitate was filtered, washed with water (10mL), then with n-pentane (10mL) and dried under vacuum. The product was purified by Prep-HPLC.

Prep-HPLC Conditions:
    Column: XBridge C18(19×150)mm 5 μ
    MP-A: 5 mM Ammonium Acetata (Aq) MP-B Acetonitrile
    Method: T/% B=0/10, 10/50,12/50, 12.5/100, 12/100, 12.5/47
    Flow: 19 ml/min
    Solubility: ACN+MeoH+THF
    Fraction volume: 250 ml Collected fractions were concentrated under reduced pressure to remove CH$_3$CN, and then the aqueous phase was extracted with EtOAc. The organic phase the was dried over anhydrous Na₂SO₄ and concentrated under reduced pressure to afford the title compound (75 mg, 42.8% yield) as off white solid.

LC/MS (e): Rt=3.76 min, M/z=560.52 (M-H)⁺

Example 45

1-(6-(2-((4-(1-cyclopropylpiperidin-4-yl)-2-methylbenzyl)oxy)-3,5-difluorophenyl)pyridin-2-yl)piperidine-4-carboxylic acid, Sodium salt

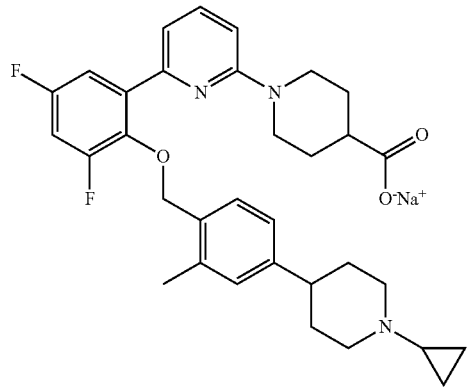

To a solution of 1-(6-(2-((4-(1-cyclopropylpiperidin-4-yl)-2-methylbenzyl)oxy)-3,5-difluorophenyl)pyridin-2-yl)piperidine-4-carboxylic acid (75 mg, 0.134 mmol) in Water (5 mL) was added sodium bicarbonate (11.22 mg, 0.134 mmol) in Water (2 mL). The reaction mixture was stirred at 25° C. for 20 minutes and then was transferred to a lyophilization flask and lyophilized for 12 hours to afford the title compound (70 mg, 89% yield) as an off white solid.

LCMS (e): Rt=3.42 min, M/z=562.47 (M+H)⁺

1H NMR (DMSO d6 ppm) 7.5 (dd, 1H), 7.35 (m, 2H), 7.1 to 6.98 (m, 4H), 6.8 (d, 1H), 4.81 (s, 2H), 4.15 (m, 1H), 4.12 (m, 1H), 3 (m, 2H), 2.88 (m, 2H), 2.44 (m, 1H), 2.23 (m, 2H), 2.2 (s, 3H), 1.98 (m, 1H), 1.77 (m, 2H), 1.68 (m, 2H), 1.63 to 1.57 (m, 2H), 1.55 to 1.45 (m, 4H), 0.41 (m, 2H), 0.3 (m, 2H)

Example 46 ethyl 1-(6-(3,5-difluoro-2-((4-(1-(2-methoxyethyl) piperidin-4-yl)-2-methylbenzyl)oxy)phenyl)pyridin-2-yl)piperidine-4-carboxylate

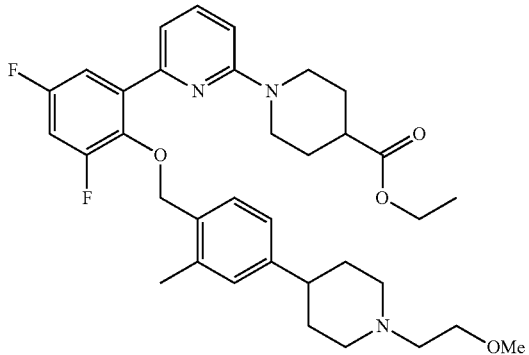 [SMILES: CCOC(=O)C1CCN(c2cccc(-c3cc(F)cc(F)c3OCc3ccc(C4CCN(CCOC)CC4)cc3C)n2)CC1]

To a solution of ethyl 1-(6-(3,5-difluoro-2-((2-methyl-4-(piperidin-4-yl)benzyl)oxy)phenyl)pyridin-2-yl)piperidine-4-carboxylate (300 mg,0.546 mmol) in Acetonitrile (10 mL) stirred at 0° C., were added Cs₂CO₃ (356 mg, 1.092 mmol) and 1-bromo-2-methoxyethane (114 mg, 0.819 mmol). The reaction mixture was stirred at 80° C. for 4 hours, then cooled to room temperature and concentrated under reduced pressure. The crude residue was partitioned between Ethyl acetate (25 mL) and water (20 mL). The organic phase was separated and the aqueous phase was further extracted with EtOAc (2×30 mL). The combined organic layer was washed with a sodium bicarbonate solution (10 mL), dried over Na₂SO₄, and then concentrated under reduced pressure to afford the title compound (200 mg; 30.2% yield) as a gummy solid.

LCMS (a): Rt=2.27 min, M/z=608.54 (M+H)⁺

Example 47

1-(6-(3,5-difluoro-2-((4-(1-(2-methoxyethyl)piperidin-4-yl)-2-methylbenzyl)oxy)phenyl)pyridin-2-yl) piperidine-4-carboxylic acid

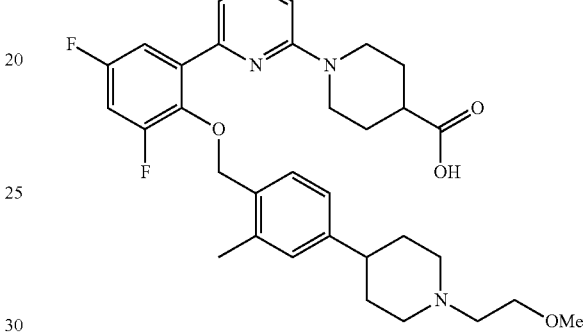

To a solution of ethyl 1-(6-(3,5-difluoro-2-((4-(1-(2-methoxyethyl)piperidin-4-yl)-2-methylbenzyl)oxy)phenyl) pyridin-2-yl)piperidine-4-carboxylate (200 mg, 0.329 mmol) in EtOH (5 mL) stirred at 0° C. was added a solution of NaOH (26.3 mg, 0.658 mmol) in Water (3 mL). The reaction mixture was stirred at 25° C. for 12 hours and then was concentrated under reduced pressure to remove EtOH. The crude residue was diluted with water (10 mL) and the pH adjusted to 5 with a 5% citric acid solution. The resulting precipitate was filtered, washed with water (10 mL), then with n-pentane (5 ml) and dried under vacuum to afford the title compound (170 mg, 88% yield) as off white solid.

LCMS (a): Rt=1.97 min, M/z=580.32 (M+H)⁺

Example 48

1-(6-(3,5-difluoro-2-((4-(1-(2-methoxyethyl)piperidin-4-yl)-2-methylbenzyl)oxy)phenyl)pyridin-2-yl) piperidine-4-carboxylic acid, Sodium salt

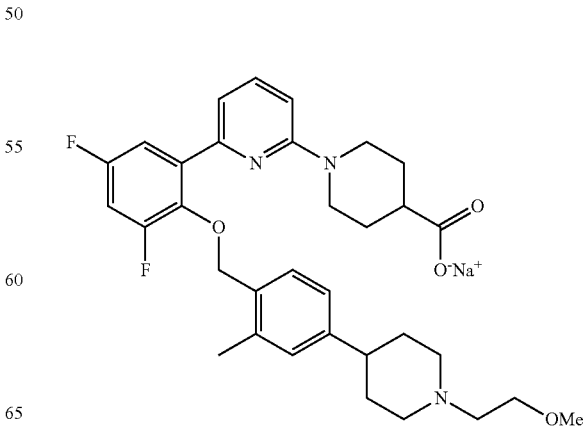

To a solution of 1-(6-(3,5-difluoro-2-((4-(1-(2-methoxyethyl)piperidin-4-yl)-2-methylbenzyl)oxy)phenyl)pyridin-2-yl)piperidine-4-carboxylic acid (170 mg, 0.293 mmol) in Water (7 mL) was added NaOH (11.73 mg, 0.293 mmol) in Water (5 mL). The reaction mixture was stirred at 25° C. for 20 minutes and then was transferred to a lyophilization flask and lyophilized for 12 hours to afford the title compound (180 mg, 97% yield) as an off white solid.

LCMS (a): Rt=1.96 min, M/z=580.53 (M+H)$^+$

1H NMR (DMSO d6 ppm): 7.54 (dd, 1H), 7.37 (m, 2H), 7.09 (m, 2H), 6.98 (m, 2H), 6.86 (d, 1H), 4.82 (s, 2H), 4.24 (m, 1H), 4.21 (m, 1H), 3.49 (m, 2H), 3.25 (s, 3H), 3.05 (m, 2H), 2.95 (m, 2H), 2.65 (m, 2H), 2.46 (m, 2H), 2.19 (s, 3H), 2.16 (m, 2H), 1.88 (m, 2H), 1.71 to 1.64 (m, 4H), 1.54 (m, 2H)

Example 49 ethyl 1-(6-(3,5-difluoro-2-((4-(1-(2-hydroxyethyl)piperidin-4-yl)-2-methylbenzyl)oxy)phenyl)pyridin-2-yl)piperidine-4-carboxylate

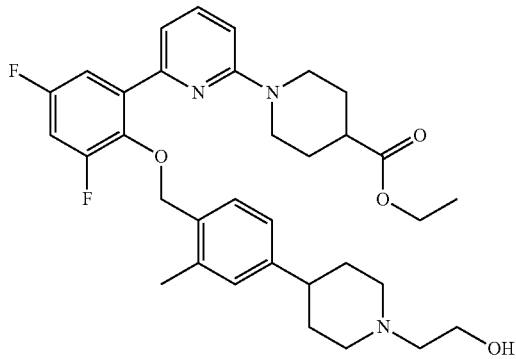 [SMILES: CCOC(=O)C1CCN(c2cccc(-c3cc(F)cc(F)c3OCc3ccc(C4CCN(CCO)CC4)cc3C)n2)CC1]

To a stirred solution of ethyl 1-(6-(3,5-difluoro-2-((2-methyl-4-(piperidin-4-yl)benzyl)oxy)phenyl)pyridin-2-yl)piperidine-4-carboxylate (400 mg, 0.728 mmol) in Acetonitrile (20 mL) at 0° C., were added 2-bromoethanol (109 mg, 0.873 mmol) and Cs$_2$CO$_3$ (474 mg, 1.455 mmol). The reaction mixture was stirred at 0° C. for 30 minutes, then at 80° C. for 24 hours and was diluted with water (10 mL). After extraction with EtOAc (3×30 mL), the combined organic phase was washed with water (2×20 mL), dried over anhydrous Na$_2$SO$_4$, and then concentrated under reduced pressure. The crude product was purified by column chromatography (eluted with CH$_2$Cl$_2$/MEOH, 99/1 to 98/2 to removed non-polar impurities, and then CH$_2$Cl$_2$/MEOH, 92/8). Collected fractions were concentrated under reduced pressure to afford the title compound (160 mg, 32.3% yield) as a gummy solid.

LC/MS (a): Rt=2.26 min, M/z=594.23 (M+H)$^+$

Example 50

1-(6-(3,5-difluoro-2-((4-(1-(2-hydroxyethyl)piperidin-4-yl)-2-methylbenzyl)oxy)phenyl)pyridin-2-yl)piperidine-4-carboxylic acid

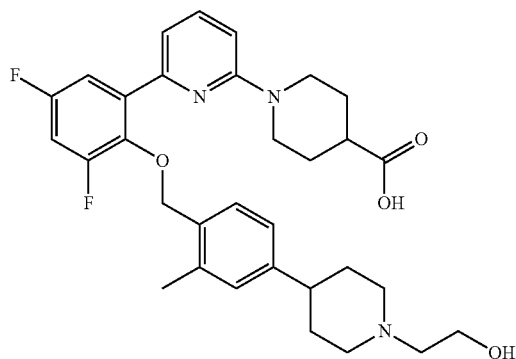 [SMILES: Cc1cc(C2CCN(CCO)CC2)ccc1COc1c(F)cc(F)cc1-c1cccc(N2CCC(C(=O)O)CC2)n1]

To a solution of ethyl 1-(6-(3,5-difluoro-2-((4-(1-(2-hydroxyethyl)piperidin-4-yl)-2-methylbenzyl)oxy)phenyl)pyridin-2-yl)piperidine-4-carboxylate (160 mg, 0.269 mmol) in EtOH (3 mL) stirred at 0° C., was added NaOH (21.56 mg, 0.539 mmol) in Water (1 mL). The reaction mixture was stirred at 0° C. for 30 minutes, then at 25° C. for 12 hours and was concentrated under reduced pressure to remove EtOH. The crude residue was diluted with water (10 mL) and the pH adjusted to 5 with a 5% citric acid solution. The resulting precipitate was filtered, washed with water, then n-pentane and dried under vacuum to afford the title compound (55 mg, 34.8% yield) as off white solid.

LC/MS (g): Rt=4.58 min, M/z=566.2 (M+H)$^+$

Example 51

1-(6-(3,5-difluoro-2-((4-(1-(2-hydroxyethyl)piperidin-4-yl)-2-methylbenzyl)oxy)phenyl)pyridin-2-yl)piperidine-4-carboxylic acid, Sodium salt

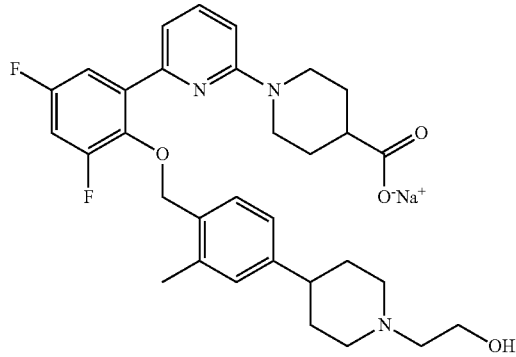

To a solution of 1-(6-(3,5-difluoro-2-((4-(1-(2-hydroxyethyl)piperidin-4-yl)-2-methylbenzyl)oxy)phenyl)pyridin-2-yl)piperidine-4-carboxylic acid (55 mg, 0.097 mmol) in Water (5 mL) was added NaOH (3.89 mg, 0.097 mmol) in Water (2 mL). The reaction mixture was stirred at 25° C. for 20 minutes and then was transferred to a lyophilization flask and lyophilized for 12 hours to afford the title compound (60 mg, quantitative yield) as an off white solid.

LC/MS (g): Rt=4.59 min, M/z=566.2 (M+H)$^+$

1H NMR (DMSO d6 ppm): 7.5 (dd, 1H), 7.35 (m, 2H), 7.08 (m, 2H), 7 (m, 2H), 6.8 (d, 1H), 4.8 (s, 2H), 4.4 (bs, 1H), 4.15 (m, 2H), 3.5 (t, 2H), 2.95 (m, 2H), 2.9 (m, 2H), 2.4 (t, 3H), 2.2 (s, 3H), 2 (m, 3H), 1.8 to 1.6 (m, 6H), 1.5 (m, 2H)

Example 52 ethyl 1-(6-(3,5-difluoro-2-((2-methyl-4-(1-(3,3,3-trifluoropropyl)piperidin-4-yl)benzyl)oxy)phenyl)pyridin-2-yl)piperidine-4-carboxylate

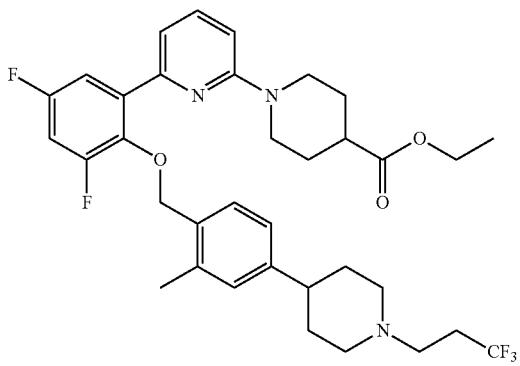 [SMILES: CCOC(=O)C1CCN(c2cccc(-c3cc(F)cc(F)c3OCc3ccc(C4CCN(CCC(F)(F)F)CC4)cc3C)n2)CC1]

To a solution of ethyl 1-(6-(3,5-difluoro-2-((2-methyl-4-(piperidin-4-yl)benzyl)oxy)phenyl)pyridin-2-yl)piperidine-4-carboxylate (200 mg, 0.364 mmol) in Acetone (10 mL), were added Cs$_2$CO$_3$ (296 mg, 0.910 mmol) and then dropwise 3-bromo-1,1,1-trifluoropropane (0.056 mL, 0.546 mmol). The reaction mixture was stirred at 80° C. for 12 hours, then cooled and filtered on a celite pad. The filtrate was concentrated under reduced pressure. The crude residue was partitioned between EtOAc (50 mL) and water (20 mL). The organic phase was separated and the aqueous phase was further extracted with EtOAc (2×20 ml). The combined organic phase was washed with brine solution (30 mL), dried over anhydrous Na$_2$SO$_4$ and concentrated under reduced pressure. The crude product was purified by column chromatography (initially eluted with EtOAc/Hexane 6/94 to remove non-polar impurities, then eluted with EtOAc/Hexane 10/90). The pure fractions were collected and concentrated under reduced pressure the title compound (60 mg, 25.02% yield) as a brown color liquid.

LCMS (a): Rt=2.78 min, M/z=646.3 (M+H)$^+$

Example 53

1-(6-(3,5-difluoro-2-((2-methyl-4-(1-(3,3,3-trifluoropropyl)piperidin-4-yl)benzyl)oxy)phenyl)pyridin-2-yl)piperidine-4-carboxylic acid

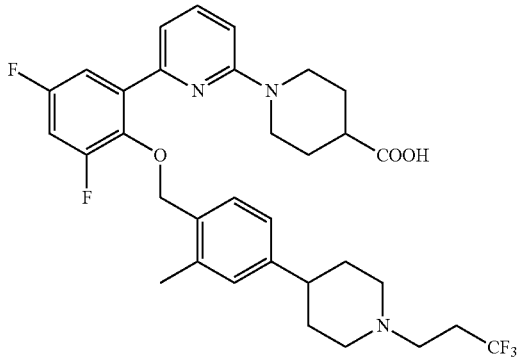 [SMILES: Cc1cc(C2CCN(CCC(F)(F)F)CC2)ccc1COc1c(F)cc(F)cc1-c1cccc(N2CCC(C(=O)O)CC2)n1]

To a solution of ethyl 1-(6-(3,5-difluoro-2-((2-methyl-4-(1-(3,3,3-trifluoropropyl)piperidin-4-yl)benzyl)oxy)phenyl)pyridin-2-yl)piperidine-4-carboxylate (210 mg, 0.325 mmol) in EtOH (5 mL) and Water (1.25 mL) cooled at 0° C., was added dropwise NaOH (0.650 mL, solution 1M, 0.650 mmol). The reaction mixture was stirred at 25° C. for 12 hours and then was concentrated under reduced pressure. The residue was diluted with water and the pH was adjusted to 5 with a 5% citric acid solution. The resulting precipitate was filtered, washed with water and dried to afford the title compound (90 mg, 41.4% yield) as off white solid.

LCMS (e): Rt=3.46 min, M/z=618.52 (M+H)$^+$

Example 54

1-(6-(3,5-difluoro-2-((2-methyl-4-(1-(3,3,3-trifluoropropyl)piperidin-4-yl)benzyl)oxy)phenyl)pyridin-2-yl)piperidine-4-carboxylic acid, Sodium salt

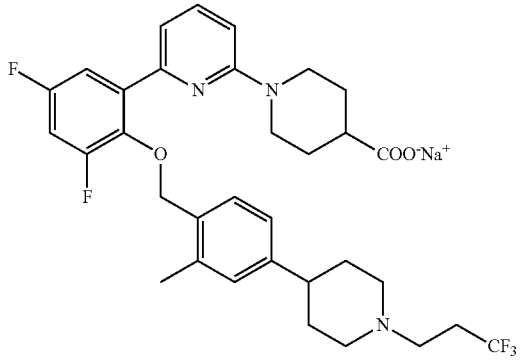

To a solution of 1-(6-(3,5-difluoro-2-((2-methyl-4-(1-(3,3,3-trifluoropropyl)piperidin-4-yl)benzyl)oxy)phenyl)pyridin-2-yl)piperidine-4-carboxylic acid (90 mg, 0.146 mmol) in Water (10 mL) was added sodium bicarbonate (12.24 mg, 0.146 mmol) in Water (2 mL). The reaction mixture was stirred at 25° C. for 20 minutes and then was transferred to a lyophilization flask and lyophilized for 12 hours to afford the title compound (90 mg, 88% yield) as an off white solid.

LCMS (a): Rt=2.05 min, M/z=618.31 (M+H)$^+$

1H NMR (DMSO d6 ppm): 7.5 (dd, 1H), 7.36 (m, 2H), 7.08 (m, 2H), 7.01 (m, 2H), 6.81 (d, 1H), 4.81 (s, 2H), 4.16 (m, 1H), 4.13 (m, 1H), 2.96 (m, 2H), 2.89 (m, 2H), 2.52 (m, 2H), 2.46 (m, 2H), 2.2 (s, 3H), 2.03 (m, 3H), 1.8 to 1.7 (m, 4H), 1.65 to 1.49 (m, 5H)

Example 55 ethyl 1-(6-(3,5-difluoro-2-((4-(1-(2-hydroxyacetyl)piperidin-4-yl)-2-methylbenzyl)oxy)phenyl)pyridin-2-yl)piperidine-4-carboxylate

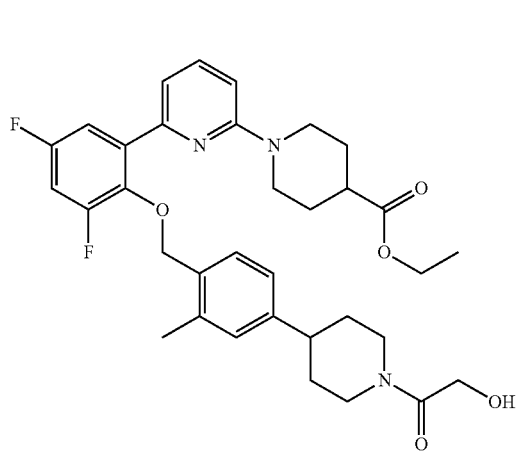

To a stirred solution 2-hydroxyacetic acid (66.4 mg, 0.873 mmol) in Acetonitrile (20 mL) under Nitrogen atmosphere were added ethyl 1-(6-(3,5-difluoro-2-((2-methyl-4-(piperidin-4-yl)benzyl)oxy)phenyl)pyridin-2-yl)piperidine-4-carboxylate (400 mg, 0.728 mmol) followed by HATU (415 mg, 1.092 mmol). The reaction mixture was cooled to 0° C. and then DIPEA (0.380 mL, 2.183 mmol) was added dropwise. The reaction mixture was stirred at 25° C. for 16 hours and then was concentrated under reduced pressure. The residue was dissolved in EtOAc (25 mL) and washed with water (3×15 mL) followed by saturated NaCl (aq) solution (15 mL). The organic phase was dried over anhydrous $Na_2SO_4$ and concentrated under reduced pressure. The crude product was purified by combiflash column chromatography (eluted with EtOAc/Hexane, 65/35 to 75/25). Collected fractions were concentrated under reduced pressure to afford the title compound (242 mg, 49.7% yield) as a light brown gum.

LC/MS (j): Rt=5.38 min, M/z=608 $(M+H)_+$

Example 56

1-(6-(3,5-difluoro-2-((4-(1-(2-hydroxyacetyl)piperidin-4-yl)-2-methylbenzyl)oxy)phenyl)pyridin-2-yl)piperidine-4-carboxylic acid

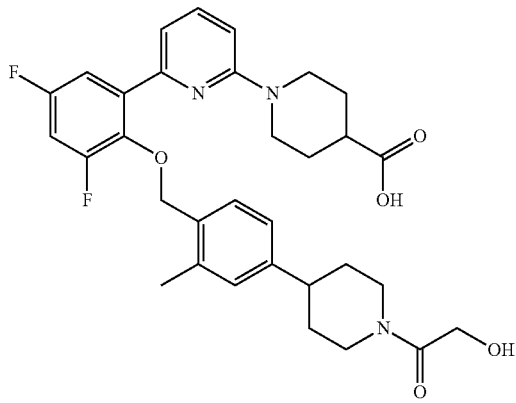 [SMILES: Cc1cc(C2CCN(C(=O)CO)CC2)ccc1COc1c(F)cc(F)cc1-c1cccc(N2CCC(C(=O)O)CC2)n1]

To a solution ethyl 1-(6-(3,5-difluoro-2-((4-(1-(2-hydroxyacetyl)piperidin-4-yl)-2-methylbenzyl)oxy)phenyl)pyridin-2-yl)piperidine-4-carboxylate (240 mg, 0.395 mmol) in EtOH (5 mL) stirred at 0° C., was added dropwise sodium hydroxide (1.185 mL, solution 1M, 1.185 mmol). The reaction mixture was stirred at 25° C. for 16 hours and then was concentrated under reduced pressure to remove EtOH. Cold water (10 mL) was added to the crude residue and the pH was adjusted to 5 with citric acid (10% aqueous solution) at 0° C. The resulting precipitate was filtered, washed with water (3×10 mL), then n-pentane (2×10 mL) and dried. The product was purified by combiflash column chromatography (eluted with $CH_2Cl_2$/MeOH, 95/5 to 94/6). Collected fractions were concentrated under reduced pressure to afford the title compound (80 mg, 33.8% yield) as a light brown gum.

LC/MS (a): Rt=2.31 min, M/z=580.42 $(M+H)^+$

Example 57

1-(6-(3,5-difluoro-2-((4-(1-(2-hydroxyacetyl)piperidin-4-yl)-2-methylbenzyl)oxy)phenyl)pyridin-2-yl) piperidine-4-carboxylic acid, Sodium salt

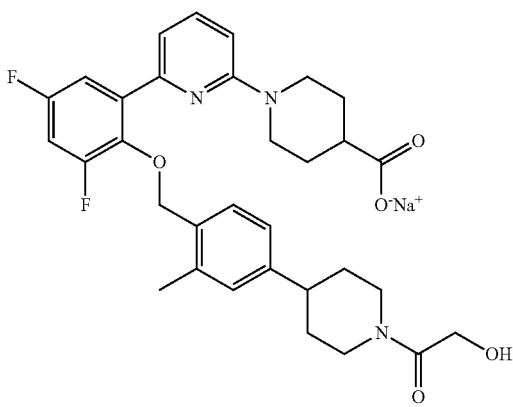

To a solution solution of 1-(6-(3,5-difluoro-2-((4-(1-(2-hydroxyacetyl)piperidin-4-yl)-2-methylbenzyl)oxy)phenyl)pyridin-2-yl)piperidine-4-carboxylic acid (80 mg, 0.138 mmol) in Water (2.5 mL) stirred at 0° C., was added dropwise sodium hydroxide (0.138 mL, solution 1M, 0.138 mmol). The reaction mixture was stirred at 25° C. for 20 minutes and then was transfered to a lyophilization flask and lyophilized for 16 hours to afford the title compound (80 mg, 93% yield) as a off white solid.

LCMS (a): Rt=2.3 min, M/z=580.45 $(M+H)^+$

1H NMR (DMSO d6 ppm): 7.49 (dd, 1H), 7.35 (m, 2H), 7.06 to 6.95 (m, 4H), 6.78 (d, 1H), 4.83 (s, 2H), 4.48 (m, 1H), 4.1 (m, 4H), 3.82 (m, 1H), 3.03 (m, 1H), 2.88 (m, 2H), 2.68 (m, 2H), 2.19 (s, 3H), 1.95 (m, 1H), 1.74 (m, 4H), 1.53 to 1.45 (m, 4H)

Example 58 ethyl 1-(6-(3, 5-difluoro-2-((4-(1-(2-methoxyacetyl) piperidin-4-yl)-2-methylbenzyl)oxy)phenyl)pyridin-2-yl)piperidine-4-carboxylate

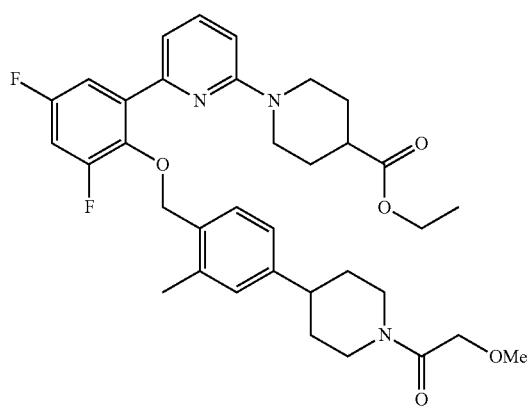 [SMILES: CCOC(=O)C1CCN(c2cccc(-c3cc(F)cc(F)c3OCc3ccc(C4CCN(C(=O)COC)CC4)cc3C)n2)CC1]

To a solution of ethyl 1-(6-(3,5-difluoro-2-((2-methyl-4-(piperidin-4-yl)benzyl)oxy)phenyl)pyridin-2-yl)piperidine-4-carboxylate (400 mg, 0.728 mmol) in Acetonitrile (10 mL) stirred at 0° C., were added 2-methoxyacetic acid (79 mg, 0.873 mmol) and HATU (415 mg, 1.092 mmol). The reaction mixture was stirred at 0° C. for 30 minutes. Then DIPEA (0.381 mL, 2.183 mmol) was added portion wise and the reaction mixture was stirred at 25° C. for 12 hours and then was diluted with water (10 ml). After extraction with EtOAc (3×30 ml). The combined organic phase was washed with water (2×20 ml) dried over anhydrous $Na_2SO_4$, and then concentrated under reduced pressure. The crude product was purified by column chromatography (100-200 mesh silica gel, eluted with $CH_2Cl_2$/MEOH, 99/1 to 98/2, to removed non-polar impurities, and then $CH_2Cl_2$/MEOH, 92/8) Collected fractions were concentrated under reduced pressure to afford the title compound (400 mg, 75% yield) as a gummy solid.

LC/MS (b): Rt=5.35 min, M/z=622.34 $(M+H)^+$

Example 59

1-(6-(3,5-difluoro-2-((4-(1-(2-methoxyacetyl)piperidin-4-yl)-2-methylbenzyl)oxy)phenyl)pyridin-2-yl)piperidine-4-carboxylic acid

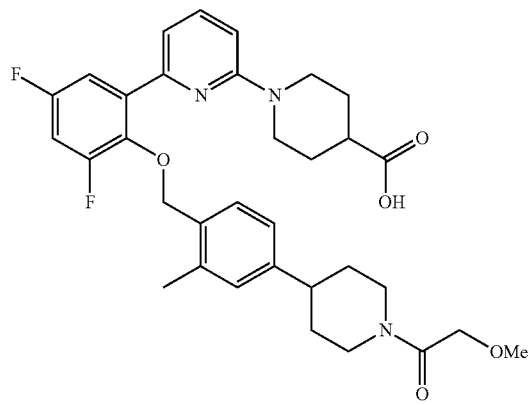 [SMILES: COCC(=O)N1CCC(c2ccc(COc3c(F)cc(F)cc3-c3cccc(N4CCC(C(=O)O)CC4)n3)c(C)c2)CC1]

To a stirred solution of ethyl 1-(6-(3,5-difluoro-2-((4-(1-(2-methoxyacetyl)piperidin-4-yl)-2-methylbenzyl)oxy)phenyl)pyridin-2-yl)piperidine-4-carboxylate (400 mg, 0.643 mmol) in EtOH (5 mL) was added NaOH (51.5 mg, 1.287 mmol) in Water (2 mL). The reaction mixture was stirred at 0° C. for 30 minutes, then at 25° C. for 12 hours and was concentrated under reduced pressure to remove EtOH. The crude residue was diluted with water (10 ml) and the pH was adjusted to 5 with a 5% citric acid solution. The resulting precipitate was filtered, washed with water (10 ml), then n-pentane (10 ml) and dried under vacuum. The product was purified by Prep-HPLC.
Prep-HPLC Conditions:
Column: XBridge C18 (250*30) 5 u
MP-A: 5 mM Ammonium Bicarbonate (Aq) MP-B: Acetonitrile
Method: Isocratic (A:B)=25:75
Flow: 30 ml/min
Solubility: ACN+MEOH+THF(excess)+H20
Fraction volume: 500 ml Collected fractions were concentrated under reduced pressure to remove ACN and then EtOAc (20 ml) was added. The organic phase was separated, dried over anhydrous $Na_2SO_4$, and then concentrated under reduced pressure to afford the title compound (95 mg, 24.62% yield) as off white solid.

LC/MS (e): Rt=2.99 min, M/z=594.46 $(M+H)^+$

Example 60

1-(6-(3,5-difluoro-2-((4-(1-(2-methoxyacetyl)piperidin-4-yl)-2-methylbenzyl)oxy)phenyl)pyridin-2-yl)piperidine-4-carboxylic acid, Sodium salt

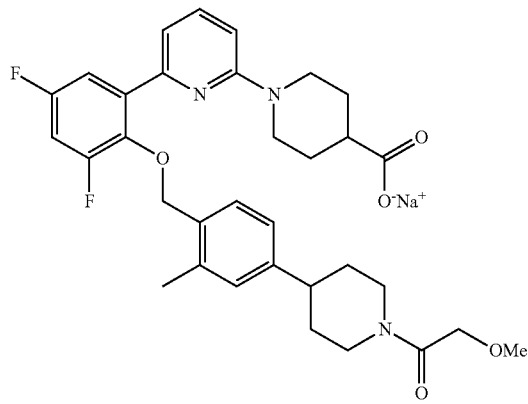

To a solution of 1-(6-(3,5-difluoro-2-((4-(1-(2-methoxyacetyl)piperidin-4-yl)-2-methylbenzyl)oxy)phenyl)pyridin-2-yl)piperidine-4-carboxylic acid (60 mg, 0.101 mmol) in Water (5 mL) was added sodium bicarbonate (8.49 mg, 0.101 mmol) in Water (2 mL). The reaction mixture was stirred at 25° C. for 20 minutes and then was transferred to a lyophilization flask and lyophilized for 12 hours to afford the title compound (59 mg, 94% yield) as an off white solid.

LC/MS (a): Rt=2.42 min, M/z=594.26 $(M+H)^+$

1H NMR ($CD_3OD$, ppm): 7.46 (dd, 1H), 7.29 (m, 1H), 7.05 (t, 2H), 7.02 to 6.94 (m, 3H), 6.76 (d, 1H), 4.84 (s, 2H), 4.62 (m, 1H), 4.34 (m, 2H), 4.19 (q, 2H), 3.96 (m, 1H), 3.42 (s, 3H), 3.15 (m, 1H), 2.88 (m, 2H), 2.75 (m, 2H), 2.34 (m, 1H), 2.24 (s, 3H), 1.93 (m, 2H), 1.86 (m, 2H), 1.76 to 1.55 (m, 4H)

Example 61 ethyl 1-(6-(2-((4-(1-(2-cyanoacetyl)piperidin-4-yl)-2-methylbenzyl)oxy)-3,5-difluorophenyl)pyridin-2-yl)piperidine-4-carboxylate

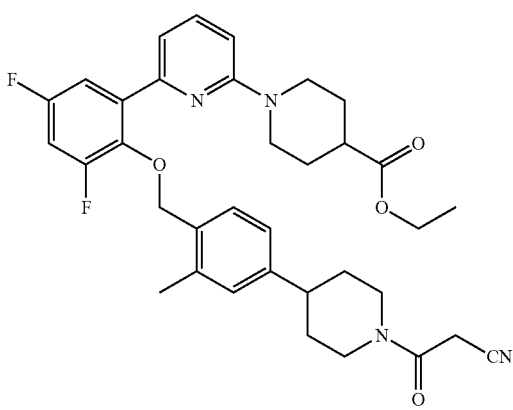

To a stirred solution of ethyl 1-(6-(3,5-difluoro-2-((2-methyl-4-(piperidin-4-yl)benzyl)oxy)phenyl)pyridin-2-yl)piperidine-4-carboxylate (500 mg, 0.910 mmol) in Acetonitrile (20 mL) stirred at 0° C., was added 2-cyanoacetic acid (93 mg, 1.092 mmol) and HATU (519 mg, 1.365 mmol). The reaction mixture was stirred at 0° C. for 30 minutes. Then added DIPEA (0.477 mL, 2.73 mmol) was added dropwise and the reaction mixture was stirred at 25° C. for 12 hours and then was diluted with water (20 ml). After extraction with EtOAc (3×30 ml), the combined organic phase was washed with water (2×20 mL), dried over anhydrous Na$_2$SO$_4$ and then concentrated under reduced pressure. The crude product was purified by column chromatography (100-200mesh silica gel eluted with CH$_2$Cl$_2$/MeOH 99/1 to 98/2 to removed non-polar impurities, then with CH$_2$Cl$_2$/MeOH 95/5). The collected fractions were concentrated under reduced pressure to afford the title compound (350 mg, 56.0% yield) as off white solid.

LCMS (e): Rt=4.26 min, M/z=617.39 (M+H)$^+$

Example 62

1-(6-(2-((4-(1-(2-cyanoacetyl)piperidin-4-yl)-2-methylbenzyl)oxy)-3,5-difluorophenyl)pyridin-2-yl)piperidine-4-carboxylic acid

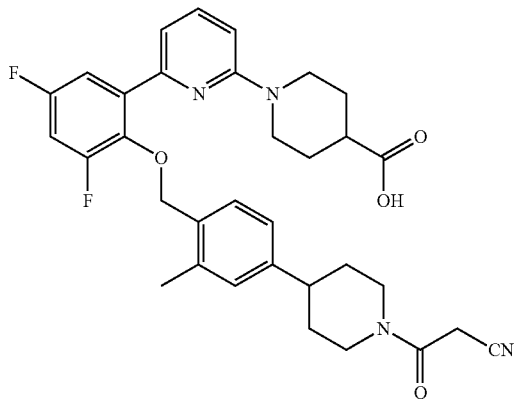

To a stirred solution of ethyl 1-(6-(2-((4-(1-(2-cyanoacetyl)piperidin-4-yl)-2-methylbenzyl)oxy)-3,5-difluorophenyl)pyridin-2-yl)piperidine-4-carboxylate (350 mg, 0.568 mmol) in THF (10 mL) was added potassium trimethylsilanolate (146 mg, 1.135 mmol). The reaction mixture was stirred at 40° C. for 3 hours and then was cooled to 0° C. The pH was adjusted to 5 with a 5% citric acid solution and then was diluted with water (10 ml). After extraction with EtOAc (3×20 ml), the combined organic phase was washed with water (2×20 mL), dried over anhydrous Na$_2$SO$_4$ and then concentrated under reduced pressure. The crude product was purified by Prep-HPLC.

Prep-HPLC Conditions:
Column: Xbridge C18 (30×250) mm 5 μ
MP-A: 5 Mm ammonium bicarbonate (Aq) MP-B: Acetonitrile
Method: T/% B=0/30,10/60,10.5/100,18/100,18.5/30
Flow: 30 ml/min
Solubility: THF+ACN+MEOH
Fraction volume: 500 ml Collected fractions were concentrated under reduced pressure to remove acetonitrile and then EtOAc (20 ml) was added. The organic phase was separated, dried over anhydrous Na$_2$SO$_4$, then concentrated under reduced pressure to afford the title compound (95 mg, 27.5% yield) as off white solid.

LCMS (g): Rt=4.8 min, M/z=589.2 (M+H)$^+$

Example 63

1-(6-(2-((4-(1-(2-cyanoacetyl)piperidin-4-yl)-2-methylbenzyl)oxy)-3,5-difluorophenyl)pyridin-2-yl)piperidine-4-carboxylic acid, Sodium salt

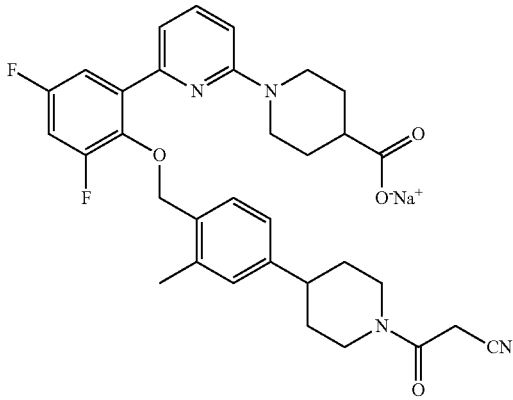

To a solution of 1-(6-(2-((4-(1-(2-cyanoacetyl)piperidin-4-yl)-2-methylbenzyl)oxy)-3,5-difluorophenyl)pyridin-2-yl)piperidine-4-carboxylic acid (95 mg, 0.161 mmol) in Water (5 mL) was added sodium bicarbonate (13.56 mg, 0.161 mmol) in Water (2 mL). The reaction mixture was stirred at 25° C. for 20 minutes and then was transferred to a lyophilization flask and lyophilized for 12 hours to afford the title compound (91 mg, 91% yield) as an off white solid.

LCMS (a): Rt=2.45 min, M/z=589.22 (M+H)$^+$

1H NMR (d6-DMSO, ppm): 7.49 (dd, 1H), 7.35 (m, 2H), 7.1 (d, 1H), 7.03 (m, 2H), 6.98 (m, 1H), 6.79 (d, 1H), 4.83 (s, 2H), 4.45 (m, 1H), 4.14 to 4 (m, 4H), 3.76 (m, 1H), 3.11 (m, 1H), 2.88 (m, 2H), 2.75 to 2.64 (m, 2H), 2.2 (s, 3H), 1.95 (m, 1H), 1.76 to 1.6 (m, 5H), 1.52 to 1.44 (m, 3H)

Example 64 ethyl 1-(6-(2-((4-(1-(2-cyclopropylacetyl)piperidin-4-yl)-2-methylbenzyl)oxy)-3,5-difluorophenyl)pyridin-2-yl)piperidine-4-carboxylate

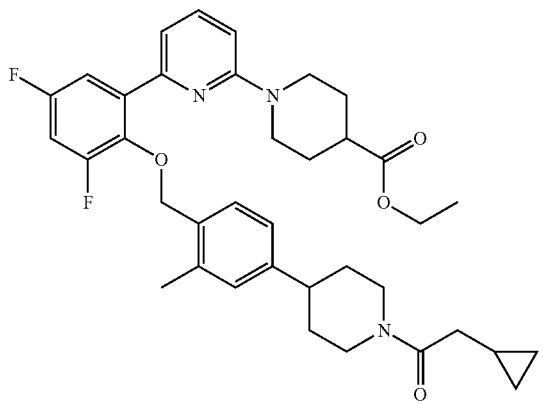 [SMILES: CCOC(=O)C1CCN(c2cccc(-c3cc(F)cc(F)c3OCc3ccc(C4CCN(C(=O)CC5CC5)CC4)cc3C)n2)CC1]

To a solution of ethyl 1-(6-(3,5-difluoro-2-((2-methyl-4-(piperidin-4-yl)benzyl)oxy)phenyl)pyridin-2-yl)piperidine-4-carboxylate (600 mg, 1.092 mmol) in DMF (10 mL) stirred at 0° C., were added 2-cyclopropylacetic acid (131 mg, 1.310 mmol) and HATU (623 mg, 1.637 mmol). The reaction mixture was stirred at 0° C. for 30 minutes and then was added dropwise DIPEA (0.572 mL, 3.27 mmol). The reaction mixture was stirred at 25° C. for 12 hours and then was partitioned between water (10 ml) and EtOAc (20 ml). The organic phase was separated and the aqueous phase was further extracted with EtOAc (2×30 ml). The combined organic phase was washed with water (2×20 ml), dried over anhydrous $Na_2SO_4$ and then concentrated under reduced pressure. The crude product was purified by column chromatography (100-200 mesh silica gel, initially eluted with EtOAc/Hexane, 10/90 to 20/80 to removed non-polar impurities, and then eluted with EtOAc/Hexane 80/20). Collected fractions were concentrated under reduced pressure to afford the title compound (400 mg, 53.3% yield) as off white solid.

LCMS (a): Rt=3.19 min, M/z=6 .26 (M+H)+

Example 65

1-(6-(2-((4-(1-(2-cyclopropylacetyl)piperidin-4-yl)-2-methylbenzyl)oxy)-3,5-difluorophenyl)pyridin-2-yl)piperidine-4-carboxylic acid

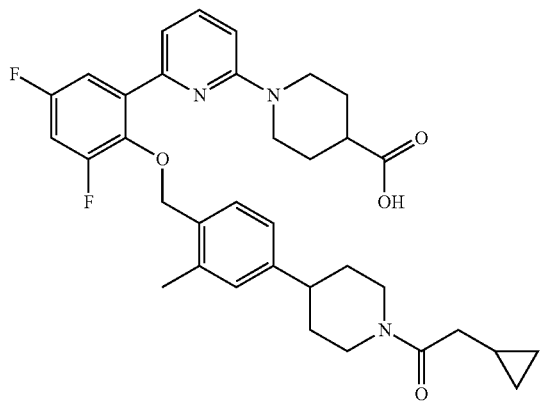 [SMILES: Cc1cc(C2CCN(C(=O)CC3CC3)CC2)ccc1COc1c(F)cc(F)cc1-c1cccc(N2CCC(C(=O)O)CC2)n1]

To a solution of ethyl 1-(6-(2-((4-(1-(2-cyclopropylacetyl)piperidin-4-yl)-2-methylbenzyl)oxy)-3,5-difluorophenyl)pyridin-2-yl)piperidine-4-carboxylate (400 mg, 0.633 mmol) in EtOH (10 mL) and water (4 mL) stirred at 0° C., was added NaOH (1.266 mL, solution 1M, 1.266 mmol). The reaction mixture was stirred at 0° C. for 30 minutes, then at 25° C. for 12 hours and then was concentrated under reduced pressure to remove Ethanol. The crude product was diluted with water (10 ml) and the PH was adjusted to 5 with a 5% citric acid solution. The resulting precipitate was filtered, washed with water (10 ml) and dried under vaccum to afford the title compound (280 mg, 71.7% yield) as off white solid.

LCMS (e): Rt=3.22 min, M/z=604.35 (M+H)+

Example 66

1-(6-(2-((4-(1-(2-cyclopropylacetyl)piperidin-4-yl)-2-methylbenzyl)oxy)-3,5-difluorophenyl)pyridin-2-yl)piperidine-4-carboxylic acid, Sodium salt

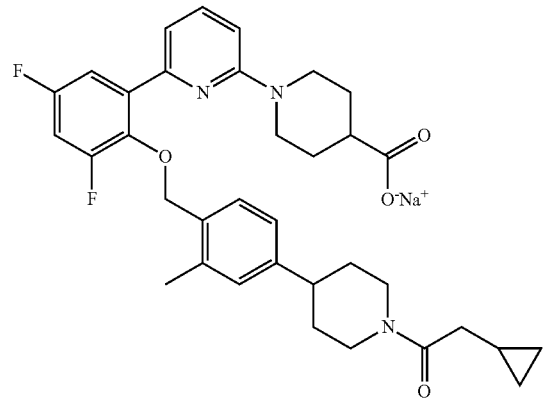

To a solution of 1-(6-(2-((4-(1-(2-cyclopropylacetyl)piperidin-4-yl)-2-methylbenzyl)oxy)-3,5-difluorophenyl)pyridin-2-yl)piperidine-4-carboxylic acid (280 mg, 0.464 mmol) in Water (10 mL) was added sodium bicarbonate (39.0 mg, 0.464 mmol) in Water (2 mL). The reaction mixture was stirred at 25° C. for 20 minutes, then was transfered to a lyophilization flask and lyophilized for 12 hours to afford the title compound (248 mg, 84% yield) as an off white solid.

LCMS (a): Rt=2.62 min, M/z=604.24 (M+H)+

1H NMR (d6-DMSO, ppm): 7.5 (t, 1H), 7.36 (m, 2H), 7.11 (d, 1H), 7.04 (m, 2H), 7 (d, 1H), 6.8 (d, 1H), 4.82 (s, 2H), 4.56 (m, 1H), 4.16 (m, 1H), 4.13 (m, 1H), 3.93 (m, 1H), 3.07 (m, 1H), 2.89 (m, 2H), 2.7 (m, 1H), 2.57 (m, 1H), 2.28 (d, 2H), 2.20 (s, 3H), 1.99 (m, 1H), 1.75 (m, 4H), 1.55 to 1.36 (m, 4H), 0.97 (m, 1H), 0.45 (m, 2H), 0.13 (m, 2H)

Example 67 ethyl 1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylate

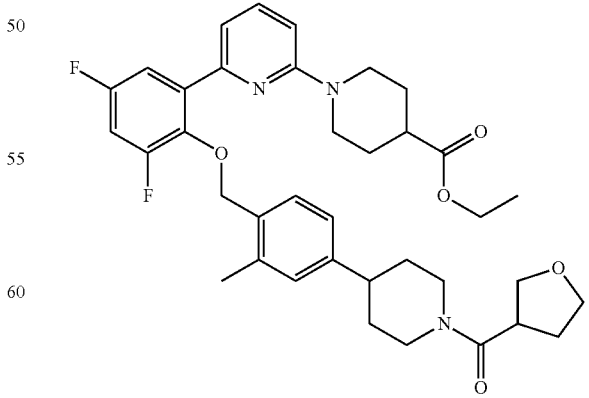

To a solutionn of ethyl 1-(6-(3,5-difluoro-2-((2-methyl-4-(piperidin-4-yl)benzyl)oxy)phenyl)pyridin-2-yl)piperidine-4-carboxylate (600 mg, 1.092 mmol) in DMF (10 mL) stirred at 0° C., were added tetrahydrofuran-3-carboxylic acid (152 mg, 1.310 mmol) and HATU (623 mg, 1.637 mmol). The reaction mixture was stirred at 0° C. for 30 minutes. Then DIPEA (0.572 mL, 3.27 mmol) was added dropwise and the reaction mixture was stirred at 25° C. for 12 hours and then partitioned between water (15 mL) and EtOAc (20 mL). The organic phase was separated and the aqueous phase was further extracted with EtOAc (2×30 ml). The combined organic phase was washed with water (2×20 ml), dried over anhydrous $Na_2SO_4$ and then concentrated under reduced pressure. The crude product was purified by column chromatography (100-200mesh silica gel, initially eluted with EtOAc/Hexane 10/9 to 20/80 to removed non-polar impurities, and then EtOAc/Hexane 85/15). Collected fractions were concentrated under reduced pressure to afford the title compound (300 mg, 41.4%yield) as off white solid.

LCMS (e): Rt=4.77 min, M/z=648.69 $(M+H)^+$

Example 68

1-(6-(3,5-difluoro-2-((2-methyl-4-(1-(tetrahydro-furan-3-carbonyl)piperidin-4-yl)benzyl)oxy)phenyl)pyridin-2-yl)piperidine-4-carboxylic acid

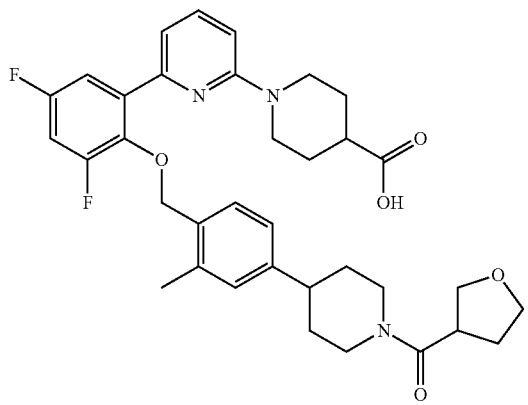 [SMILES: Cc1cc(C2CCN(C(=O)C3CCOC3)CC2)ccc1COc1c(F)cc(F)cc1-c1cccc(N2CCC(C(=O)O)CC2)n1]

To solution of ethyl 1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylate (300 mg, 0.463 mmol) in EtOH (10 mL) and water (4 mL) stirred at 0° C., was added NaOH (0.926 mL, solution 1M, 0.926 mmol). The reaction mixture was stirred at 0° C. for 30 minutes, then at 25° C. for 12 hours and then was concentrated under reduced pressure to remove Ethanol. The crude product was diluted with water (10 ml) and the PH was adjusted to 5 with a 5% citric acid solution. The resulting precipitate was filtered, washed with water (10 ml) and then dried to afford the title compound (250 mg, 84% yield) as off white solid.

LCMS (a): Rt=2.54 min, M/z=620.20 $(M+H)^+$

Example 69

1-(6-(3,5-difluoro-2-((2-methyl-4-(1-(tetrahydro-furan-3-carbonyl)piperidin-4-yl)benzyl)oxy)phenyl)pyridin-2-yl)piperidine-4-carboxylic acid, Sodium salt

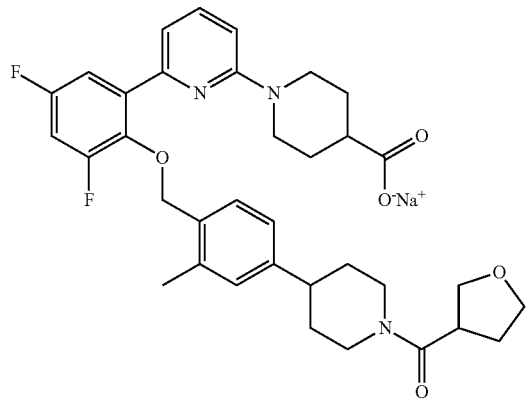

To a solution of 1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid (250 mg, 0.403 mmol) in Water (10 mL) was added sodium bicarbonate (33.9 mg, 0.403 mmol) in Water (2 mL). The reaction mixture was stirred at 25° C. for 20 minutes and then was transferred to a lyophilization flask and lyophilized for 12 hours to afford the title compound (190 mg, 71.6% yield) as an off white solid.

LCMS (a): Rt=2.41 min, M/z=620.22 $(M+H)^+$

1H NMR (DMSO d6 ppm): 7.5 (t, 1H), 7.36 (m, 2H), 7.11 (d, 1H), 7.04 (m, 3H), 6.8 (d, 1H), 4.82 (s, 2H), 4.53 (m, 1H), 4.14 (m, 2H), 4.06 (m, 1H), 3.88 (m, 1H), 3.7 (m, 3H), 3.37 (m, 1H), 3.09 (m, 1H), 2.89 (m, 2H), 2.71 (m, 1H), 2.61 (m, 1H), 2.21 (s, 3H), 2.02 (m, 3H), 1.77 (m, 4H), 1.51 (m, 4H)

Example 70

(S)-1-(6-(3,5-difluoro-2-((2-methyl-4-(1-(tetrahydro-furan-3-carbonyl)piperidin-4-yl)benzyl)oxy)phenyl)pyridin-2-yl)piperidine-4-carboxylic acid

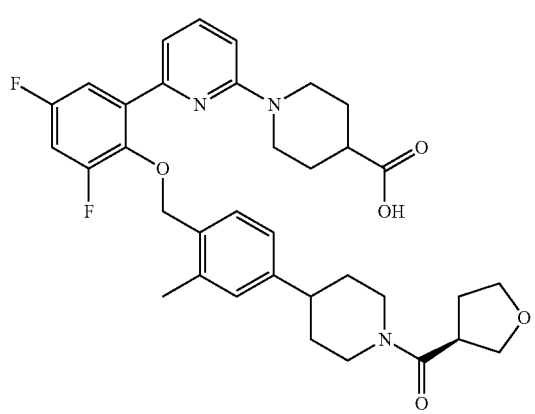 [SMILES: Cc1cc(C2CCN(C(=O)[C@H]3CCOC3)CC2)ccc1COc1c(F)cc(F)cc1-c1cccc(N2CCC(C(=O)O)CC2)n1]

1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid (Example 69) was purified by SFC.

Preparative SFC Conditions:
  Column/dimensions: Lux Amylose-2 (250×30)mm,5 μ
  % CO2: 50.0%
  % Co solvent: 50.0% (100% IPA)
  Total Flow: 100.0 g/min
  Back Pressure: 100.0 bar
  UV: 210 nm
  Stack time: 14.0 min
  Load/inj: 42.0 mg
  Solubility: MEOH+ACN The first eluted enantiomer was identified as the (S) enantiomer and obtained as off-white solid (by comparison with the (R) enantiomer prepared as described for Example 69, starting from (R)-tetrahydrofuran-3-carboxylic acid).

LC/MS (i): Rt=3.86 min, M/z=620.23 (M+H)$^+$
Chiral HPLC (a): purity=99.16%, Rt=2.95 min

Example 71

(R)-1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid

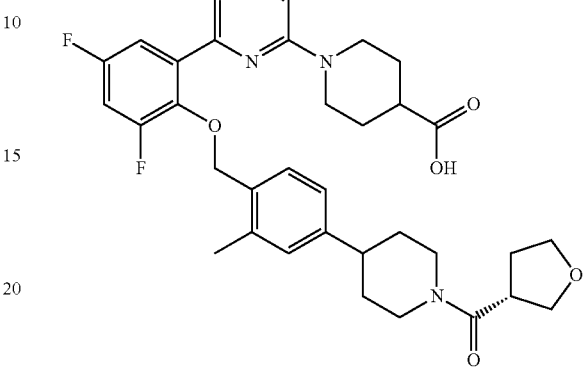

The second eluted enantiomer was identified as the (R) enantiomer and obtained as an off-white solid.
LC/MS (i): Rt=3.91 min, M/z=620.35 (M+H)$^+$
Chiral HPLC (a): purity=99.56%, Rt=4.99 min

Examples 72 and 73

The following examples were prepared using a similar procedure to the one described for Example 69.

| Ex. | Name | Chiral HPLC | LC/MS | $^1$H NMR (ppm) |
|---|---|---|---|---|
| 72 | (S)-1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid, Sodium salt | (a) purity: 99.59%, Rt = 3.77 min; ee: 99.18% | (i) Rt = 3.89 min, M/z = 620.29 (M + H)$^+$ | $^1$H NMR (d6-DMSO, ppm): 7.5 (dd, 1H), 7.36 (m, 2H), 7.11 (d, 1H), 7.05 (m, 2H), 7.01 (d, 1H), 6.8 (d, 1H), 4.82 (s, 2H), 4.52 (m, 1H), 4.16 (m, 1H), 4.13 (m, 1H), 4.06 (m, 1H), 3.88 (m, 1H), 3.77-3.65 (m, 3H), 3.37 (m, 1H), 3.09 (m, 1H), 2.89 (m, 2H), 2.72 (m, 1H), 2.61 (m, 1H), 2.2 (s, 3H), 2.07-1.96 (m, 3H), 1.78 (m, 4H), 1.54-1.4 (m, 4H) |

| Ex. | Name | Chiral HPLC | LC/MS | ¹H NMR (ppm) |
|---|---|---|---|---|
| 73 | (R)-1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid, Sodium salt N36162-70-1 | (b) Purity: 99.77%, Rt = 6.84 min; ee: 99.545% | (i) Rt = 3.96 min, M/z = 620.35 (M + H)⁺ | ¹H NMR (d6-DMSO, ppm): 7.5 (t, 1H), 7.36 (m, 2H), 7 (d, 1H), 7.04 (m, 3H), 6.8 (d, 1H), 4.82 (s, 2H), 4.54 (m, 1H), 4.15 (m, 1H), 4.12 (m, 1H), 4.06 (m, 1H), 3.88 (m, 1H), 3.7 (m, 3H), 3.37 (m, 1H), 3.1 (m, 1H), 2.89 (m, 2H), 2.72 (m, 1H), 2.61 (m, 1H), 2.21 (s, 3H), 2.05-1.95 (m, 3H), 1.76 (m, 4H), 1.55-1.45 (m, 4H) |

Example 74 ethyl 1-(6-(3,5-difluoro-2-((2-methyl-4-(1-(2-(oxetan-3-yl)acetyl)piperidin-4-yl)benzyl)oxy)phenyl)pyridin-2-yl)piperidine-4-carboxylate

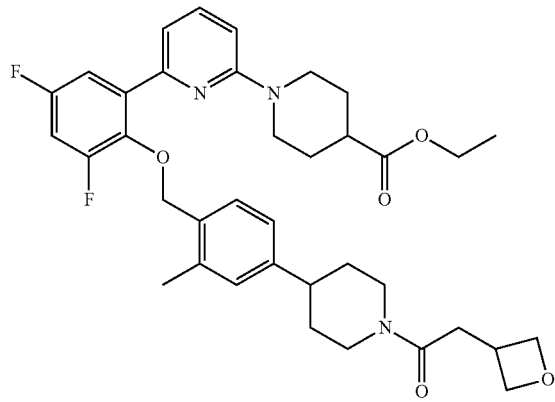 [SMILES: CCOC(=O)C1CCN(c2cccc(-c3cc(F)cc(F)c3OCc3ccc(C4CCN(C(=O)CC5COC5)CC4)cc3C)n2)CC1]

To a solution of ethyl 1-(6-(3,5-difluoro-2-((2-methyl-4-(piperidin-4-yl)benzyl)oxy)phenyl)pyridin-2-yl)piperidine-4-carboxylate (450 mg, 0.819 mmol) in DMF (10 mL) stirred at 0° C., were added lithium 2-(oxetan-3-yl)acetate (150 mg, 1.228 mmol) and HATU (467 mg, 1.228 mmol). The reaction mixture was stirred at 0° C. for 30 minutes. Then DIPEA (0.429 mL, 2.456 mmol) was added dropwise and the reaction mixture stirred at 25° C. for 12 hours and then partitioned between water (10 ml) and EtOAc (20 ml). The organic phase was separated and the aqueous phase was further extracted with EtOAc (2×30 ml). The combined organic phase was washed with water (2×20 ml), dried over anhydrous Na₂SO₄ and then concentrated under reduced pressure. The crude product was purified by column chromatography (100-200 mesh silica gel, initially eluted with CH₂Cl₂/MeOH 99/1 to 98/2, to remove non-polar impurities, then eluted with CH₂Cl₂/MeOH 95/5). The pure fractions were collected and concentrated under reduced pressure to afford the title compound (230 mg, 26.5% yield) as a gummy solid.

LCMS (f): Rt=4.409 min, M/z=648.0 (M+H)⁺

Example 75

1-(6-(3,5-difluoro-2-((2-methyl-4-(1-(2-(oxetan-3-yl)acetyl)piperidin-4-yl)benzyl)oxy)phenyl)pyridin-2-yl)piperidine-4-carboxylic acid

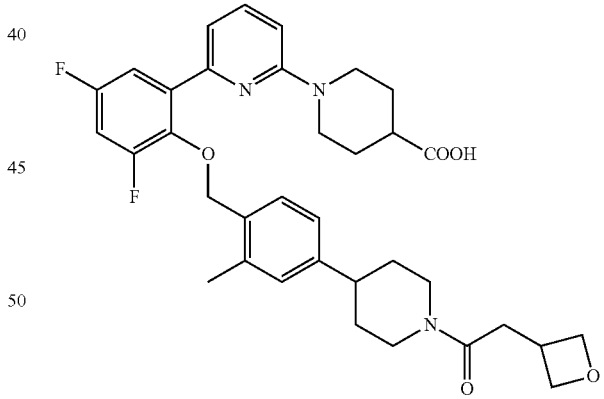

To a solution of ethyl 1-(6-(3,5-difluoro-2-((2-methyl-4-(1-(2-(oxetan-3-yl)acetyl)piperidin-4-yl)benzyl)oxy)phenyl)pyridin-2-yl)piperidine-4-carboxylate (230 mg, 0.355 mmol) in EtOH (10 mL) and water (2 mL) stirred at 0° C., was added NaOH (0.710 mL, solution 1M, 0.710 mmol). The reaction mixture was stirred at 0° C. for 30 minutes, then at 25° C. for 12 hours and then was concentrated under reduced pressure to remove EtOH. The crude product was diluted with water (10 ml) and the pH was adjusted to 5 with a 5% citric acid solution. The resulting precipitate was filtered, washed with water (10 ml) and dried under vacuum. The crude product was purified by Prep-HPLC.

Prep-HPLC Method Conditions:

Column: XBridge C 18(75×4.6 mm, 3.5 µ)

Mobile Phase: A: 5 mM Ammonium Bicarbonate B: ACN

Gradient: Time/% B: 0/5,0.8/5,5/50,9/98,12/98,12.1/5, 15/5

Column Temp:Ambient,

Flow Rate: 0.8 ml/min

Diluent: ACN

Fraction volume: 350 mL

Pure fractions were collected and lyophilized to afford the title compound (70 mg, 30.3% yield) as an off white solid.

LCMS (e): Rt=3.03 min, M/z=620.48 (M+H)$^+$

Example 76

1-(6-(3,5-difluoro-2-((2-methyl-4-(1-(2-(oxetan-3-yl)acetyl)piperidin-4-yl)benzyl)oxy)phenyl)pyridin-2-yl)piperidine-4-carboxylic acid, Sodium salt

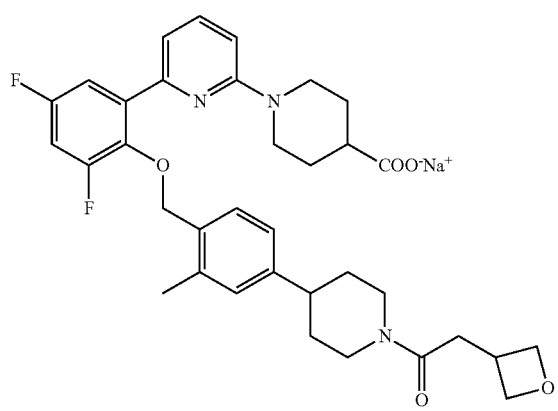

To a solution of 1-(6-(3,5-difluoro-2-((2-methyl-4-(1-(2-(oxetan-3-yl)acetyl)piperidin-4-yl)benzyl)oxy)phenyl)pyridin-2-yl)piperidine-4-carboxylic acid (70 mg, 0.113 mmol) in Water (10 mL) was added sodium bicarbonate (9.49 mg, 0.113 mmol) in Water (2 mL). The reaction mixture was stirred at 25° C. for 20 minutes and then was transferred to a lyophilization flask and lyophilized for 12 hours to afford the title compound (55 mg, 70.5% yield) as an off white solid.

LCMS (a): Rt=2.43 min, M/z=620.22 (M+H)$^+$

1H NMR (d6-DMSO, ppm): 7.5 (dd, 1H), 7.36 (m, 2H), 7.11 (d, 1H), 7.03 (m, 3H), 6.8 (d, 1H), 4.82 (s, 2H), 4.66 (dd, 2H), 4.49 (m, 1H), 4.27 (m, 2H), 4.16 (m, 1H), 4.12 (m, 1H), 3.96 (m, 1H), 3.23 (m, 1H), 3.07 (m, 1H), 2.89 (m, 2H), 2.77 (m, 2H), 2.70 (m, 1H), 2.56 (m, 1H), 2.2 (s, 3H), 1.98 (m, 1H), 1.75 (m, 4H), 1.57 to 1.37 (m, 4H)

Example 77 ethyl 1-(6-(3,5-difluoro-2-((2-methyl-4-(1-(2-(tetrahydrofuran-3-yl)acetyl)piperidin-4-yl)benzyl)oxy)phenyl)pyridin-2-yl)piperidine-4-carboxylate

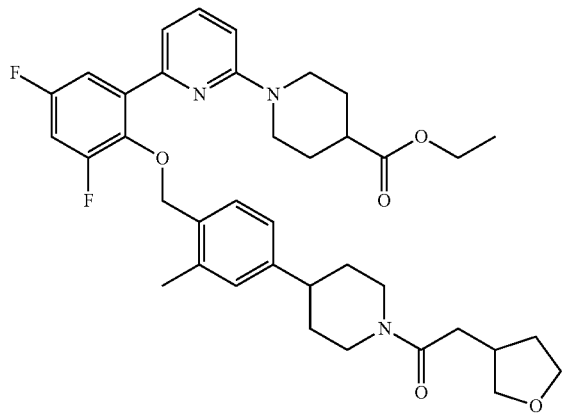 [SMILES: CCOC(=O)C1CCN(c2cccc(-c3cc(F)cc(F)c3OCc3ccc(C4CCN(C(=O)CC5CCOC5)CC4)cc3C)n2)CC1]

To a stirred solution of ethyl 1-(6-(3,5-difluoro-2-((2-methyl-4-(piperidin-4-yl)benzyl)oxy)phenyl)pyridin-2-yl)piperidine-4-carboxylate (500 mg, 0.910 mmol) in DMF (7 mL) stirred at 0° C., were added 2-(tetrahydrofuran-3-yl)acetic acid (142 mg, 1.092 mmol) and BOP-CI (347 mg, 1.365 mmol). The reaction mixture was stirred at 0° C. for 30 minutes and then DIPEA (0.477 mL, 2.73 mmol) was added dropwise. The reaction mixture was stirred at 25° C. for 12 hours and then was partitioned between water (10 ml) and EtOAc (20 ml). The organic phase was separated and the aqueous phase was further extracted with EtOAc (2×30 ml). The combined organic phase was washed with water (2×20 ml), dried over anhydrous Na$_2$SO$_4$ and then concentrated under reduced pressure. The crude product was purified by column chromatography (using 100-200 mesh silica gel, initially eluted with EtOAc/Hexane 10/90 to 20/80 to removed non-polar impurities, then with EtOAc/Hexane 8/2). The pure fractions were collected and concentrated under reduced pressure to afford the title compound (400 mg, 49.8% yield) as a gummy solid.

LCMS (a): Rt=3.01 min, M/z=662.34 (M+H)$^+$

Example 78

1-(6-(3,5-difluoro-2-((2-methyl-4-(1-(2-(tetrahydrofuran-3-yl)acetyl)piperidin-4-yl)benzyl)oxy)phenyl)pyridin-2-yl)piperidine-4-carboxylic acid

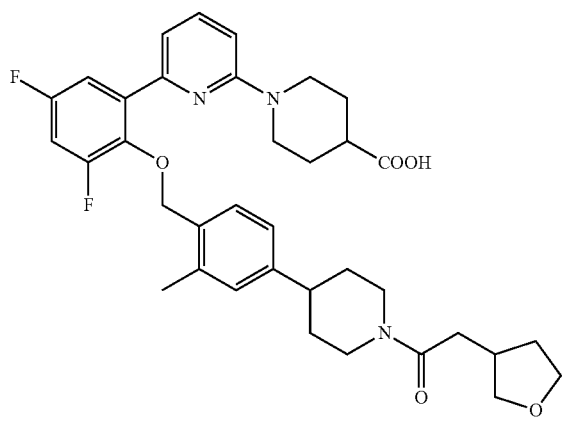 [SMILES: Cc1cc(C2CCN(C(=O)CC3CCOC3)CC2)ccc1COc1c(F)cc(F)cc1-c1cccc(N2CCC(C(=O)O)CC2)n1]

To a solution of ethyl 1-(6-(3,5-difluoro-2-((2-methyl-4-(1-(2-(tetrahydrofuran-3-yl)acetyl)piperidin-4-yl)benzyl)oxy)phenyl)pyridin-2-yl)piperidine-4-carboxylate (400 mg, 0.604 mmol) in THF (15 mL) was added potassium trimethylsilanolate (155 mg, 1.209 mmol). The reaction mixture was stirred at 40° C. for 3 hours and then was cooled to 0° C. The pH was adjusted to 5 with a 5% citric acid solution and the reaction mixture was then partitioned between water (10 ml) and EtOAc (25 ml). The organic phase was separated and the aqueous phase was further extracted with EtOAc (2×30 ml). The combined organic phase was washed with water (2×10 ml), dried over anhydrous $Na_2SO_4$ and then concentrated under reduced pressure. The crude product was purified by Prep-HPLC.
Prep-HPLC Method Conditions:
  Column: XBridge C 18(75×4.6 mm, 3.5 µ)
  Mobile Phase: A: 5 mM Ammonium Bicarbonate B: ACN
  Gradient: Time/% B: 0/5,0.8/5,5/50,9/98,12/98,12.1/5, 15/5
  Column Temp: Ambient, Flow Rate: 0.8 ml/min
  Diluent: ACN
  Fraction volume: 250 ml
  Collected fractions were lyophilized to afford the title compound (90 mg, 23.07% yield) as off white solid.
  LCMS (a): Rt=2.55 min, M/z=634.23 (M+H)$^+$ Example 79

1-(6-(3, 5-difluoro-2-((2-methyl-4-(1-(2-(tetrahydrofuran-3-yl)acetyl)piperidi n-4-yl)benzyl)oxy)phenyl) pyridin-2-yl)piperidine-4-carboxylic acid, Sodium salt

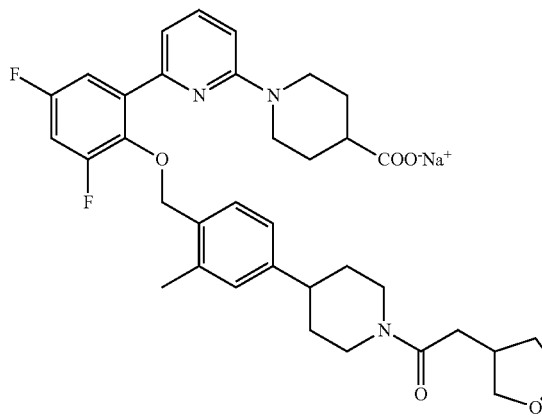

To a solution of 1-(6-(3,5-difluoro-2-((2-methyl-4-(1-(2-(tetrahydrofuran-3-yl)acetyl)piperidin-4-yl)benzyl)oxy)phenyl)pyridin-2-yl)piperidine-4-carboxylic acid (90 mg, 0.142 mmol) in Water (10 mL) was added sodium bicarbonate (11.93 mg, 0.142 mmol) in Water (2 mL). The reaction mixture was stirred at 25° C. for 20 minutes and then was transfered to a lyophilization flask and lyophilized for 12 hours to afford the title compound (92 mg, 98% yield) as an off white solid.
  LCMS (a): Rt=2.49 min, M/z=634.26 (M+H)$^+$
  1H NMR (DMSO d6 ppm): 7.5 (dd, 1H), 7.36 (m, 2H), 7.11 (d, 1H), 7.04 (m, 2H), 7 (d, 1H), 6.8 (d, 1H), 4.82 (s, 2H), 4.53 (m, 1H), 4.16 (m, 1H), 4.13 (m, 1H), 3.96 (m, 1H), 3.83 (m, 1H), 3.71 (m, 1H), 3.62 (m, 1H), 3.24 (m, 1H), 3.07 (m, 1H), 2.89 (m, 2H), 2.7 (m, 1H), 2.57 (m, 2H), 2.46 (m, 2H), 2.2 (s, 3H), 2 (m, 2H), 1.75 (m, 4H), 1.55 to 1.38 (m, 5H)

Intermediate 17: ethyl 1-(6-(2-((4-(1-(3-ethoxy-3-oxopropanoyl)piperidin-4-yl)-2-methylbenzyl)oxy)-3,5-difluorophenyl)pyridin-2-yl)piperidine-4-carboxylate

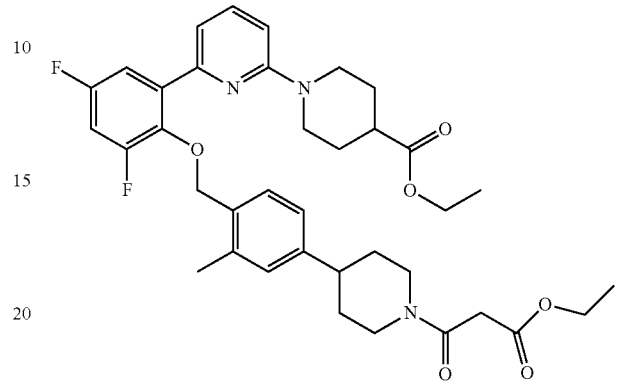

To a solution of ethyl 1-(6-(3,5-difluoro-2-((2-methyl-4-(piperidin-4-yl)benzyl)oxy)phenyl)pyridin-2-yl)piperidine-4-carboxylate (600 mg, 1.092 mmol) in DMF (5 mL) stirred at 0° C., were added 3-ethoxy-3-oxopropanoic acid, Lithium salt (182 mg, 1.310 mmol) and HATU (623 mg, 1.637 mmol). The reaction mixture was stirred at 0° C. for 30 minutes and then DIPEA (0.572 mL, 3.27 mmol) was added dropwise. The reaction mixture was stirred at 25° C. for 12 hours and then was partitioned between water (15 ml) and EtOAc (20 ml). The organic phase was separated and the aqueous phase was further extracted with EtOAc (2×30 ml). The combined organic phase was washed with water (2×20 ml), dried over anhydrous $Na_2SO_4$ and then concentrated under reduced pressure. The crude product was purified by column chromatography (using 100-200 mesh silica gel, initially eluted with EtOAc/Hexane 10/90 to 20/80 to removed non-polar impurities, and then with EtOAc/Hexane 85/15). Collected fractions were concentrated under reduced pressure to afford the title compound (300 mg, 37.3% yield) as off white solid.
  LCMS (a): Rt=3.08 min, M/z=664.54 (M+H)$^+$ Example 80

1-(6-(2-((4-(1-(2-carboxyacetyl)piperidin-4-yl)-2-methylbenzyl)oxy)-3,5-difluorophenyl)pyridin-2-yl)piperidine-4-carboxylic acid

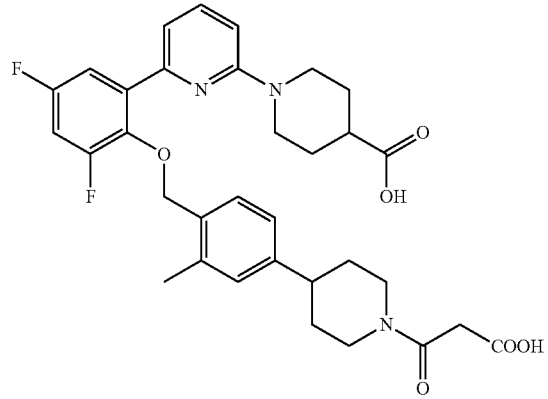 [SMILES: Cc1cc(C2CCN(C(=O)CC(=O)O)CC2)ccc1COc1c(F)cc(F)cc1-c1cccc(N2CCC(C(=O)O)CC2)n1]

To a stirred solution of ethyl 1-(6-(2-((4-(1-(3-ethoxy-3-oxopropanoyl)piperidin-4-yl)-2-methylbenzyl)oxy)-3,5-difluorophenyl)pyridin-2-yl)piperidine-4-carboxylate (250 mg, 0.377 mmol) in THF (15 mL) was added potassium trimethylsilanolate (193 mg, 1.507 mmol). The reaction mixture was stirred at 40° C. for 3 hours and then was cooled to 0° C. The pH was adjusted to 5 with a 5% citric acid solution. The mixture was partitioned between water (10 ml) and EtOAc (20 ml) and the organic phase was separated. The aqueous phase was further extracted with EtOAc (2×30 ml). The combined organic phase was washed with water (2×20 ml), dried over anhydrous Na$_2$SO$_4$ and then concentrated under reduced pressure to afford the title compound (180 mg, 73.1% yield) as off white solid.

LCMS (a): Rt=2.40 min, M/z=608.14 (M+H)$^+$

Example 81

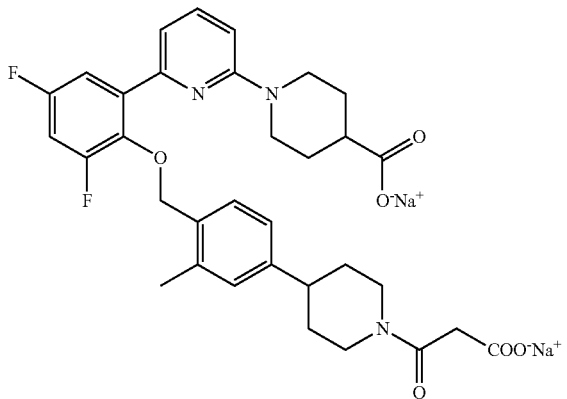

1-(6-(2-((4-(1-(2-carboxyacetyl)piperidin-4-yl)-2-methylbenzyl)oxy)-3,5-difluorophenyl)pyridin-2-yl)piperidine-4-carboxylic acid, di-Sodium salt To a solution of 1-(6-(2-((4-(1-(2-carboxyacetyl)piperidin-4-yl)-2-methylbenzyl)oxy)-3,5-difluorophenyl)pyridin-2-yl)piperidine-4-carboxylic acid (180 mg,0.296 mmol) in Water (10 mL) was added sodium bicarbonate (49.8 mg, 0.592 mmol) in Water (2 mL). The reaction mixture was stirred at 25° C. for 20 minutes and then was transferred to a lyophilization flask and lyophilized for 12 hours to afford the title compound (180 mg, 88% yield) as an off white solid.

LCMS (a): Rt=2.25 min, M/z=608.20 (M+H)$^+$

1H NMR (DMSO d6 ppm): 7.5 (dd, 1H), 7.35 (m, 2H), 7.02 (m, 4H), 6.79 (d, 1H), 4.82 (s, 2H), 4.5 (m, 1H), 4.14 (m, 1H), 4.11 (m, 1H), 4.04 (m, 1H), 2.97 (m, 3H), 2.87 (m, 2H), 2.66 (m, 2H), 2.19 (s, 3H), 1.98 (m, 1H), 1.77 to 1.66 (m, 5H), 1.56 to 1.45 (m, 3H)

Example 82 ethyl 1-(6-(2-((4-(1-(2-(1H-1,2,4-triazol-1-yl)acetyl) piperidin-4-yl)-2-methylbenzyl)oxy)-3,5-difluorophenyl)pyridin-2-yl)piperidine-4-carboxylate

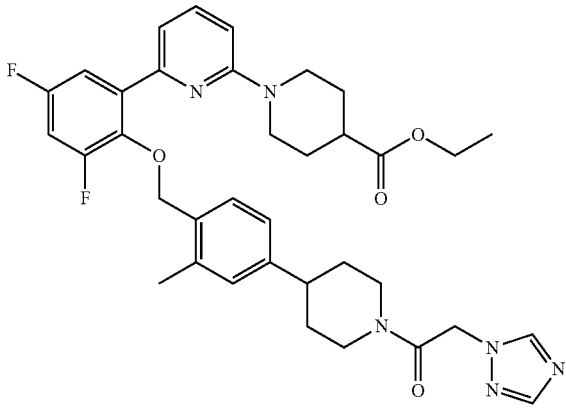 [SMILES: CCOC(=O)C1CCN(c2cccc(-c3cc(F)cc(F)c3OCc3ccc(C4CCN(C(=O)Cn5cncn5)CC4)cc3C)n2)CC1]

To a solution of ethyl 1-(6-(3,5-difluoro-2-((2-methyl-4-(piperidin-4-yl)benzyl)oxy)phenyl)pyridin-2-yl)piperidine-4-carboxylate (600 mg, 1.092 mmol) in DMF (5 mL) stirred at 0° C., were added 2-(1H-1,2,4-triazol-1-yl)acetic acid, Hydrochloride (214 mg, 1.310 mmol) and HATU (623 mg, 1.637 mmol). The reaction mixture was stirred at 0° C. for 30 minutes and then DIPEA (0.953 mL, 5.46 mmol) was added dropwise. The reaction mixture was stirred at 25° C. for 12 hours and then was diluted with EtOAc (50 mL) and washed with cold water (5×20 mL). The organic phase was washed with saturated brine solution (25 mL), dried over anhydrous Na$_2$SO$_4$, filtered and concentrated under reduced pressure. The crude product was purified by column chromatography (100-200 mesh silica, eluted with CH$_2$Cl$_2$/MeOH, 98/2 to 97/3 to remove non-polar impurities then with CH$_2$Cl$_2$/MeOH, 97/3 to 96/4). Collected fractions were concentrated under reduced pressure to afford the title compound (370 mg, 47.0% yield) as an off white solid.

LCMS (h): Rt=3.22 min, M/z=659.1 (M+H)$^+$

Example 83

1-(6-(2-((4-(1-(2-(1H-1,2,4-triazol-1-yl)acetyl)piperidin-4-yl)-2-methylbenzyl)oxy)-3,5-difluorophenyl)pyridin-2-yl)piperidine-4-carboxylic acid

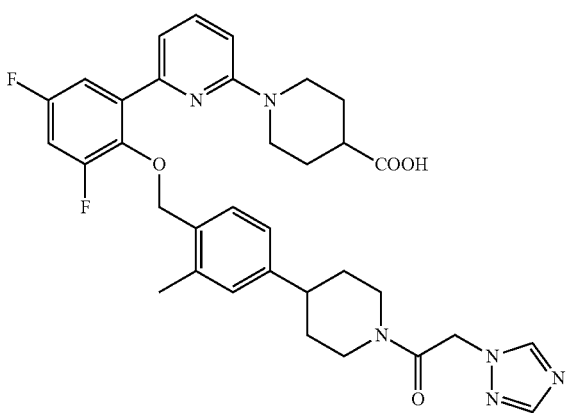 [SMILES: Cc1cc(C2CCN(C(=O)Cn3cncn3)CC2)ccc1COc1c(F)cc(F)cc1-c1cccc(N2CCC(C(=O)O)CC2)n1]

To a solution of ethyl 1-(6-(2-((4-(1-(2-(1H-1,2,4-triazol-1-yl)acetyl)piperidin-4-yl)-2-methylbenzyl)oxy)-3,5-difluorophenyl)pyridin-2-yl)piperidine-4-carboxylate (300 mg, 0.455 mmol) in EtOH (15 mL) stirred at 0° C., was added dropwise NaOH (1.366 mL, solution 1M, 1.366 mmol). The reaction mixture was stirred at 25° C. for 12 hours and then was concentrated under reduced pressure to remove the volatiles. The crude product was dissolved in water (10 mL) and washed with diethyl ether (3×15 mL). Then the aqueous phase was acidified with a 5% citric acid solution up to pH 5 at 0° C. and then extracted with EtOAc (3×15 mL). Combined organic phase was dried over anhydrous Na$_2$SO$_4$, filtered and concentrated under reduced pressure. The crude product was purified by column chromatography (230-400 mesh silica, eluted with CH$_2$Cl$_2$/MeOH, 99/1 to remove non polar impurities, then with CH$_2$Cl$_2$/MeOH 98/2 to 95/5). Collected fractions were concentrated under reduced pressure to afford the title compound (110 mg, 35.8% yield) as a white solid.

LCMS (e): Rt=2.98 min, M/z=631.44 (M+H)$^+$

Example 84

1-(6-(2-((4-(1-(2-(1H-1,2,4-triazol-1-yl)acetyl)piperidin-4-yl)-2-methylbenzyl)oxy)-3,5-difluorophenyl)pyridin-2-yl)piperidine-4-carboxylic acid, Sodium salt

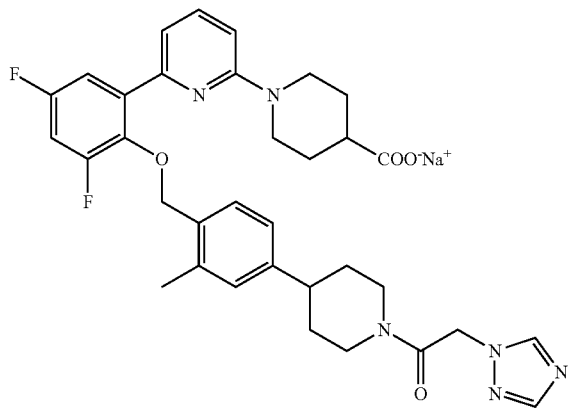

To a solution of 1-(6-(2-((4-(1-(2-(1H-1,2,4-triazol-1-yl)acetyl)piperidin-4-yl)-2-methylbenzyl)oxy)-3,5-difluorophenyl)pyridin-2-yl)piperidine-4-carboxylic acid (110 mg, 0.174 mmol) in Water (10 mL) was added sodium bicarbonate (14.65 mg, 0.174 mmol). The reaction mixture was stirred at 25° C. for 5 minutes and then was transferred to a lyophilization flask and lyophilized for 16 hours to afford the title compound (98 mg, 85% yield) as an off white solid.

LCMS (a): Rt=2.29 min, M/z=631.24 (M+H)$^+$

1H NMR (d6-DMSO, ppm): 8.47 (s, 1H), 7.94 (s, 1H), 7.5 (dd, 1H), 7.36 (m, 2H), 7.11 (d, 1H), 7.03 (m, 3H), 6.8 (d, 1H), 5.31 (q, 2H), 4.84 (s, 2H), 4.45 (m, 1H), 4.15 (m, 1H), 4.12 (m, 1H), 4.01 (m, 1H), 3.17 (m, 1H), 2.88 (m, 2H), 2.72 (m, 2H), 2.21 (s, 3H), 1.97 (m, 1H), 1.82 to 1.65 (m, 5H), 1.53 to 1.45 (m, 3H)

Intermediate 18: ethyl 1-(6-(2-((4-bromo-2-methoxybenzyl)oxy)-3,5-difluorophenyl)pyridin-2-yl)piperidine-4-carboxylate

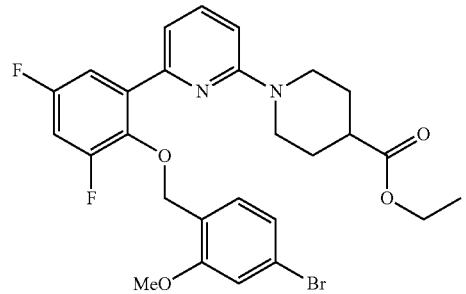 [SMILES: CCOC(=O)C1CCN(c2cccc(-c3cc(F)cc(F)c3OCc3ccc(Br)cc3OC)n2)CC1]

To a solution of ethyl 1-(6-(3,5-difluoro-2-hydroxyphenyl)pyridin-2-yl)piperidine-4-carboxylate (2 g, 5.52 mmol) in Acetone (50 mL) stirred under nitrogen atmosphere at 25° C., were added Cs$_2$CO$_3$ (3.60 g, 11.04 mmol) followed by 4-bromo-1-(bromomethyl)-2-methoxybenzene (2.318 g, 8.28 mmol). The reaction mixture was stirred at 70° C. for 12 hours, then was cooled and concentrated under reduced pressure. The crude residue was dissolved in water (25 mL). After extraction with EtOAc (3×35 mL), the combined organic phase was washed with water (25 mL) followed by a saturated NaCl solution (aq. 30 mL), dried over over anhydrous Na$_2$SO$_4$, filtered and concentrated under reduced pressure. The crude product was purified by column chromatography (100-200 mesh silica gel, eluted with EtOAc/Hexane 4/96 to 6/94 to remove non-polar impurities, then with EtOAc/Hexane 8/92 to 10/90). The pure fractions were collected and concentrated under reduced pressure to afford the title compound (1.8 g, 58.1% yield) as a colorless gum.

LCMS (e): Rt=4.56 min, M/z=561.27-563.29 (M+H)$^+$

Intermediate 19: ethyl 1-(6-(3,5-difluoro-2-((2-methoxy-4-(1-(2,2,2-trifluoroethyl)-1,2,3,6-tetrahydropyridin-4-yl)benzyl)oxy)phenyl)pyridin-2-yl)piperidine-4-carboxylate

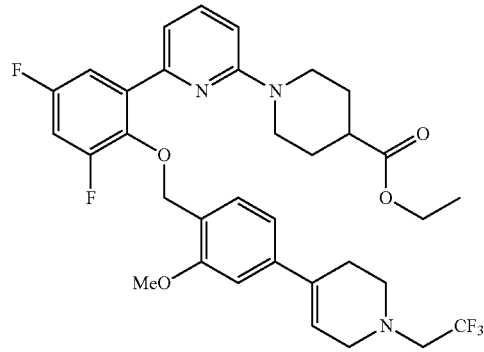 [SMILES: CCOC(=O)C1CCN(c2cccc(-c3cc(F)cc(F)c3OCc3ccc(C4=CCN(CC(F)(F)F)CC4)cc3OC)n2)CC1]

To a solution of ethyl 1-(6-(2-((4-bromo-2-methoxybenzyl)oxy)-3,5-difluorophenyl)pyridin-2-yl)piperidine-4-carboxylate (775 mg, 1.38 mmol) and 4-(4,4,5,5-tetramethyl-1,3,2-dioxaborolan-2-yl)-1-(2,2,2-trifluoroethyl)-1,2,3,6-tetrahydropyridine (703 mg, 2.416 mmol) in DME (15 mL) and Water (0.25 mL) was added Na$_2$CO$_3$ (293 mg, 2.76 mmol). Argon was purged through the reaction mixture for 20 minutes and then was added tetrakis(triphenylphosphine)palladium(0) (160 mg, 0.138 mmol). After purging with Argon for additional 5 minutes, the reaction mixture was heated at 100° C. for 16 hours, then was cooled, filtered through a celite pad and washed with EtOAc (3×25 mL). The filtrate was concentrated under reduced pressure. The crude product was purified by column chromatography (100-200 mesh silica, eluted with EtOAc/Hexane 8/92 to 10/90 to remove nonpolar impurities and then with EtOAc/Hexane 12/88 to 16/84). Collected fractions were concentrated under reduced pressure to afford the title compound (400 mg, 39.0% yield) as a colorless gum.

LCMS (e): Rt=4.72 min, M/z=646.43 (M+H)+

Example 85 ethyl 1-(6-(3,5-difluoro-2-((2-methoxy-4-(1-(2,2,2-trifluoroethyl)piperidin-4-yl)benzyl)oxy)phenyl)pyridin-2-yl)piperidine-4-carboxylate

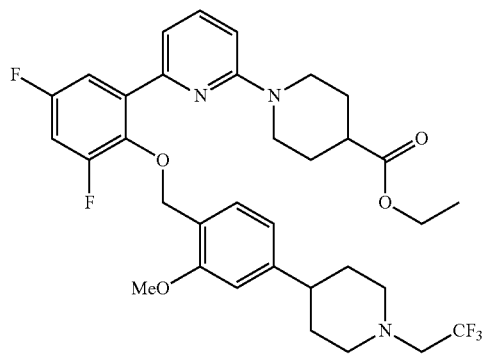 [SMILES: CCOC(=O)C1CCN(c2cccc(-c3cc(F)cc(F)c3OCc3ccc(C4CCN(CC(F)(F)F)CC4)cc3OC)n2)CC1]

To a solution of ethyl 1-(6-(3,5-difluoro-2-((2-methoxy-4-(1-(2,2,2-trifluoroethyl)-1,2,3,6-tetrahydropyridin-4-yl)benzyl)oxy)phenyl)pyridin-2-yl)piperidine-4-carboxylate (400 mg, 0.620 mmol) in EtOAc (10 mL) was added platinum(IV) oxide (40 mg, 0.176 mmol). Then reaction mixture was stirred under Hydrogen pressure for 6 hours, and then was filtered on a celite pad and washed with EtOAc (3×5 mL). The filtrate was concentrated under reduced pressure. The crude product was purified by column chromatography (100-200 mesh silica, eluted with EtOAC/Hexane 2/98 to 3/97 to remove non polar impurities was removed, then with EtOAc/Hexane 4/96 to 7/93). Collected fractions were concentrated under reduced pressure. The product was then purified by prep-HPLC.

Prep HPLC Conditions:
MP-A: 10 mM Ammonium Bicarbonate (Aq)
MP-B: Acetonitrile
Column: X Bridge C18 (50×19)10 u
Method: Isocratic (A:B)=15:85
Flow: 17 ml/min
Solubility: ACN+Water+THF
Volume: 250 mL Collected fractions were lyophilized for 16 hours to afford the title compound (90 mg, 22.41% yield) as a white solid.

LCMS (f): Rt=5.13 min, M/z=647.9 (M+H)+

Example 86

1-(6-(3,5-difluoro-2-((2-methoxy-4-(1-(2,2,2-trifluoroethyl)piperidin-4-yl)benzyl)oxy)phenyl)pyridin-2-yl)piperidine-4-carboxylic acid

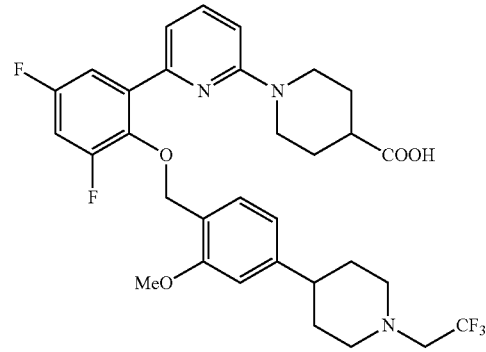

To a solution of ethyl 1-(6-(3,5-difluoro-2-((2-methoxy-4-(1-(2,2,2-trifluoroethyl)piperidin-4-yl)benzyl)oxy)phenyl)pyridin-2-yl)piperidine-4-carboxylate (90 mg, 0.139 mmol) in THF (0.5 mL) and Water (0.1 mL) stirred at 0° C., was added NaOH (0.139 mL, solution 1M, 0.139 mmol). The reaction mixture was stirred at 25° C. for 12 hours and then was concentrated under reduced pressure to remove the volatiles. The crude product was dissolved in water (5 mL) and washed with diethyl ether (3×15 mL). Then the aqueous phase was acidified with a 5% citric acid solution up to pH 5 at 0° C. The resulting precipitate was filtered, washed with cold water and dried under high vacuum to afford the title compound (75 mg, 86% yield) as a white solid.

LCMS (e): Rt=3.46 min, M/z=620.41 (M+H)+

Example 87

1-(6-(3,5-difluoro-2-((2-methoxy-4-(1-(2,2,2-trifluoroethyl)piperidin-4-yl)benzyl)oxy)phenyl)pyridin-2-yl)piperidine-4-carboxylic acid, Sodium salt

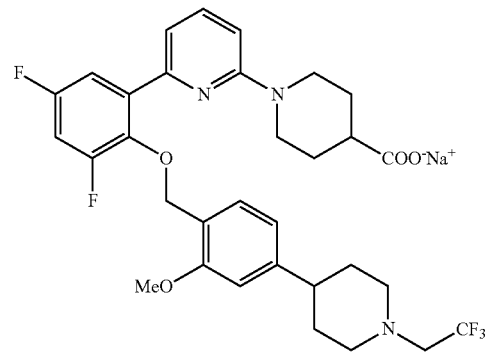

To a solution of 1-(6-(3,5-difluoro-2-((2-methoxy-4-(1-(2,2,2-trifluoroethyl)piperidin-4-yl)benzyl)oxy)phenyl)pyridin-2-yl)piperidine-4-carboxylic acid (75 mg, 0.121 mmol) in Water (5 mL) was added sodium bicarbonate (10.17 mg, 0.121 mmol) in Water (2 mL). The reaction mixture was stirred at 25° C. for 20 minutes and then it was transferred to a lyophilization flask and lyophilized for 12 hours to afford the title compound (69 mg, 85% yield) as an off white solid.

LCMS (a): Rt=2.72 min, M/z=620.22 (M+H)+

1H NMR (DMSO d6 ppm): 7.48 (t, 1H), 7.39 (m, 1H), 7.33 (m, 1H), 7.13 (d, 2H), 6.77 (m, 3H), 4.85 (s, 2H), 4.15 (m, 1H), 4.12 (m, 1H), 3.68 (s, 3H), 3.18 (q, 2H), 3.01 (m, 2H), 2.88 (m, 2H), 2.44 (m, 3H), 1.99 (m, 1H), 1.78 to 1.62 (m, 6H), 1.5 (m, 2H)

Intermediate 20:
4-bromo-2-(oxetan-3-yloxy)benzaldehyde

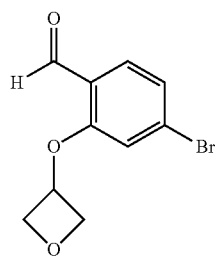 [SMILES: O=Cc1ccc(Br)cc1OC1COC1]

To a solution of 4-bromo-2-hydroxybenzaldehyde (3 g, 14.92 mmol) in DMF (15 mL) stirred under Nitrogen atmosphere were added Cs2CO3 (9.73 g, 29.8 mmol) and then 3-bromooxetane (3.07 g, 22.39 mmol). The reaction mixture was stirred at 100° C. for 16 hours, then cooled, and partitioned between water (20 ml) and EtOAc (30 mL). The organic phase was separated and the aqueous phase was further extracted with EtOAc (2×30 mL). The combined organic phase was washed with brine solution (30 ml), dried over anhydrous Na2SO4 and then concentrated under reduced pressure to afford the title compound (3 g, 78% yield) as brown solid.

LCMS (e): Rt=2.48 min, M/z=255.13 (M+H)+

Intermediate 21: 2-(oxetan-3-yloxy)-4-(1-(2,2,2-trifluoroethyl)-1,2,3,6-tetrahydropyridin-4-yl)benzaldehyde

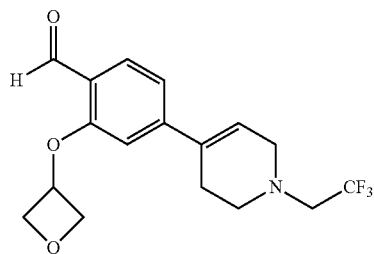 [SMILES: O=Cc1ccc(C2=CCN(CC(F)(F)F)CC2)cc1OC1COC1]

To a stirred solution of 4-bromo-2-(oxetan-3-yloxy)benzaldehyde (1 g, 3.89 mmol) and 4-(4,4,5,5-tetramethyl-1,3,2-dioxaborolan-2-yl)-1-(2,2,2-trifluoroethyl)-1,2,3,6-tetrahydropyridine (1.699 g, 5.83 mmol) in DME (10 mL) and Water (2 mL) was added portion wise Na2CO3 (0.825 g, 7.78 mmol). After addition, the reaction mixture was purged with argon gas for 30 minutes and then Pd(PPh3)4 (0.449 g, 0.389 mmol) was added. The reaction mixture was further purged with argon gas for 30 minutes and then was stirred at 100° C. for 18 hours and cooled. The insoluble material was filtered on a celite pad and the filtrate was concentrated under reduced pressure. The crude residue was partitioned between EtOAc (50 mL) and water (20 mL). The organic phase was separated and the aqueous layer was further extracted with EtOAc (2×20mL). The combined organic phase was washed with brine solution (30 mL), dried over anhydrous Na2SO4 and concentrated under reduced pressure. The crude product was purified by column chromatography (100-200 mesh silica gel (2 g), initially eluted with EtOAc/Hexane 6/94 to removed non-polar impurities, and then with EtOAc/Hexane 15/85). Collected fractions were concentrated under reduced pressure to afford the title compound (800 mg, 57.4% yield) as a brown liquid.

LCMS (a): Rt=2.25 min, M/z=342.03 (M+H)+

Intermediate 22: (2-(oxetan-3-yloxy)-4-(1-(2,2,2-trifluoroethyl)piperidin-4-yl)phenyl)methanol

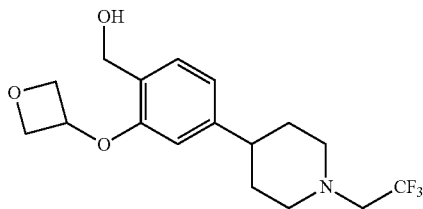 [SMILES: OCc1ccc(C2CCN(CC(F)(F)F)CC2)cc1OC1COC1]

To a solution of 2-(oxetan-3-yloxy)-4-(1-(2,2,2-trifluoroethyl)-1,2,3,6-tetrahydropyridin-4-yl)benzaldehyde (800 mg, 2.344 mmol) in EtOAc (10 mL) stirred at 0° C. under Nitrogen atmosphere was added carefully platinum(IV) oxide (80 mg, 0.352 mmol). After addition the reaction mixture was then stirred under Hydrogen pressure at 25° C. for 16 hours. The catalyst was filtered off on a celite pad and the filtrate was concentrated under reduced pressure to afford the title compound (600 mg, 48% yield) as a colorless liquid.

LCMS (a): Rt=1.55 min, M/z=346.21 (M+H)+

Example 88 ethyl 1-(6-(3,5-difluoro-2-((2-(oxetan-3-yloxy)-4-(1-(2,2,2-trifluoroethyl)piperidin-4-yl)benzyl)oxy)phenyl)pyridin-2-yl)piperidine-4-carboxylate

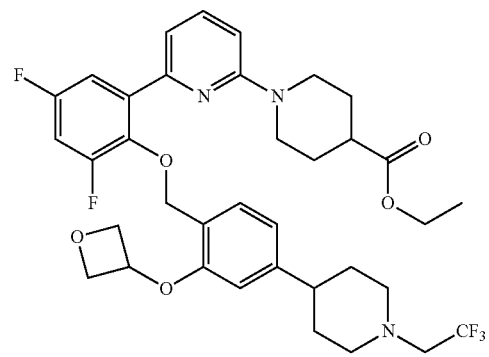 [SMILES: CCOC(=O)C1CCN(c2cccc(-c3cc(F)cc(F)c3OCc3ccc(C4CCN(CC(F)(F)F)CC4)cc3OC3COC3)n2)CC1]

To a solution of ethyl 1-(6-(3,5-difluoro-2-hydroxyphenyl)pyridin-2-yl)piperidine-4-carboxylate (500 mg, 1.380 mmol), (2-(oxetan-3-yloxy)-4-(1-(2,2,2-trifluoroethyl)piperidin-4-yl)phenyl)methanol (572 mg, 1.656 mmol) and triphenylphosphine (3619 mg, 13.80 mmol) in THF (25 mL) stirred under nitrogen at 25° C., was added dropwise a solution of DEAD (2.185 mL, 13.80 mmol) in THF (25 mL) during 5 minutes. The reaction mixture was stirred at 25° C. for 3 hours, then was quenched with water (10 mL). Ethyl acetate (15 mL) was added. The organic phase was separated and the aqueous phase was further extracted with EtOAc (2×10 mL). The combined organic phase was washed with brine solution (30 mL), dried over $Na_2SO_4$ and concentrated under reduced pressure. The crude product was purified by Prep-HPLC.

Prep-HPLC Conditions:
  Column: xbridge (50×19)
  MP-A: 10 mM Ammonium Bicarbonate (Aq)
  MP-B: Acetonitrile
  Method: Isocratic (A:B)=25:75
  Flow: 18 ml/min
  Solubility: ACN+THF+centrifuge
  Fraction volume: 250 ml Collected fractions were concentrated under reduced pressure to remove ACN. After extraction with EtOAc (20 mL), the organic phase was dried over anhydrous $Na_2SO_4$ and concentrated under reduced pressure to afford the title compound (130 mg, 13.30% yield) as a gummy solid.

LCMS (a): Rt=3.51 min, M/z=690.3 (M+H)$^+$

Example 89

1-(6-(3,5-difluoro-2-((2-(oxetan-3-yloxy)-4-(1-(2,2,2-trifluoroethyl)piperidin-4-yl)benzyl)oxy)phenyl)pyridin-2-yl)piperidine-4-carboxylic acid

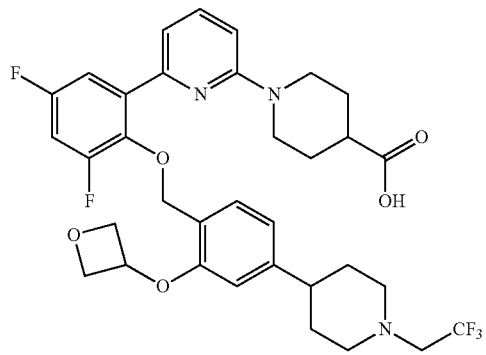 [SMILES: O=C(O)C1CCN(c2cccc(-c3cc(F)cc(F)c3OCc3ccc(C4CCN(CC(F)(F)F)CC4)cc3OC3COC3)n2)CC1]

To a stirred solution of ethyl 1-(6-(3,5-difluoro-2-((2-(oxetan-3-yloxy)-4-(1-(2,2,2-trifluoroethyl)piperidin-4-yl)benzyl)oxy)phenyl)pyridin-2-yl)piperidine-4-carboxylate (130 mg, 0.188 mmol) in EtOH (3 mL) at 0° C., was added NaOH (0.377 mL, solution 1M, 0.377 mmol). The reaction mixture was stirred at 0° C. for 30 minutes, then at 25° C. for 12 hours and then was concentrated under reduced pressure. The crude residue was diluted with water (10 mL) and the pH was adjusted to 5 with a 5% citric acid solution (5 mL). The resulting precipitate was filtered, washed with water (10 mL) and then dried under vacuum to the title compound (70 mg, 55.1% yield) as off white solid.

LCMS (e): Rt=3.49 min, M/z=662.68 (M+H)$^+$

Example 90

1-(6-(3,5-difluoro-2-((2-(oxetan-3-yloxy)-4-(1-(2,2,2-trifluoroethyl)piperidin-4-yl)benzyl)oxy)phenyl)pyridin-2-yl)piperidine-4-carboxylic acid, Sodium salt

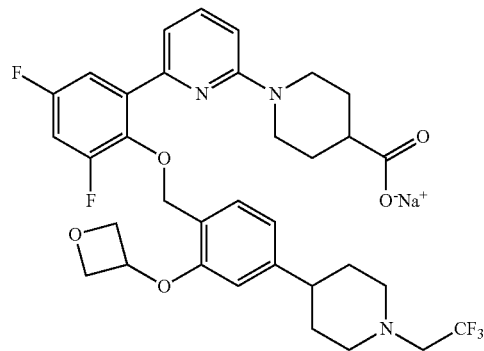

To a solution of 1-(6-(3,5-difluoro-2-((2-(oxetan-3-yloxy)-4-(1-(2,2,2-trifluoroethyl)piperidin-4-yl)benzyl)oxy)phenyl)pyridin-2-yl)piperidine-4-carboxylic acid (70 mg, 0.106 mmol) in Water (5 mL) was added sodium bicarbonate (8.89 mg, 0.106 mmol) in Water (2 mL). The reaction mixture was stirred at 25° C. for 20 minutes and then was transferred to a lyophilization flask and lyophilized for 12 hours to afford the title compound (63 mg, 86% yield) as off white solid.

LCMS (e): Rt=3.36 min, M/z=662.61 (M+H)$^+$

1H NMR (d6-DMSO, ppm): 7.47 (t, 1H), 7.39 (m, 1H), 7.33 (m, 1H), 7.19 (d, 1H), 7.13 (d, 1H), 6.78 (t, 2H), 6.35 (s, 1H), 5.16 (m, 1H), 4.9 (s, 2H), 4.84 (t, 2H), 4.36 (m, 2H), 4.14 (m, 1H), 4.11 (m, 1H), 3.18 (q, 2H), 2.99 (m, 2H), 2.88 (m, 2H), 2.42 (m, 3H), 1.98 (m, 1H), 1.77 (m, 2H), 1.64 (m, 4H), 1.5 (m, 2H)

Intermediate 23: 2-methyl-4-((1-(2,2,2-trifluoroethyl)piperidin-4-yl)oxy)benzaldehyde

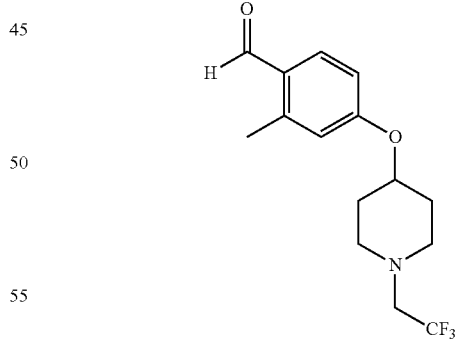

To a solution of 4-hydroxy-2-methylbenzaldehyde (2 g, 14.69 mmol), 1-(2,2,2-trifluoroethyl)piperidin-4-ol (4.04 g, 22.03 mmol) and triphenylphosphine (7.71 g, 29.4 mmol) in THF (50 mL) was added DIAD (5.94 g, 29.4 mmol) over a period of 10 minutes at 0° C. The reaction mixture was then allowed to stir at 25° C. under Nitrogen for 3 hours and then was partitioned between water (30 mL) and EtOAc (50 mL). The organic phase was separated and the aqueous phase was further extracted with EtOAc (2×30 mL). The combined organic phase was washed with brine solution (10 mL), dried over anhydrous Na$_2$SO$_4$ and then concentrated under reduced pressure. The crude product was purified by column chromatography (100-200 mesh silica gel, initially eluted with EtOAc/Hexane 6/94 to removed non-polar impurities, and then with EtOAc/Hexane 15/85). Collected fractions were concentrated under reduced pressure to afford the title compound (1.3 g, 27.4% yield) as a brown liquid.

LCMS (a): Rt=2.37 min, M/z=302.29 (M+H)$^+$

Intermediate 24: (2-methyl-4-((1-(2,2,2-trifluoro-ethyl)piperidin-4-yl)oxy)phenyl)methano

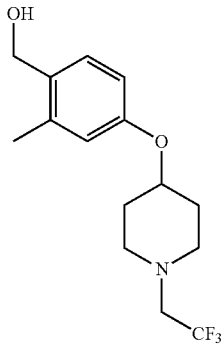 [SMILES: Cc1cc(OC2CCN(CC(F)(F)F)CC2)ccc1CO]

To a solution of 2-methyl-4-((1-(2,2,2-trifluoroethyl)piperidin-4-yl)oxy)benzaldehyde (1.2 g, 3.98 mmol) in EtOH (30 mL) stirred at 0° C., was added portion wise NaBH$_4$ (0.301 g, 7.97 mmol). Then reaction mixture was stirred at 25° C. for 4 hours and then cold water (5 mL) was added. Solvents were removed under reduced pressure. Water (15 mL) was added to the crude product. After extraction with EtOAc (3×25 mL), the combined organic phase was dried over anhydrous Na$_2$SO$_4$, filtered and concentrated under reduced pressure. The crude product was purified by column chromatography (230-400 mesh silica, eluted with EtOAc/Hexane 12/88 to 14/86). Collected fractions were concentrated under reduced pressure to afford the title compound (900 mg, 67.5% yield) as a colorless gum.

LCMS (e): Rt=3.44 min, M/z=304.29 (M+H)$^+$

Example 91 ethyl 1-(6-(3,5-difluoro-2-((2-methyl-4-((1-(2,2,2-trifluoroethyl)piperidin-4-yl)oxy)benzyl)oxy)phenyl)pyridin-2-yl)piperidine-4-carboxylate

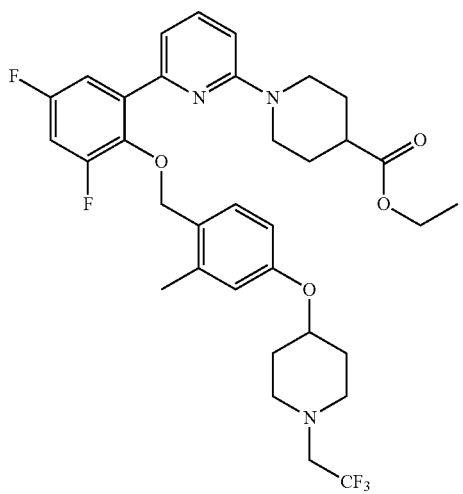 [SMILES: CCOC(=O)C1CCN(c2cccc(-c3cc(F)cc(F)c3OCc3ccc(OC4CCN(CC(F)(F)F)CC4)cc3C)n2)CC1]

To a solution of ethyl 1-(6-(3,5-difluoro-2-hydroxyphenyl)pyridin-2-yl)piperidine-4-carboxylate (1 g, 2.76 mmol), (2-methyl-4-((1-(2,2,2-trifluoroethyl)piperidin-4-yl)oxy)phenyl)methanol (0.837 g, 2.76 mmol) and triphenylphosphine (7.24 g, 27.6 mmol) in THF (50 mL) stirred under nitrogen at 25° C., was added dropwise a solution of DEAD (4.37 mL, 27.6 mmol) in THF (50 mL) during 5 minutes. The reaction mixture was stirred at 25° C. for 3 hours and then was partitioned between water (20 mL) and EtOAc (30 mL). The organic phase was separated and the aqueous phase was further extracted with EtOAc (2×20 mL). The combined organic phase was washed with brine solution (10 mL), dried over anhydrous Na$_2$SO$_4$ and then concentrated under reduced pressure. The crude product was purified by column chromatography (100-200mesh silica gel, initially eluted with EtOAc/Hexane 2/98 to 3/97 to removed non-polar impurities, and then with EtOAc/Hexane 10/90). Collected fractions were concentrated under reduced pressure to afford the title compound (1.7 g, 54.3% yield) as brown liquid.

LCMS a): Rt=3.86 min, M/z=648.3 (M+H)$^+$

Example 92

1-(6-(3,5-difluoro-2-((2-methyl-4-((1-(2,2,2-trifluoroethyl)piperidin-4-yl)oxy)benzyl)oxy)phenyl)pyridin-2-yl)piperidine-4-carboxylic acid

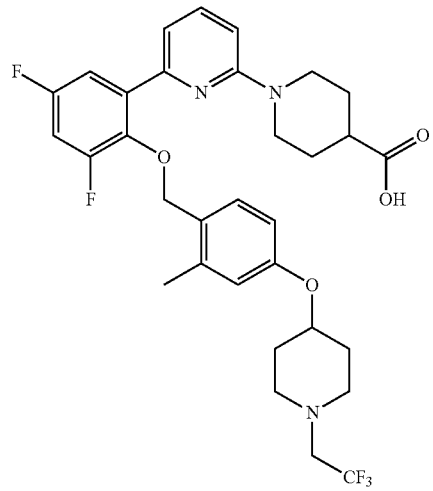 [SMILES: Cc1cc(OC2CCN(CC(F)(F)F)CC2)ccc1COc1c(F)cc(F)cc1-c1cccc(N2CCC(C(=O)O)CC2)n1]

To a solution of ethyl 1-(6-(3,5-difluoro-2-((2-methyl-4-((1-(2,2,2-trifluoroethyl)piperidin-4-yl)oxy)benzyl)oxy)phenyl)pyridin-2-yl)piperidine-4-carboxylate (500 mg, 0.772 mmol) in EtOH (10 mL) and Water (3 mL) stirred at 0° C., was added NaOH (3.09 mL, solution 1M, 3.09 mmol). The reaction mixture was stirred at 0° C. for 30 minutes, then at 25° C. for 12 hours and then was concentrated under reduced pressure to remove EtOH. The crude product was diluted with water (10 mL) and the pH was adjusted to 5 with a 5% citric acid solution. The resulting precipitate was filtered, washed with water (10 mL), then with n-pentane (10 mL) and was dried. The crude product was purified by Prep-HPLC.

Prep-HPLC Condition:
Column: XTERRA C18 (19×250)10 μ
MP-A: 5 mM Ammonium Bicarbonate (Aq)
MP-B: ACN Method: 0/20,1/20,10/80,10.5/100
Flow: 18 ml/min
Solubility: ACN+THF+centrifuge
Fraction volume: 250 ml Collected fractions were concentrated under reduced pressure to remove ACN. EtOAc (20 mL) was added and the organic phase was separated, dried over anhydrous $Na_2SO_4$ and then concentrated under reduced pressure to afford the title compound (40 mg, 8.36% yield) as off white solid.

LCMS (e): Rt=3.44 min, M/z=618.59 (M-H)⁻

Example 93

1-(6-(3,5-difluoro-2-((2-methyl-4-((1-(2,2,2-trifluoroethyl)piperidin-4-yl)oxy)benzyl)oxy)phenyl)pyridin-2-yl)piperidine-4-carboxylic acid, Sodium salt

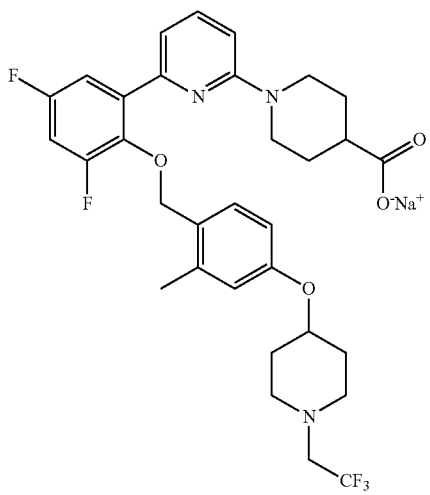

To a solution of 1-(6-(3,5-difluoro-2-((2-methyl-4-((1-(2,2,2-trifluoroethyl)piperidin-4-yl)oxy)benzyl)oxy)phenyl) pyridin-2-yl)piperidine-4-carboxylic acid (40 mg, 0.065 mmol) in Water (5 mL) was added sodium bicarbonate (5.42 mg, 0.065 mmol) in Water (2 mL). The reaction mixture was stirred at 25° C. for 20 minutes and then was transferred to a lyophilization flask and lyophilized for 12 hours to afford the title compound (35 mg, 79% yield) as an off white solid.

LCMS (e): Rt=3.93 min, M/z=620.60 (M+H)⁺

1H NMR (DMSO d6 ppm): 7.5 (dd, 1H), 7.34 (m, 2H), 7.05 (m, 2H), 6.81 (d, 1H), 6.75 (d, 1H), 6.69 (dd, 1H), 4.77 (s, 2H), 4.37 (m, 1H), 4.16 (m, 1H), 4.13 (m, 1H), 3.19 (q, 2H), 2.9 (m, 2H), 2.83 (m, 2H), 2.56 (m, 2H), 2.19 (s, 3H), 1.99 (m, 1H), 1.88 (m, 2H), 1.78 (m, 2H), 1.65 to 1.47 (m, 4H)

Biological Examples

Biological Cellular Assay

The activity of soluble guanylate cyclase (sGC) was tested in an assay based on measuring phosphorylation of the protein kinase G (PKG) substrate vasodilator-stimulated phosphoprotein (VASP) in rat aortic smooth muscle cells. Primary rat aortic smooth muscle cells were incubated at 37° C. for 10 min in the presence of 10 μM 1H-[1,2,4]oxadiazolo[4,3-a]quinoxalin-1-one (ODQ), a highly selective, and irreversible sGC heme iron oxidant. Dimethylsulfoxide (DMSO) vehicle and varying concentrations of the compound to be tested were then added. Following a 30 min incubation at 37° C., media was aspirated and the cells were rinsed with phosphate-buffered saline (PBS) and fixed with 4% formaldehyde in PBS by incubating at room temperature for 20 min. Cells were then washed with PBS and permeabilized for 10 min using 0.1% triton X-100 in PBS. Following PBS rinsing, the cells were blocked for 90 min at room temperature with blocking buffer. The buffer was aspirated and the cells were treated overnight at 4° C. with primary antibody (pSer239-VASP, rabbit polyclonal Ab) diluted 1:500 in blocking buffer. Following three washes with 0.05% Tween 20, the cells were treated for 1 h at room temperature with a fluorescent labeled secondary antibody (IRDye® 800CW Donkey Anti-Rabbit IgG) diluted 1:2500 in blocking buffer with 0.05% Tween 20. Following two washes with PBS, infrared fluorescence was measured using an Odyssey Infrared Imaging System. The activity of a test compound was determined as the pEC50 value which is the concentration able to increase by 50% (vs. Bmax) the phospho-VASP fluorescent signal. *Front. Pharmacol.,* 5 Jul. 2012|doi: 10.3389/fphar.2012.00128, Volume 3 July, 2012, Article number 128.

pEC50 values for compounds that fall within the scope of this invention are found below.

| Example No. | Cell assay pEC50 |
| --- | --- |
| 1 | 9.2 |
| 5 | 9.3 |
| 6 | 10 |
| 9 | 8 |
| 14 | 8 |
| 17 | 7.1 |
| 20 | 6.8 |
| 23 | 6.6 |
| 27 | 7.4 |
| 30 | 7.7 |
| 33 | 7.8 |
| 36 | 8 |
| 39 | 9.1 |
| 42 | 8.6 |
| 45 | 8.5 |
| 48 | 7.8 |
| 51 | 7.5 |
| 54 | 8.6 |
| 57 | 10.1 |
| 60 | 9.9 |
| 63 | 9.4 |
| 66 | 9.5 |
| 69 | 9.6 |
| 72 | 9.37 |
| 73 | 10.05 |
| 76 | 9 |
| 79 | 8.9 |
| 81 | 7.8 |
| 84 | 7.7 |
| 87 | 8.6 |
| 90 | 8.9 |
| 93 | 8.1 |

What is claimed is:

1. A compound according to formula (I):

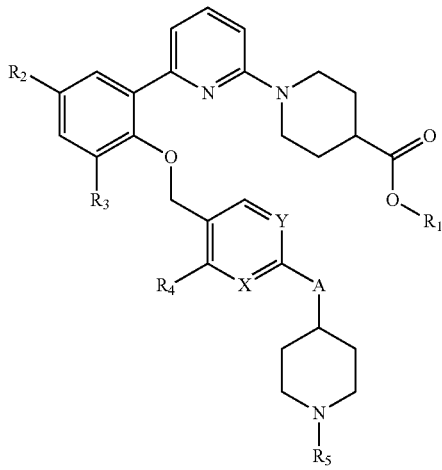

or a pharmaceutically acceptable salt thereof, wherein:
wherein:
$R_1$ is selected from H and —$C_{1-3}$alkyl;
$R_2$ and $R_3$ are each independently selected from H and halogen;
$R_4$ is selected from H, —$C_{1-3}$alkyl, —O—$C_{1-3}$alkyl, —O—$C_{3-4}$cycloalkyl, —O—$(CH_2)_p$-oxetanyl, and —O—$(CH_2)_p$-tetrahydrofuranyl;
X and Y are each CH; or if X is N, then Y is CH; or if Y is N then X is CH;
A is absent or O;
$R_5$ is selected from —$C_{1-4}$ alkyl, —$C_{3-4}$ cycloalkyl, —$(CH_2)_nCN$, —$(CH_2)_nCF_3$, —$(CH_2)_m$-tetrahydrofuranyl, —$(CH_2)_m$-oxetanyl, —$C_{2-5}$ alkyl-OH, —$C_{2-5}$ alkyl-OCH$_3$ and —CO—$R_6$;
$R_6$ is selected from —$C_{1-6}$ alkyl and —$C_{3-6}$ cycloalkyl, optionally substituted by —OH, —OCH$_3$, —CN, COOH or —F, or $R_6$ is —$(CH_2)_m$-tetrahydrofuranyl or —$(CH_2)_m$-oxetanyl, or R6 is a $(CH_2)_m$-4 to 5-membered heterocycle;
n is 1 or 2;
m is 0 or 1; and
p is 0 or 1.

2. A compound, or a pharmaceutically acceptable salt thereof, which is:
1-(6-(2-((4-(1-(cyanomethyl)piperidin-4-yl)-2-methylbenzyl)oxy)-3,5-difluorophenyl)pyridin-2-yl)piperidine-4-carboxylic acid;
1-(6-(3,5-difluoro-2-((2-methyl-4-(1-(2,2,2-trifluoroethyl)piperidin-4-yl)benzyl)oxy)phenyl)pyridin-2-yl) piperidine-4-carboxylic acid;
1-(6-(3,5-difluoro-2-((2-methyl-4-(1-(oxetane-3-carbonyl)piperidin-4-yl)benzyl)oxy)phenyl)pyridin-2-yl)piperidine-4-carboxylic acid;
1-(6-(3,5-difluoro-2-((4-methyl-6-(1-(2,2,2-trifluoroethyl)piperidin-4-yl)pyridin-3-yl)methoxy)phenyl) pyridin-2-yl)piperidine-4-carboxylic acid;
1-(6-(2-((6-(1-(cyanomethyl)piperidin-4-yl)-4-methylpyridin-3-yl)methoxy)-3,5-difluorophenyl)pyridin-2-yl)piperidine-4-carboxylic acid;
1-(6-(3,5-difluoro-2-(2-methyl-6-(1-(2,2,2-trifluoroethyl)piperidin-4-yl)pyridin-3-yl)methoxy)phenyl)pyridin-2-yl)piperidine-4-carboxylic acid;
1-(6-(3,5-difluoro-2-((2-methyl-6-(1-(oxetan-3-yl)piperidin-4-yl)pyridin-3-yl)methoxy)phenyl)pyridin-2-yl)piperidine-4-carboxylic acid;
1-(6-(3,5-difluoro-2-((2-methyl-6-(1-(tetrahydrofuran-3-yl)piperidin-4-yl)pyridin-3-yl)methoxy)phenyl)pyridin-2-yl)piperidine-4-carboxylic acid;
1-(6-(3,5-difluoro-2-((2-methyl-6-(1-((tetrahydrofuran-3-yl)methyl)piperidin-4-yl)pyridin-3-yl)methoxy)phenyl)pyridin-2-yl)piperidine-4-carboxylic acid;
1-(6-(2-((6-(1-(cyanomethyl)piperidin-4-yl)-2-methylpyridin-3-yl)methoxy)-3,5-difluorophenyl)pyridin-2-yl)piperidine-4-carboxylic acid;
1-(6-(3,5-difluoro-2-((2-methyl-6-(1-(oxetane-3-carbonyl)piperidin-4-yl)pyridin-3-yl)methoxy)phenyl)pyridin-2-yl)piperidine-4-carboxylic acid;
1-(6-(3,5-difluoro-2-((6-(1-(2-hydroxyacetyl)piperidin-4-yl)-2-methylpyridin-3-yl)methoxy)phenyl)pyridin-2-yl)piperidine-4-carboxylic acid;
1-(6-(3-chloro-2-((2-methyl-4-(1-(oxetan-3-yl)piperidin-4-yl)benzyl)oxy)phenyl)pyridin-2-yl)piperidine-4-carboxylic acid;
1-(6-(3,5-difluoro-2-((2-methyl-4-(1-(oxetan-3-yl)piperidin-4-yl)benzyl)oxy)phenyl)pyridin-2-yl)piperidine-4-carboxylic acid;
1-(6-(3,5-difluoro-2-((2-methyl-4-(1-(tetrahydrofuran-3-yl)piperidin-4-yl)benzyl)oxy)phenyl)pyridin-2-yl)piperidine-4-carboxylic acid;
1-(6-(2-((4-(1-cyclopropylpiperidin-4-yl)-2-methylbenzyl)oxy)-3,5-difluorophenyl)pyridin-2-yl)piperidine-4-carboxylic acid;
1-(6-(3,5-difluoro-2-((4-(1-(2-methoxyethyl)piperidin-4-yl)-2-methylbenzyl)oxy)phenyl)pyridin-2-yl)piperidine-4-carboxylic acid;
1-(6-(3,5-difluoro-2-((4-(1-(2-hydroxyethyl)piperidin-4-yl)-2-methylbenzyl)oxy)phenyl)pyridin-2-yl)piperidine-4-carboxylic acid;
1-(6-(3,5-difluoro-2-((2-methyl-4-(1-(3,3,3-trifluoropropyl)piperidin-4-yl)benzyl)oxy)phenyl)pyridin-2-yl)piperidine-4-carboxylic acid;
1-(6-(3,5-difluoro-2-((4-(1-(2-hydroxyacetyl)piperidin-4-yl)-2-methylbenzyl)oxy)phenyl)pyridin-2-yl)piperidine-4-carboxylic acid;
1-(6-(3,5-difluoro-2-((4-(1-(2-methoxyacetyl)piperidin-4-yl)-2-methylbenzyl)oxy)phenyl)pyridin-2-yl)piperidine-4-carboxylic acid;
1-(6-(2-((4-(1-(2-cyanoacetyl)piperidin-4-yl)-2-methylbenzyl)oxy)-3,5-difluorophenyl)pyridin-2-yl)piperidine-4-carboxylic acid;
1-(6-(2-((4-(1-(2-cyclopropylacetyl)piperidin-4-yl)-2-methylbenzyl)oxy)-3,5-difluorophenyl)pyridin-2-yl) piperidine-4-carboxylic acid;
1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid;
(S)-1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid;
(R)-1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid;
1-(6-(3,5-difluoro-2-((2-methyl-4-(1-(2-(oxetan-3-yl)acetyl)piperidin-4-yl)benzyl)oxy)phenyl)pyridin-2-yl) piperidine-4-carboxylic acid;

1-(6-(3,5-difluoro-2-((2-methyl-4-(1-(2-(tetrahydrofuran-3-yl)acetyl)piperidin-4-yl)benzyl)oxy)phenyl)pyridin-2-yl)piperidine-4-carboxylic acid;

1-(6-(2-((4-(1-(2-carboxyacetyl)piperidin-4-yl)-2-methylbenzyl)oxy)-3,5-difluorophenyl)pyridin-2-yl)piperidine-4-carboxylic acid;

1-(6-(2-((4-(1-(2-(1H-1,2,4-triazol-1-yl)acetyl)piperidin-4-yl)-2-methylbenzyl)oxy)-3,5-difluorophenyl)pyridin-2-yl)piperidine-4-carboxylic acid;

1-(6-(3,5-difluoro-2-((2-methoxy-4-(1-(2,2,2-trifluoroethyl)piperidin-4-yl)benzyl)oxy)phenyl)pyridin-2-yl)piperidine-4-carboxylic acid;

1-(6-(3,5-difluoro-2-((2-(oxetan-3-yloxy)-4-(1-(2,2,2-trifluoroethyl)piperidin-4-yl)benzyl)oxy)phenyl)pyridin-2-yl)piperidine-4-carboxylic acid; or 1-(6-(3,5-difluoro-2-((2-methyl-4-((1-(2,2,2-trifluoroethyl)piperidin-4-yl)oxy)benzyl)oxy)phenyl)pyridin-2-yl)piperidine-4-carboxylic acid.

3. A pharmaceutical composition comprising a compound, or a pharmaceutically acceptable salt thereof, according to claim 1 and one or more pharmaceutically acceptable excipients.

4. A compound which is 1-(6-(3,5-difluoro-2-((4-methyl-6-(1-(2,2,2-trifluoroethyl)piperidin-4-yl)pyridin-3-yl)methoxy)phenyl)pyridin-2-yl)piperidine-4-carboxylic acid, sodium salt.

5. A compound which is 1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid, sodium salt.

6. A compound which is 1-(6-(3,5-difluoro-2-((4-methyl-6-(1-(2,2,2-trifluoroethyl)piperidin-4-yl)pyridin-3-yl)methoxy)phenyl)pyridin-2-yl)piperidine-4-carboxylic acid, or a pharmaceutically acceptable salt thereof.

7. A compound which is 1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid, or a pharmaceutically acceptable salt thereof.

8. A compound which is 1-(6-(3,5-difluoro-2-((2-methyl-4-(1-(2,2,2-trifluoroethyl)piperidin-4-yl)benzyl)oxy)phenyl)pyridin-2-yl)piperidine-4-carboxylic acid.

9. A compound which is 1-(6-(3,5-difluoro-2-((2-methyl-4-(1-(2,2,2-trifluoroethyl)piperidin-4-yl)benzyl)oxy)phenyl)pyridin-2-yl)piperidine-4-carboxylic acid, sodium salt.

10. A compound which is:

1-(6-(2-((4-(1-(cyanomethyl)piperidin-4-yl)-2-methylbenzyl)oxy)-3,5-difluorophenyl)pyridin-2-yl)piperidine-4-carboxylic acid, Sodium salt;

1-(6-(3,5-difluoro-2-((2-methyl-4-(1-(2,2,2-trifluoroethyl)piperidin-4-yl)benzyl)oxy)phenyl)pyridin-2-yl)piperidine-4-carboxylic acid, Sodium salt;

1-(6-(3,5-difluoro-2-((2-methyl-4-(1-(oxetane-3-carbonyl)piperidin-4-yl)benzyl)oxy)phenyl)pyridin-2-yl)piperidine-4-carboxylic acid, Sodium salt;

1-(6-(3,5-difluoro-2-((4-methyl-6-(1-(2,2,2-trifluoroethyl)piperidin-4-yl)pyridin-3-yl)methoxy)phenyl)pyridin-2-yl)piperidine-4-carboxylic acid, Sodium salt;

1-(6-(2-((6-(1-(cyanomethyl)piperidin-4-yl)-4-methylpyridin-3-yl)methoxy)-3,5-difluorophenyl)pyridin-2-yl)piperidine-4-carboxylic acid, Sodium salt;

1-(6-(3,5-difluoro-2-((2-methyl-6-(1-(2,2,2-trifluoroethyl)piperidin-4-yl)pyridin-3-yl)methoxy)phenyl)pyridin-2-yl)piperidine-4-carboxylic acid, Sodium salt;

1-(6-(3,5-difluoro-2-((2-methyl-6-(1-(oxetan-3-yl)piperidin-4-yl)pyridin-3-yl)methoxy)phenyl)pyridin-2-yl)piperidine-4-carboxylic acid, Sodium salt;

1-(6-(3,5-difluoro-2-((2-methyl-6-(1-(tetrahydrofuran-3-yl)piperidin-4-yl)pyridin-3-yl)methoxy)phenyl)pyridin-2-yl)piperidine-4-carboxylic acid, Sodium salt;

1-(6-(3,5-difluoro-2-((2-methyl-6-(1-((tetrahydrofuran-3-yl)methyl)piperidin-4-yl)pyridin-3-yl)methoxy)phenyl)pyridin-2-yl)piperidine-4-carboxylic acid, Sodium salt;

1-(6-(2-((6-(1-(cyanomethyl)piperidin-4-yl)-2-methylpyridin-3-yl)methoxy)-3,5-difluorophenyl)pyridin-2-yl)piperidine-4-carboxylic acid, Sodium salt;

1-(6-(3,5-difluoro-2-((2-methyl-6-(1-(oxetane-3-carbonyl)piperidin-4-yl)pyridin-3-yl)methoxy)phenyl)pyridin-2-yl)piperidine-4-carboxylic acid, Sodium salt;

1-(6-(3,5-difluoro-2-((6-(1-(2-hydroxyacetyl)piperidin-4-yl)-2-methylpyridin-3-yl)methoxy)phenyl)pyridin-2-yl)piperidine-4-carboxylic acid, Sodium salt;

1-(6-(3-chloro-2-((2-methyl-4-(1-(oxetan-3-yppiperidin-4-yl)benzyl)oxy)phenyl)pyridin-2-yl)piperidine-4-carboxylic acid, Sodium salt;

1-(6-(3,5-difluoro-2-((2-methyl-4-(1-(oxetan-3-yl)piperidin-4-yl)benzyl)oxy)phenyl)pyridin-2-yl)piperidine-4-carboxylic acid, Sodium salt;

1-(6-(3,5-difluoro-2-((2-methyl-4-(1-(tetrahydrofuran-3-yl)piperidin-4-yl)benzyl)oxy)phenyl)pyridin-2-yl)piperidine-4-carboxylic acid, Sodium salt;

1-(6-(2-((4-(1-cyclopropylpiperidin-4-yl)-2-methylbenzyl)oxy)-3,5-difluorophenyl)pyridin-2-yl)piperidine-4-carboxylic acid, Sodium salt;

1-(6-(3,5-difluoro-2-((4-(1-(2-methoxyethyl)piperidin-4-yl)-2-methylbenzyl)oxy)phenyl)pyridin-2-yl)piperidine-4-carboxylic acid, Sodium salt;

1-(6-(3,5-difluoro-2-((4-(1-(2-hydroxyethyppiperidin-4-yl)-2-methylbenzyl)oxy)phenyl)pyridin-2-yl)piperidine-4-carboxylic acid, Sodium salt;

1-(6-(3,5-difluoro-2-((2-methyl-4-(1-(3,3,3-trifluoropropyl)piperidin-4-yl)benzyl)oxy)phenyl)pyridin-2-yl)piperidine-4-carboxylic acid, Sodium salt;

1-(6-(3,5-difluoro-2-((4-(1-(2-hydroxyacetyl)piperidin-4-yl)-2-methylbenzyl)oxy)phenyl)pyridin-2-yl)piperidine-4-carboxylic acid, Sodium salt;

1-(6-(3,5-difluoro-2-((4-(1-(2-methoxyacetyl)piperidin-4-yl)-2-methylbenzyl)oxy)phenyl)pyridin-2-yl)piperidine-4-carboxylic acid, Sodium salt;

1-(6-(2-((4-(1-(2-cyanoacetyl)piperidin-4-yl)-2-methylbenzyl)oxy)-3,5-difluorophenyl)pyridin-2-yl)piperidine-4-carboxylic acid, Sodium salt;

1-(6-(2-((4-(1-(2-cyclopropylacetyl)piperidin-4-yl)-2-methylbenzyl)oxy)-3,5-difluorophenyl)pyridin-2-yl)piperidine-4-carboxylic acid, Sodium salt;

1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid, Sodium salt;

(S)-1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid, Sodium salt;

(R)-1-(6-(3,5-difluoro-2-((2-methyl-4-(1-(tetrahydrofuran-3-carbonyl)piperidin-4-yl)benzyl)oxy)phenyl)pyridin-2-yl)piperidine-4-carboxylic acid, Sodium salt;

1-(6-(3,5-difluoro-2-((2-methyl-4-(1-(2-(oxetan-3-yl)acetyl)piperidin-4-yl)benzyl)oxy)phenyl)pyridin-2-yl)piperidine-4-carboxylic acid, Sodium salt;

1-(6-(3,5-difluoro-24(2-methyl-4-(1-(2-(tetrahydrofuran-3-yl)acetyl)piperidin-4-yl)benzyl)oxy)phenyl)pyridin-2-yl)piperidine-4-carboxylic acid, Sodium salt;

1-(6-(2-((4-(1-(2-carboxyacetyl)piperidin-4-yl)-2-methylbenzyl)oxy)-3,5-difluorophenyl)pyridin-2-yl)piperidine-4-carboxylic acid, di-Sodium salt;

1-(6-(2-((4-(1-(2-(1H-1,2,4-triazol-1-yl)acetyl)piperidin-4-yl)-2-methylbenzyl)oxy)-3,5-difluorophenyl)pyridin-2-yl)piperidine-4-carboxylic acid, Sodium salt;
1-(6-(3,5-difluoro-2-((2-methoxy-4-(1-(2,2,2-trifluoroethyl)piperidin-4-yl)benzyl)oxy)phenyl)pyridin-2-yl) piperidine-4-carboxylic acid, Sodium salt;
1-(6-(3,5-difluoro-2-((2-(oxetan-3-yloxy)-4-(1-(2,2,2-trifluoroethyl)piperidin-4-yl)benzyl)oxy)phenyl)pyridin-2-yl)piperidine-4-carboxylic acid, Sodium salt; or
1-(6-(3,5-difluoro-2-((2-methyl-4-((1-(2,2,2-trifluoroethyl)piperidin-4-yl)oxy)benzyl)oxy)phenyl)pyridin-2-ylpiperidine-4carboxylic acid, Sodium salt.

* * * * *